US011737800B2

(12) United States Patent
Greenhalgh et al.

(10) Patent No.: US 11,737,800 B2
(45) Date of Patent: Aug. 29, 2023

(54) ATTACHMENT DEVICE AND METHOD FOR USE

(71) Applicant: Stout Medical Group, L.P., Warrington, PA (US)

(72) Inventors: E. Skott Greenhalgh, Gladwyne, PA (US); Robert A. Kiefer, Quakertown, PA (US)

(73) Assignee: Stout Medical Group, L.P., Warrington, PA (US)

( * ) Notice: Subject to any disclaimer, the term of this patent is extended or adjusted under 35 U.S.C. 154(b) by 379 days.

(21) Appl. No.: 16/917,226

(22) Filed: Jun. 30, 2020

(65) Prior Publication Data

US 2020/0330142 A1 Oct. 22, 2020

Related U.S. Application Data

(63) Continuation of application No. 16/033,029, filed on Jul. 11, 2018, now Pat. No. 10,888,363.

(60) Provisional application No. 62/595,217, filed on Dec. 6, 2017.

(51) Int. Cl.
*A61B 17/86* (2006.01)
*A61B 17/70* (2006.01)
*A61B 17/88* (2006.01)
*A61B 90/00* (2016.01)
*A61B 17/00* (2006.01)

(52) U.S. Cl.
CPC ...... *A61B 17/8625* (2013.01); *A61B 17/7032* (2013.01); *A61B 17/7098* (2013.01); *A61B 17/864* (2013.01); *A61B 17/8605* (2013.01); *A61B 17/8635* (2013.01); *A61B 17/8811* (2013.01); *A61B 17/8685* (2013.01); *A61B 2017/00004* (2013.01); *A61B 2017/8655* (2013.01); *A61B 2090/037* (2016.02)

(58) Field of Classification Search
CPC ............ A61B 17/7098; A61B 17/8811; A61B 17/8635; A61B 17/8685; A61B 2017/8655; A61B 17/8625; A61B 17/8605; A61B 17/864; A61B 17/7032
See application file for complete search history.

(56) References Cited

U.S. PATENT DOCUMENTS

| | | | |
|---|---|---|---|
| 1,394,925 A | 10/1921 | Marshall | |
| 1,438,648 A | 12/1922 | Jacobs | |
| 2,121,193 A | 6/1938 | Hanicke | |
| 4,269,106 A | 5/1981 | Leibhard et al. | |
| 4,456,005 A | 6/1984 | Lichty | |

(Continued)

FOREIGN PATENT DOCUMENTS

| | | |
|---|---|---|
| EP | 0129442 | 12/1984 |
| EP | 0574707 | 12/1993 |

(Continued)

OTHER PUBLICATIONS

U.S. Appl. No. 12/556,820, filed Sep. 10, 2009.
U.S. Appl. No. 16/560,064, filed Sep. 4, 2019.
U.S. Appl. No. 10/342,008, filed Jan. 14, 2003.
U.S. Appl. No. 12/264,181, filed Nov. 3, 2008.
U.S. Appl. No. 16/033,029, filed Jul. 11, 2018.
U.S. Appl. No. 16/510,608, filed Jul. 12, 2019.

(Continued)

*Primary Examiner* — Eduardo C Robert
*Assistant Examiner* — Tara Rose E Carter
(74) *Attorney, Agent, or Firm* — Levine Bagade Han LLP

(57) ABSTRACT

Attachment devices and methods of using the same are disclosed. The attachment devices can be fenestrated. The fenestrations can control the flow of fluid out of and/or into the device.

15 Claims, 39 Drawing Sheets

(56) References Cited

U.S. PATENT DOCUMENTS

| | | |
|---|---|---|
| 4,738,255 A | 4/1988 | Goble et al. |
| 5,037,422 A | 8/1991 | Hayhurst et al. |
| 5,046,513 A | 9/1991 | Gatturna et al. |
| 5,059,193 A | 10/1991 | Kuslich |
| 5,065,490 A | 11/1991 | Wivagg et al. |
| 5,207,679 A | 5/1993 | Li |
| 5,209,753 A | 5/1993 | Biedermann et al. |
| 5,221,261 A | 6/1993 | Termin et al. |
| 5,236,445 A | 8/1993 | Hayhurst et al. |
| 5,261,909 A | 11/1993 | Sutterlin et al. |
| 5,360,431 A | 11/1994 | Puno et al. |
| 5,390,683 A | 2/1995 | Pisharodi |
| 5,411,522 A | 5/1995 | Trott |
| 5,472,452 A | 12/1995 | Trott |
| 5,474,555 A | 12/1995 | Puno et al. |
| 5,480,403 A | 1/1996 | Lee et al. |
| 5,489,210 A | 2/1996 | Hanosh |
| 5,498,265 A | 3/1996 | Asnis et al. |
| 5,501,695 A | 3/1996 | Anspach et al. |
| 5,522,844 A | 6/1996 | Johnson |
| 5,643,321 A | 7/1997 | Mcdevitt |
| 5,649,950 A | 7/1997 | Bourne et al. |
| 5,662,654 A | 9/1997 | Thompson |
| 5,709,708 A | 1/1998 | Thal |
| 5,749,883 A | 5/1998 | Halpern |
| 5,749,899 A | 5/1998 | Bardin |
| 5,782,866 A | 7/1998 | Wenstrom |
| 5,797,963 A | 8/1998 | Mcdevitt |
| 5,824,011 A | 10/1998 | Stone et al. |
| 5,849,004 A | 12/1998 | Bramlet |
| 5,868,708 A | 2/1999 | Hart et al. |
| 5,882,350 A | 3/1999 | Ralph et al. |
| 5,935,129 A | 8/1999 | Mcdevitt et al. |
| 6,048,343 A | 4/2000 | Mathis et al. |
| 6,146,406 A | 11/2000 | Shluzas et al. |
| 6,168,597 B1 | 1/2001 | Biedermann et al. |
| 6,200,330 B1 | 3/2001 | Benderev et al. |
| 6,210,376 B1 | 4/2001 | Grayson |
| 6,214,012 B1 | 4/2001 | Karpman et al. |
| 6,224,600 B1 | 5/2001 | Protogirou |
| 6,224,625 B1 | 5/2001 | Jayaraman |
| 6,319,255 B1 | 11/2001 | Grundei et al. |
| 6,458,100 B2 | 10/2002 | Roue et al. |
| 6,506,051 B2 | 1/2003 | Levisman |
| 6,585,770 B1 | 7/2003 | White et al. |
| 6,602,034 B2 | 8/2003 | Wakai et al. |
| 6,626,861 B1 | 9/2003 | Hart et al. |
| 6,648,893 B2 | 11/2003 | Dudasik |
| 6,652,561 B1 | 11/2003 | Tran |
| 6,668,688 B2 | 12/2003 | Zhao et al. |
| 6,676,665 B2 | 1/2004 | Foley et al. |
| 6,719,509 B1 | 4/2004 | Huang et al. |
| 7,097,648 B1 | 8/2006 | Globerman et al. |
| 7,250,055 B1 | 7/2007 | Vanderwalle |
| 7,608,062 B2 | 10/2009 | Sweeney |
| 7,608,097 B2 | 10/2009 | Kyle |
| 8,092,504 B2 | 1/2012 | Warnick |
| 8,231,632 B1 | 7/2012 | Jordan et al. |
| 8,460,305 B2 | 6/2013 | Jordan et al. |
| 8,574,273 B2 | 11/2013 | Russell et al. |
| 8,608,802 B2 | 12/2013 | Bagga et al. |
| 8,636,784 B2 | 1/2014 | Greenhalgh et al. |
| 8,795,362 B2 | 8/2014 | Anderson et al. |
| 8,906,022 B2 | 12/2014 | Krinke et al. |
| 9,095,390 B2 | 8/2015 | Wallenstein et al. |
| 9,681,905 B2 | 6/2017 | Reimels |
| 10,888,363 B2 | 1/2021 | Greenhalgh et al. |
| 2001/0021852 A1 | 9/2001 | Chappius |
| 2002/0049447 A1 | 4/2002 | Li |
| 2002/0058947 A1* | 5/2002 | Hochschuler ......... A61F 2/4601 606/94 |
| 2002/0077520 A1 | 6/2002 | Segal et al. |
| 2002/0165544 A1 | 11/2002 | Perren et al. |
| 2002/0198527 A1 | 12/2002 | Muckter |
| 2004/0015172 A1 | 1/2004 | Biedermann et al. |
| 2004/0116992 A1 | 6/2004 | Wardle et al. |
| 2004/0133204 A1 | 7/2004 | Davies |
| 2004/0138707 A1 | 7/2004 | Greenhalgh |
| 2004/0167625 A1 | 8/2004 | Beyar et al. |
| 2004/0181234 A1 | 9/2004 | McDevitt et al. |
| 2004/0267254 A1 | 12/2004 | Manzo et al. |
| 2004/0267265 A1 | 12/2004 | Kyle |
| 2005/0065526 A1 | 3/2005 | Drew et al. |
| 2005/0113919 A1 | 5/2005 | Cragg et al. |
| 2005/0143827 A1 | 6/2005 | Globerman et al. |
| 2005/0187555 A1 | 8/2005 | Biedermann et al. |
| 2005/0228391 A1 | 10/2005 | Levy et al. |
| 2005/0261781 A1 | 11/2005 | Sennett et al. |
| 2005/0277966 A1 | 12/2005 | Ewers et al. |
| 2006/0015104 A1 | 1/2006 | Dalton |
| 2006/0052788 A1 | 3/2006 | Thelen et al. |
| 2006/0084987 A1 | 4/2006 | Kim |
| 2006/0190090 A1 | 8/2006 | Plaskon |
| 2006/0206208 A1 | 9/2006 | Michelson |
| 2006/0224241 A1 | 10/2006 | Butler et al. |
| 2006/0235391 A1 | 10/2006 | Sutterlin |
| 2006/0264950 A1 | 11/2006 | Nelson et al. |
| 2006/0271061 A1 | 11/2006 | Beyar et al. |
| 2007/0032791 A1 | 2/2007 | Greenhalgh |
| 2007/0093899 A1 | 4/2007 | Dutoit et al. |
| 2007/0106383 A1 | 5/2007 | Abdou |
| 2007/0161985 A1 | 7/2007 | Demakas et al. |
| 2007/0173939 A1 | 7/2007 | Kim et al. |
| 2007/0198018 A1 | 8/2007 | Biedermann et al. |
| 2007/0213732 A1 | 9/2007 | Khanna et al. |
| 2007/0270627 A1 | 11/2007 | Cutrer et al. |
| 2007/0282443 A1 | 12/2007 | Globerman et al. |
| 2008/0269749 A1 | 10/2008 | Shalaby et al. |
| 2008/0288003 A1 | 11/2008 | Mckinley |
| 2009/0125028 A1 | 5/2009 | Teisen et al. |
| 2009/0131992 A1 | 5/2009 | Greenhalgh et al. |
| 2009/0204158 A1 | 8/2009 | Sweeney |
| 2010/0016905 A1 | 1/2010 | Greenhalgh et al. |
| 2010/0030135 A1 | 2/2010 | Mitchell |
| 2010/0042215 A1* | 2/2010 | Stalcup ................ A61B 17/866 606/86 R |
| 2010/0100135 A1 | 4/2010 | Phan |
| 2010/0106199 A1 | 4/2010 | Sawa et al. |
| 2011/0015641 A1 | 1/2011 | Matsumoto |
| 2011/0060373 A1 | 3/2011 | Russell et al. |
| 2012/0029578 A1* | 2/2012 | Suh ...................... A61B 17/864 606/93 |
| 2014/0046379 A1* | 2/2014 | Sweeney .............. A61B 17/863 606/304 |
| 2014/0046381 A1 | 2/2014 | Asfora |
| 2014/0288651 A1 | 9/2014 | Biedermann et al. |
| 2015/0012051 A1 | 1/2015 | Warren et al. |
| 2015/0250513 A1 | 9/2015 | De Lavigne Sainte Suzanne |
| 2016/0213145 A1* | 7/2016 | Hientzsch .......... A61B 17/8635 |
| 2018/0071000 A1 | 3/2018 | Pham et al. |
| 2018/0368986 A1 | 12/2018 | Greenhalgh et al. |
| 2019/0167326 A1 | 6/2019 | Greenhalgh et al. |
| 2019/0374269 A1 | 12/2019 | Kiefer et al. |
| 2020/0015873 A1 | 1/2020 | Greenhalgh et al. |

FOREIGN PATENT DOCUMENTS

| | | |
|---|---|---|
| JP | 4-502567 | 5/1992 |
| JP | 11-504550 | 4/1999 |
| JP | 2003-513698 | 5/2001 |
| JP | 2002-514935 | 5/2002 |
| WO | WO 1995/025469 | 9/1995 |
| WO | WO 2000/044319 | 8/2000 |
| WO | WO 2000/044321 | 8/2000 |
| WO | WO 2000/044946 | 8/2000 |
| WO | WO 2001/034045 | 5/2001 |
| WO | WO 2001/054598 | 8/2001 |
| WO | WO 2003/003951 | 1/2003 |
| WO | WO 2003/047440 | 6/2003 |
| WO | WO 2004/004596 | 1/2004 |
| WO | WO 2005/034764 | 4/2005 |
| WO | WO 2005/096975 | 10/2005 |
| WO | WO 2006/034396 | 3/2006 |
| WO | WO 2006/034436 | 3/2006 |

(56) References Cited

FOREIGN PATENT DOCUMENTS

| WO | WO 2006/037013 | 4/2006 |
|---|---|---|
| WO | WO 2006/068682 | 6/2006 |
| WO | WO 2006/116760 | 11/2006 |
| WO | WO 2006/116761 | 11/2006 |
| WO | WO 2006/126979 | 11/2006 |
| WO | WO 2007/041665 | 4/2007 |
| WO | WO 2007/065137 | 6/2007 |
| WO | WO 2007/073488 | 6/2007 |
| WO | WO 2007/076374 | 7/2007 |
| WO | WO 2007/076377 | 7/2007 |
| WO | WO 2007/131002 | 11/2007 |
| WO | WO 2008/112308 | 9/2008 |
| WO | WO 2009/059227 | 5/2009 |
| WO | WO 2017/147537 | 8/2017 |
| WO | WO 2019/113095 | 6/2019 |
| WO | WO 2021/011313 | 1/2021 |

OTHER PUBLICATIONS

Franklin, I.J. et al., "Uptake of Tetracycline by Aortic Aneurysm Wall and Its Effect on Inflammation and Proteolysis," *Brit. J. Surger,* 86(6):771-775, Jun. 1999.

Pyo, R. et al., "Targeted Gene Disruption of Matrix Metalloproteinase-9 (Gelatinase B) Suppresses Development of Experimental Abdominal Aortic Aneurysms," *J. Clinical Investigation,* 105(11):1641-1649, Jun. 2000.

Tambiah, J. et al., "Provocation of Experimental Aortic Inflammation Mediators and Chlamydia Pneumoniae," *Brit., J. Surgery,* 88(7):935-940, Feb. 2001.

Walton, L.J. et al., "Inhibition of Prostoglandin E2 Synthesis in Abdonminal Aortic Aneurysms," *Circulation,* 48-54, Jul. 6, 1999.

Xu, Q. et al., "Sp1 Increases Expression of Cyclooxygenase-2 in Hypoxic Vascular Endothelium," *J. Biological Chemistry,* 275(32):24583-24589, Aug. 2000.

\* cited by examiner

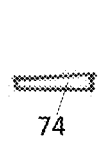
Figure 4G  Figure 4H  Figure 4I  Figure 4J
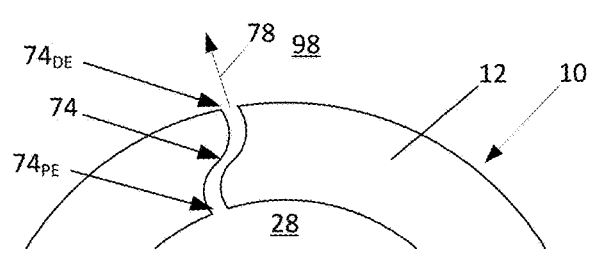
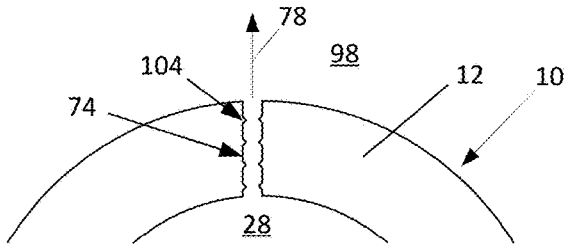
Figure 5  Figure 6A
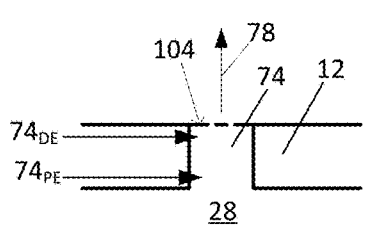
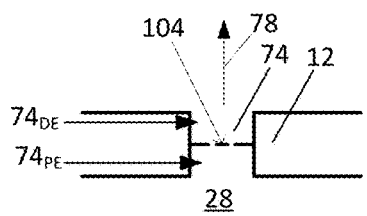
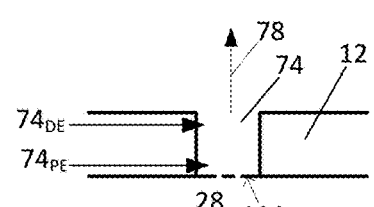
Figure 6B  Figure 6C  Figure 6D
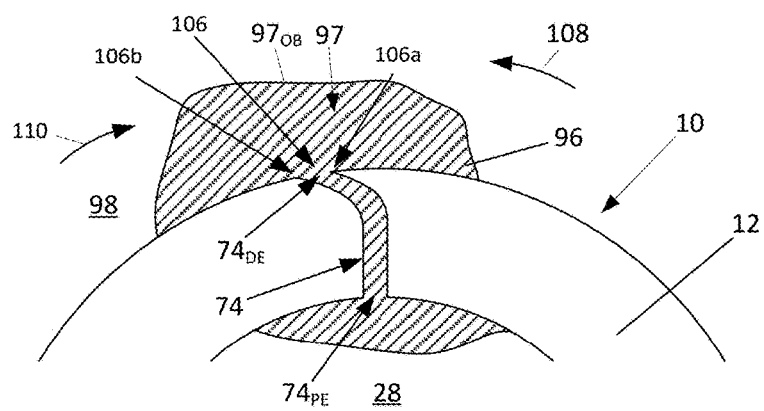
Figure 7

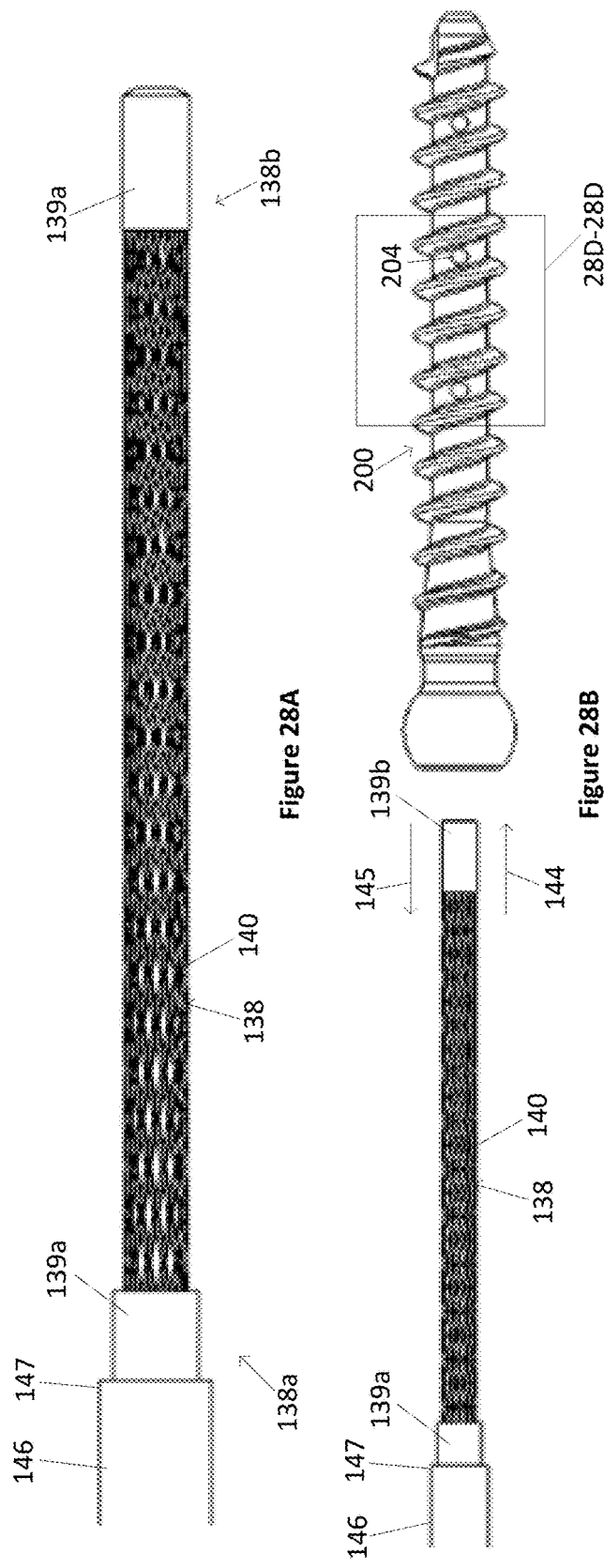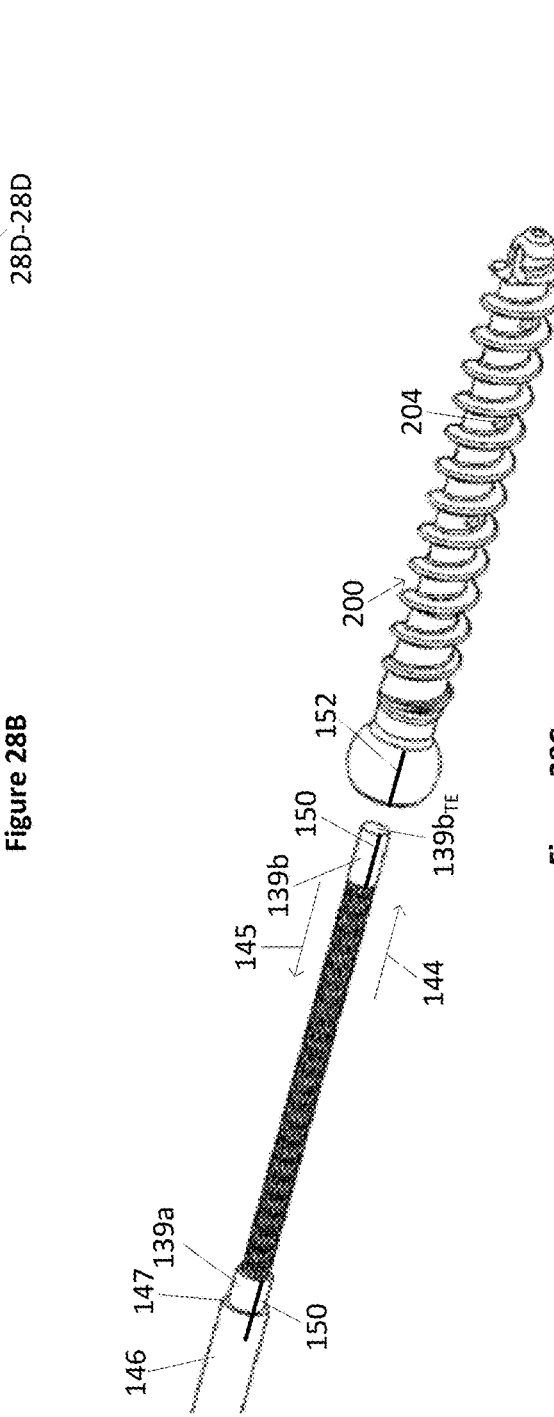
Figure 28A
Figure 28B
Figure 28C

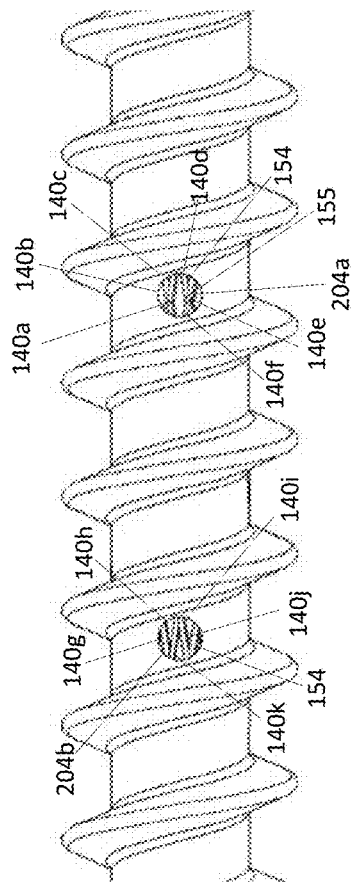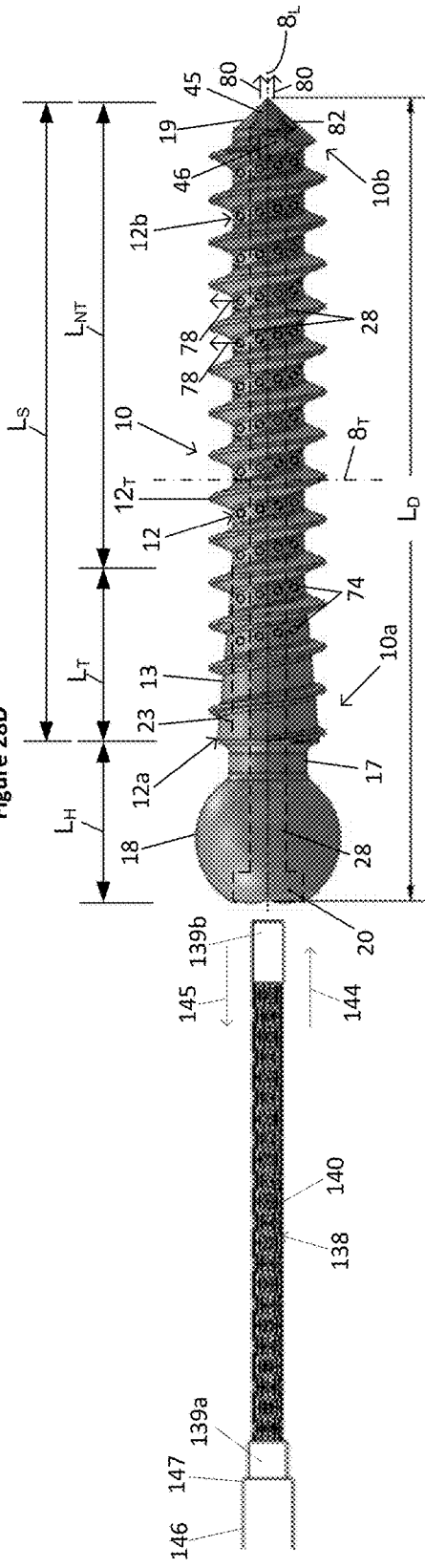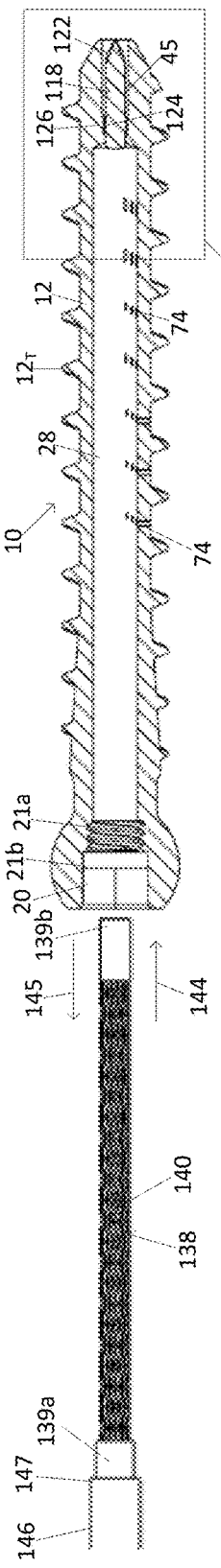
Figure 28D
Figure 28E
Figure 28F

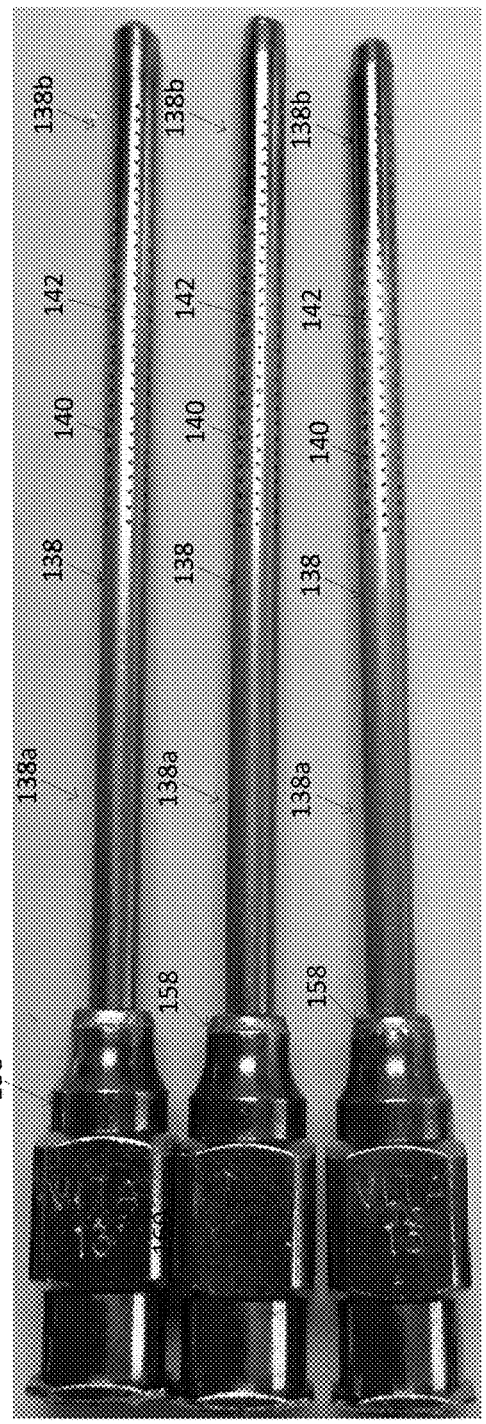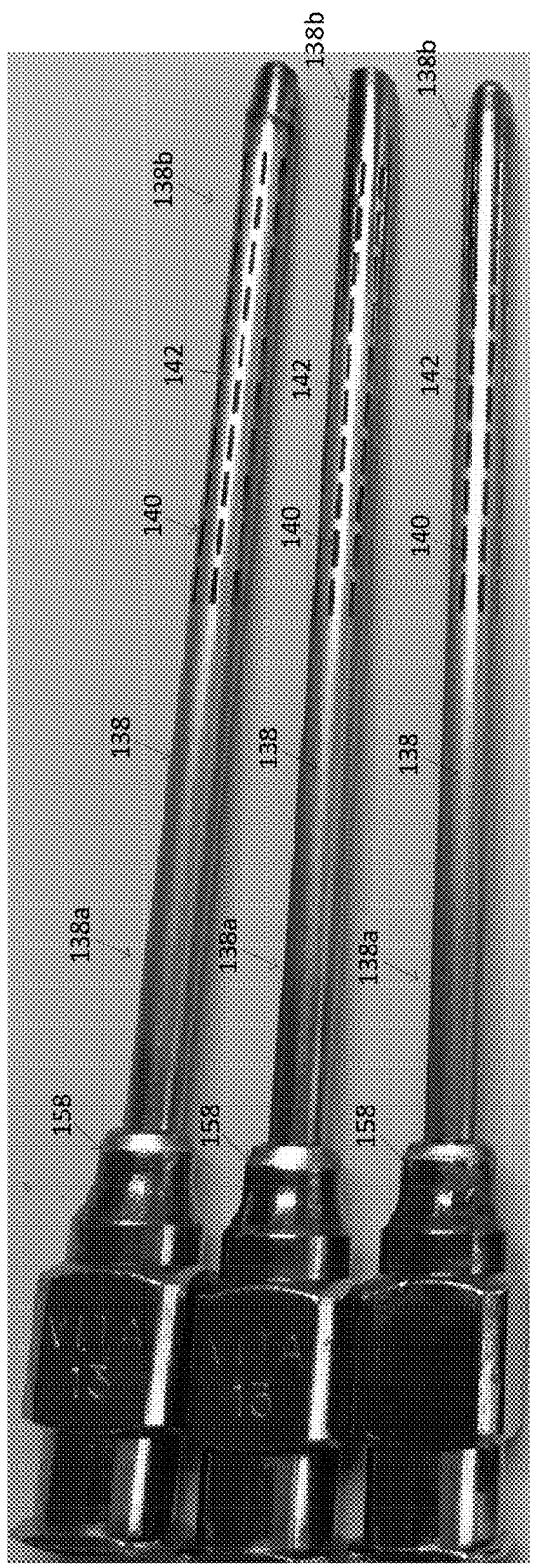
Figure 30A  Figure 30B  Figure 30C  Figure 31A  Figure 31B  Figure 31C

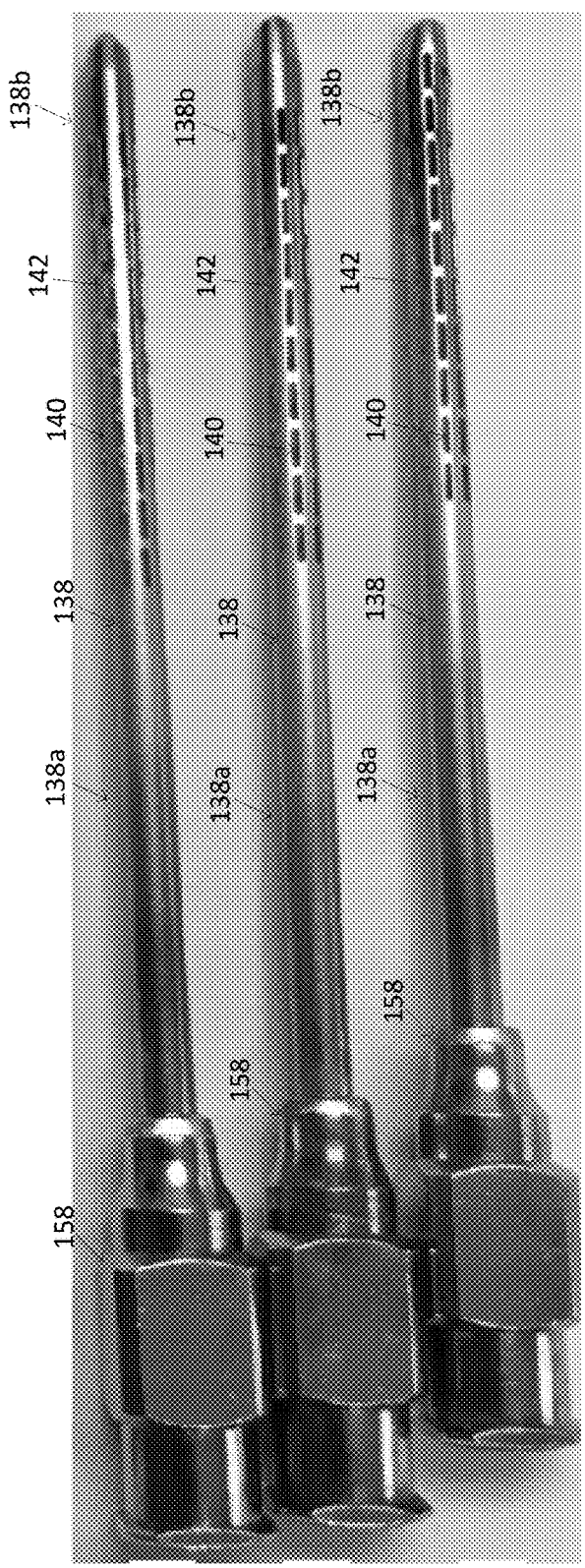

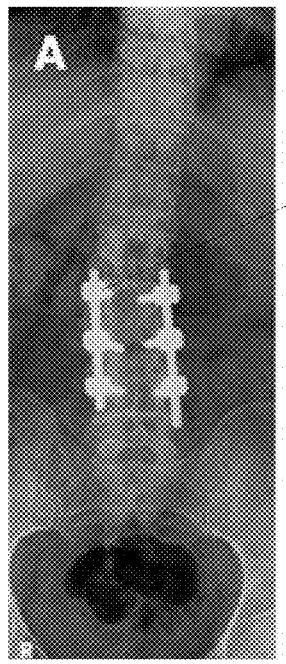
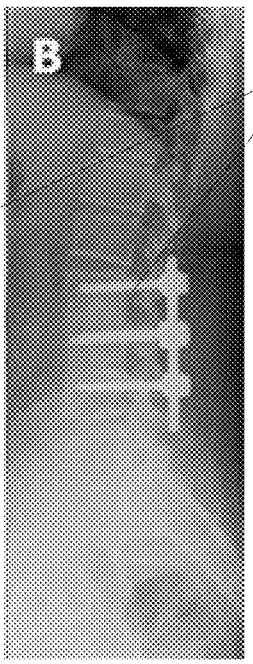
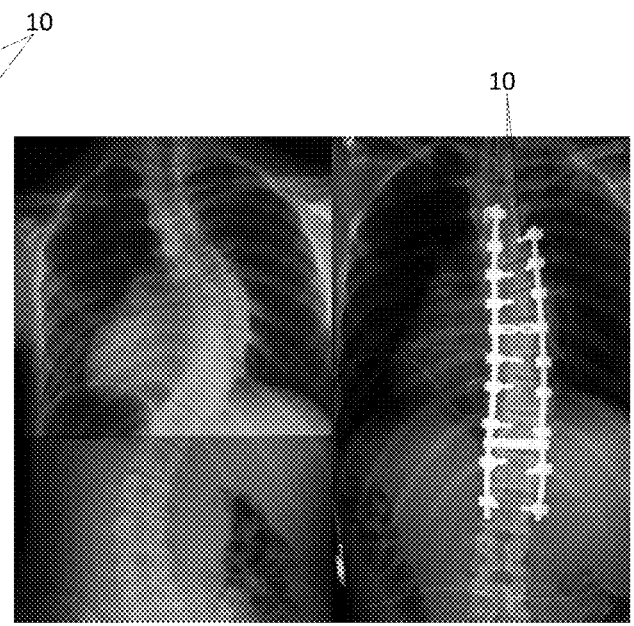
Figure 39A  Figure 39B  Figure 40A  Figure 40B
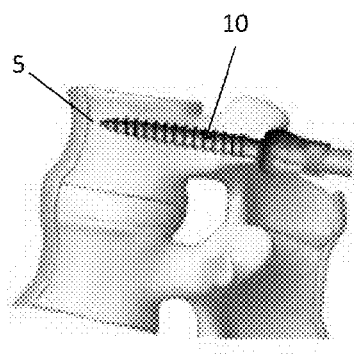
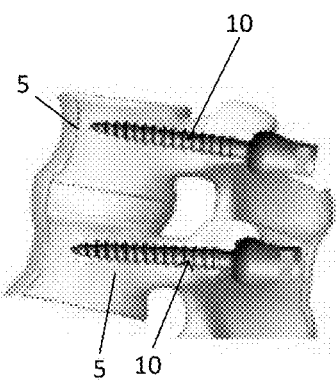
Figure 41A  Figure 41B

ATTACHMENT DEVICE AND METHOD FOR USE

CROSS-REFERENCE TO RELATED APPLICATIONS

This application is a continuation of U.S. patent application Ser. No. 16/033,029 filed Jul. 11, 2018, which claims the benefit of priority to U.S. Provisional Application No. 62/595,217 filed Dec. 6, 2017, each of which is incorporated herein by reference in its entirety for all purposes.

BACKGROUND

1. Technical Field

Attachment devices and methods of using the same are disclosed. More specifically, fenestrated attachment devices and fenestrated mufflers for use in bone and methods of using the same are disclosed.

2. Background of the Art

Broken bones, such as compression fractures of one or more vertebrae in the spine, may be treated with internal fixation. Any indication needed spinal stability can also be treated by internal fixation. Examples include scoliosis, kyphosis, spondylothisthesis and rotation, segmental instability, such as disc degeneration and fracture caused by disease and trauma and congenital defects, and degeneration caused by tumors.

Internal fixation in the spine is often accomplished by first screwing attachment devices into the pedicles and vertebral bodies of the vertebrae. The attachment devices are then typically attached to a rigid fixation rod or plate that provide support between one or more weakened vertebra. This support often immobilizes the vertebra to which the fixation screws have been inserted.

Fenestrated attachment devices are one type of attachment device that are currently used to stabilize bones in the spine. The fenestrations allow bone cement to be injected through the device and into surrounding bone to increase the anchor strength of the device. Such devices can be passive and used to stop bones from moving. In many cases such devices are used to shift or move bones into new positions. The active bone movement requires an attachment with dependably and predictably high anchor force and anchor strength. However, current fenestrated attachment devices have unpredictable anchoring strengths due to little or no control of the cement flow through the device during implantation. More predictable anchoring with cement can improve the outcomes in healthy and unhealthy bone alike, for example, in osteoporotic bone. Accordingly, a need currently exists to have fenestrated attachment devices with predictable and more reliable anchoring forces and strengths.

BRIEF SUMMARY

This disclosure relates generally to fenestrated attachment devices and to fenestrated mufflers.

More specifically, fenestrated attachment devices and fenestrated mufflers for use in bone and methods of using the same are disclosed.

Methods for implanting attachment devices are disclosed. For example, a method is disclosed for implanting an anatomical attachment device. The method can include inserting the anatomical attachment device at least partially into a bone at a target site. The attachment device can have an attachment device lumen and an attachment device first fenestration in fluid communication with the attachment device lumen and the target site. A pressure reduction device can be in the attachment device lumen. The pressure reduction device can have a pressure reduction first fenestration. The method can include pressurizing a bone cement into the attachment device lumen. The pressurizing can include flowing bone cement through the attachment device lumen, then flowing the bone cement through the pressure reduction device first fenestration, then flowing the bone cement through the attachment device first fenestration, then flowing the bone cement into the target site. The pressure of the bone cement can decrease when the bone cement passes through the pressure reduction first fenestration. The pressure reduction first fenestration can be on a lateral side of the pressure reduction device. The pressure reduction device can have a pressure reduction second fenestration on the lateral side of the pressure reduction device and at least 90° away from the pressure reduction first fenestration with respect to a longitudinal axis of the pressure reduction device.

Methods for implanting bone screws are disclosed. For example, a method is disclosed for implanting a bone screw. The method can include inserting the bone screw into a bone at a target site. The bone screw can have a helical thread, a bone screw lumen, and a bone screw first fenestration. A pressure reduction device can be fixedly attached to or integral with the bone screw. The pressure reduction device can be at least partially in the bone screw lumen. The pressure reduction device can have a pressure reduction first fenestration on a lateral side of the pressure reduction device.

Methods for implanting bone screws are disclosed. For example, a method is disclosed for implanting a bone screw. The method can include fixedly attaching or integrating a pressure reduction device to the distal end of a syringe. The pressure reduction device can have a lateral pressure reduction first fenestration. The method can include inserting the bone screw into a target site. The bone screw can have a bone screw lumen, and a bone screw lateral fenestration. The method can include inserting the pressure reduction device into the bone screw lumen. The inserting of the pressure reduction device can include positioning at least a portion of the syringe adjacent to the bone screw lumen. The method can include delivering a bone cement from the syringe, through the pressure reduction device in the bone screw lumen, and through the bone screw lateral fenestration.

BRIEF DESCRIPTION OF THE DRAWINGS

The drawings shown and described are exemplary embodiments and non-limiting. Like reference numerals indicate identical or functionally equivalent features throughout.

FIG. 4G illustrates a side view of a variation of a device fenestration.

FIG. 4H illustrates a side view of a variation of a device fenestration.

FIG. 4I illustrates a side view of a variation of a device fenestration.

FIG. 4J illustrates a side view of a variation of a device fenestration.

FIG. 5 illustrates a cross-sectional view of a variation an attachment device.

FIG. 6A illustrates a cross-sectional view of a variation an attachment device.

FIG. 6B illustrates a schematic of a variation an attachment device.

FIG. 6C illustrates a schematic of a variation an attachment device.

FIG. 6D illustrates a schematic of a variation an attachment device.

FIG. 7 illustrates a cross-sectional view of a variation an attachment device.

FIG. 28A illustrates a side view of a variation of a muffler.

FIG. 28B illustrates the muffler of FIG. 28A and a variation of an attachment device.

FIG. 28C illustrates a perspective view of a variation of the muffler and attachment device of FIG. 28B.

FIG. 28D is a cropped side view of the muffler and attachment device of FIGS. 28B and 28C with the muffler in the attachment device.

FIG. 28E illustrates the muffler of FIG. 28A and the attachment device of FIG. 1A.

FIG. 28F illustrates the muffler of FIG. 28A and the attachment device of FIG. 20E.

FIG. 30A-30C illustrate side views of variations of mufflers.

FIGS. 31A-31C illustrate side views of variations of mufflers.

FIGS. 32A-32C illustrate side views of variations of mufflers.

FIG. 39A illustrates a schematic image of multiple attachment devices inserted into bone.

FIG. 39B illustrates a schematic image of multiple attachment devices inserted into bone.

FIG. 40A illustrates a schematic image of a curved spine.

FIG. 40B illustrates a schematic image of multiple attachment devices inserted into the spin of FIG. 40A.

FIG. 41A illustrates a variation of an attachment device implanted in a vertebra.

FIG. 41B illustrates a variation of two attachment devices implanted in two different vertebrae, respectively.

DETAILED DESCRIPTION

Figure 1A:
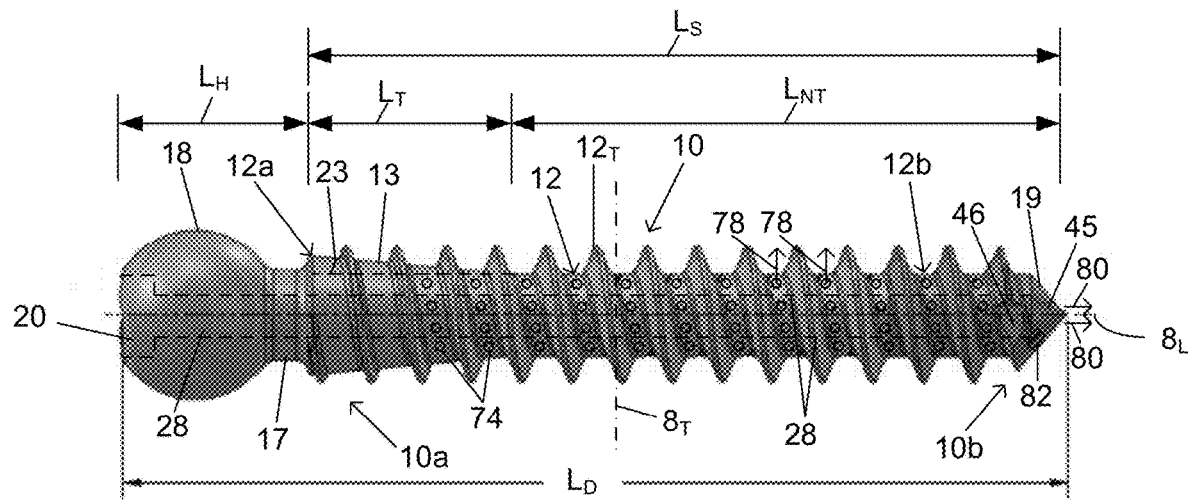
FIG. 1A illustrates a perspective view of a variation of an attachment device.

Fenestrated attachment devices and fenestrated mufflers are disclosed. The mufflers can be integrated with or attached to the disclosed devices. The devices can be a screw, for example, a pedicle screw. The mufflers can be a screw, for example, a pedicle screw. The mufflers can be removably or irremovably attached to the attachment devices. Fluid can be delivered through the attachment devices, through the fenestrated mufflers, or both.

System and Apparatus

FIG. 1 illustrates a variation of an attachment device 10 having a shaft 12. The device 10 can have a device proximal end 10a and a device distal end 10b. The shaft 12 can have a shaft proximal end 12a and a shaft distal end 12b. The device 10 (e.g., the shaft 12) can have fenestrations 74 (also referred to as device fenestrations) through which fluid can flow before, during, and/or after the device 10 is inserted into a medium. The medium can be tissue (e.g., bone). The device 10 can have a device longitudinal axis $8_L$ and a device transverse axis $8_T$. The device longitudinal axis $8_L$ can be a center longitudinal axis of the device 10 or can be a longitudinal axis offset from the center longitudinal axis. The device longitudinal axis $8_L$ can be straight or curved. The device longitudinal axis $8_L$ can be perpendicular to the device transverse axis $8_T$. The device transverse axis $8_T$ can be a center transverse axis of the device 10 or can be a transverse axis offset from the center transverse axis. The device transverse axis $8_T$ can be straight or curved.

The device 10 can be deformable and/or non-deformable. For example, the shaft 12 can be non-deformable. As another example, the shaft 12 can be deformable. The shaft 12 can be rigid, semi-rigid, flexible, or any combination thereof. The shaft 12 can be made of one or multiple materials. For example, the shaft 12 can be made from metal (e.g., titanium and/or steel), plastic, a composite material, or any combination thereof. The shaft 12 can form a frame of the device 10.

The device distal end 10b can have a tip 19. The tip 19 can be sharpened or otherwise configured to seat the device 10 in bone (e.g., with cutting teeth). The device proximal end 10a can have a proximal end cap 18. The cap 18 can have a substantially spherical configuration. A neck 17 can connect the cap 18 to the shaft 12. The cap 18, neck 17, and/or shaft 12 can be monolithically formed, integrated with one another, and/or attached to one another. The cap 18 can be removably or irremovably attached to the neck 17 or to the shaft 12. As another example, the device 10 can have the shaft 12 but no neck 17, no end cap 18, or no neck 17 and no end cap 18. The cap 18, neck 17, and/or tip 19 can be rigid, semi-rigid, deformable, non-deformable, flexible, or any combination thereof. The cap 18 can have a tool attachment port 20. As another example, the shaft 12 can have the tool first attachment port 20. An attachment tool (not shown) can be configured to engage with the tool attachment port 20 to deploy the device 10.

The tip 19 can have an anterior cortical purchase (not shown, also referred to as a spike) to increase the toggle strength of the device 10. The spike can help the tip 19 cut into bone. The device 10 can be a bi-cortical support with no threads on the distal end of the shaft 12.

The device 10 can have threads $12_T$ that can be screwed into bone. For example, the shaft 12 can have the threads $12_T$. The threads $12_T$ can be integrated with or attached to the shaft 12. The threads $12_T$ can extend at least partially radially away from the device longitudinal axis $8_L$. The threads $12_T$ can be between the device proximal and distal ends 10a, 10b.

The threads $12_T$ can be deformable, non-deformable, rigid, flexible, bioabsorbable, non-bioabsorbable, or any combination thereof. For example, the threads $12_T$ can be rigid (e.g., not flex) when the device is moved in a longitudinal first direction and can be flexible (e.g., flex) when the device is moved in a longitudinal second direction different from the longitudinal first direction. As an example, the threads $12_T$ can bend in a first direction (e.g., toward the device distal end 10b) and resist bending in a second direction opposite the first direction (e.g., toward the device proximal end 10a). The first direction can be the insertion direction (e.g., into the bone) and the second direction can be the removal direction (e.g., out of the bone). This can allow the device 10 to be screwed into bone and then later pulled out of the bone if the device 10 is ever removed, where the threads $12_T$ can be bendable anywhere along their length (e.g., bendable at their base, or bendable anywhere between the thread base and thread tip) such that the tip of the threads $12_T$ can move toward the device distal end 10b when the device 10 is rotated and/or pulled from the bone. As another example, the threads $12_T$ can remain secured to the shaft 12 when the device 10 is rotated or pushed in a first direction into the bone and detach (e.g., break off) from the shaft 12 when the device 10 is rotated or pushed in a second direction opposite the first direction. This can allow for the device 10 to be more easily removed from the bone if removal is ever desired.

The device 10 can be made of bioabsorbable material, non-bioabsorbable material, or both. For example, the shaft 12 can be made of a non-bioabsorbable material, all or a portion of one or more of the threads $12_T$ can be made of a non-bioabsorbable material, all or a portion of one or more of the threads $12_T$ can be made of a bioabsorbable material, or any combination thereof. For example, the shaft 12 can be made of a non-bioabsorbable material and the threads $12_T$ can be made of a bioabsorbable material. Once the device 10 is implanted into a medium, the threads $12_T$ can be bioabsorbed. The threads $12_T$ can be bioabsorbed over a bioabsorption period ranging from, for example, 5 days to 90 days, including every 5 day range within this range and every 1 day increment within this range and sub-ranges. All or a portion of the threads $12_T$ can be bioabsorbed. For example, about 25% to about 100% the threads $12_T$ can be bioabsorbed over the bioabsorption period. Bioabsorption can reduce the thread height, for example, by about 25% to about 100%. Partial or complete bioabsorption of the threads can allow for the device 10 to be more easily removed from the bone if removal is ever desired. Partial or complete bioabsorption of the threads can promote bone growth around the device 10 and into anchoring fluid around the device 10. The threads $12_T$ can be made from the same or different material as the shaft 12. The shaft 12 can be made from the same or different material as the threads $12_T$.

The threads $12_T$ can have a thread pitch, for example, from about 0.25 mm to about 7.5 mm, including every 0.25 mm increment within this range, for example 1.0 mm. The threads $12_T$ can have a high thread pitch, for example, 5.0 mm. The threads $12_T$ can have a thread helix angle, for example, from about 1 degree to about 75 degrees, including every 1 degree increment within this range, for example 20 degrees, 45 degrees. The threads $12_T$ can have a high thread pitch, for example, 5.0 mm. The threads $12_T$ can have a uniform or non-uniform thread diameter along the length of the device 10. The threads $12_T$ can have a uniform or non-uniform thread depth along the length of the device 10. For example, FIG. 1 illustrates that the thread depth can decrease along a length of the device 10, for example where the device 10 has a taper 13 (also referred to as a tapered portion).

The threads $12_T$ can have one or more cutting flutes 46 (also referred to as screw removal cutting flutes) to aid in the removal of the device 10 from bone. The cutting flutes 46 can cut bone when the device 10 is removed from bone (e.g., rotated the opposite direction from the insertion rotation direction). The threads $12_T$ can have 1 to 20 cutting flutes 46, including every 1 cutting flute increment within this range, for example, 1 cutting flute, 2 cutting flutes. For example, the threads $12_T$ can have a cutting flute about every 30 degrees to about every 360 degrees along the thread helix, including every 15 degree increment within this range. As another example, the device 10 can have a first cutting flute 46 on the device proximal end 10a and a second cutting flute on the device distal end 10b.

One or more portions of the device 10 can have a taper. For example, FIG. 1A illustrates that the device proximal end 10a can have the taper 13. The thread diameter along the length of the tapered section 13 can remain constant as shown in FIG. 1A, or can increase or decrease. The taper 13 can be configured to strengthen the attachment of the device 10 into bone by imparting a radial force onto the bone. This radial force can create compression that can be configured to prevent the device 10 from loosening once secured (e.g., screwed) into bone. This radial force can help create an interference fit (also referred to as a friction fit) that can be configured to prevent the device 10 from loosening from bone once secured (e.g., screwed) to it. The taper 13 can have a taper angle 23 from about 1 degree to about 45 degrees, including every 1 degree increment within this range, for example, about 10 degrees.

FIG. 1A further illustrates that the device 10 can be cannulated. For example, the device 10 can have a device channel 28. The device channel 28 can be centered or offset relative to the device longitudinal axis $8_L$. The device channel 28 can be non-tapered, tapered, or both. The device channel 28 can be straight, curved, or both. The device channel 28 can have a tubular shape, for example, a cylindrical shape. The cylindrical shape can be straight, curved, or have multiple path segments such that the device channel 28 defines a mono-directional path allowing bi-directional fluid flow or poly-directional paths (e.g., two or more straight and/or curved paths, for example, a zig-zag) allowing bi-directional fluid flow. Bi-directional flow can include flow through the device channel 28 toward the device distal end 10a and flow through the device channel 28 toward the device proximal end 10a. The device channel 28 can have a conical shape, including conical, truncated-conical, or frusto-conical. The device channel 28 can have a polyhedral shape, including polyhedral, truncated-polyhedral, or frusto-polyhedral. The device channel 28 can have a pyramidal shape, including pyramidal, truncated-pyramidal, or frusto-pyramidal. The device channel 28 can have multiple channel segments having any of the shapes disclosed and contemplated herein. For example, a device channel first section can have the same or different shape as a device channel second section.

The device channel 28 can extend longitudinally through the shaft 12, through the neck 17, through the end cap 18, or any combination thereof. The device channel 28 can be configured to receive or otherwise engage with one or multiple attachment tools, anchoring fluid, or both. The device channel 28 can terminate at the tool attachment port 20. As another example, the proximal end of the device channel 28 can be the tool attachment port 20. The tool attachment port 20 can be configured to receive or otherwise engage with one or multiple attachment tools, anchoring fluid, or both.

Figure 1B:
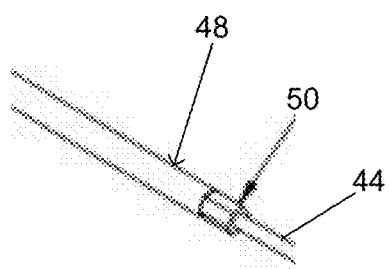
FIG. 1B illustrates a perspective view of a variation of an attachment tool.

The attachment tool can be configured to engage with the tool attachment port 20 to deploy the device 10 into a first deployed position in bone. The attachment tool can push and/or rotate the shaft 12, for example, to screw the device 10 into bone into the first deployed position. For example, a first attachment tool can be removably engaged with the tool attachment port 20. When the first attachment tool is removably engaged with the tool attachment port 20, the first attachment tool can be rotated and/or pushed to insert (e.g., screw) the device 10 into bone. When the first attachment tool is attached to the tool attachment port 20, the first attachment tool or a second attachment tool can inject fluid into the device channel 28. The second attachment tool can fit over or within the first attachment tool. The device channel 28 can be configured to receive or otherwise engage with a muffler. The tool attachment port 20 can be configured to receive or otherwise engage with a muffler. Fluid can flow through the device channel 28, the tool attachment port 20, the muffler, or both. The tool attachment port 20 can have a curved and/or polygonal transverse cross-sectional shape, for example, a hexagonal shape. An attachment tool can have a shape that matches the shape of the tool attachment port 20. The device channel 28 can have a curved or polygonal transverse cross-sectional shape, for example, circular, elliptical, hexagonal. For example, FIG. 1B illustrates that the system can have an attachment tool 48 removably attachable to the device 10. The attachment tool 48 can have a distal end having a driver 50 configured to engage with the attachment port 20. The driver 50 can be a radial driver and/or a longitudinal driver. The driver 50 can be rotatable, translatable, or both. The attachment tool 48 can removably receive a bone needle 44. The bone needle 44 can extend though the device 10. The radial driver 50 can be configured to engage with the tool attachment port 20 to push or screw the device 10 into bone.

FIG. 1 further illustrates that the device 10 can have a device head length $L_H$, a device shaft length $L_S$, and a device length $L_D$. The head length $L_H$ can be the length of the portion of the device proximal to the shaft 12. For example, the head length $L_H$ can be the length of the cap 18 and/or the neck 17. The head length $L_H$ can be about 5 mm to about 15 mm, including every 0.5 mm increment within this range, for example, about 8 mm. The device shaft length $L_S$ can be the length of the portion of the device distal to the neck 17 or cap 18. The device shaft length $L_S$ can be the length of the shaft 12 with or without the length of the tip 19. For example, the device shaft length $L_S$ can be the length of the shaft 12 with the tip 19. The device shaft length $L_S$ can be about 20 mm to about 100 mm, including every 0.5 mm increment within this range, for example, about 15 mm, about 25 mm, about 35 mm, about 50 mm. The device length $L_D$ can be the sum of the device head length $L_H$ and the device shaft length $L_S$. For example, the device length can be about 20 mm to about 100 mm, including every 0.5 mm increment within this range, for example, about 15 mm, about 25 mm, about 35 mm, about 50 mm. The shaft 12 can be tapered, non-tapered, or both along the shaft length $L_S$. For example, FIG. 1A illustrates that the shaft length Ls can have a tapered portion 13 having a longitudinal length $L_T$ and a non-tapered portion $12_{NT}$ having a non-tapered longitudinal length $L_{NT}$. The tapered and non-tapered longitudinal lengths $L_T$, $L_{NT}$ can extend along the device longitudinal axis $8_L$. The tapered portion 13 can extend partially or entirely along the shaft length $L_S$. The taper 13 can have a taper length $L_T$ of about 5 mm to about 100 mm, including every 0.5 mm increment within this range, for example, about 10 mm, about 20 mm, about 30 mm, about 40 mm, about 80 mm. The non-tapered longitudinal length $L_{NT}$ can be about 5 mm to about 100 mm, including every 0.5 mm increment within this range, for example, about 20 mm, about 25 mm, about 30 mm, about 40 mm, about 80 mm.

FIG. 1A further illustrates that the device 10 can have one or more fenestrations 74 (also referred to as device fenestrations, holes, device holes). For example, the FIG. 1A illustrates that the shaft 12 can have the fenestrations 74. The tip 19 can have one or multiple of the fenestrations 74. The fenestrations 74 can allow bone to grow into the device 10 to help anchor the device 10, can allow anchoring fluid (e.g., bone cement) to flow through the device 10 and into surrounding bone to help anchor the device 10, or both. Bone can grow and/or rebound into the fenestrations 74. Fluid can be delivered and/or withdrawn through the fenestrations 74. For example, bone cement can be injected through the fenestrations 74 into surrounding bone and/or into an external space created by the device 10 (e.g., between threads), for example, through one or multiple shaft channels (e.g., shaft channel 28) and then in and through the fenestrations 74. One or more of the fenestrations 74 can be holes for anchoring fluid (such fenestrations also referred to as anchoring fluid fenestrations). One or more of the fenestrations 74 can be holes for bone (such fenestrations are also referred to as bone fenestrations). For example, a set of first fenestrations 74 can be for bone growth and a set of second fenestrations 74 can be for anchoring fluid. In such variations bone can grow into the first set of fenestrations 74 (also referred to as bone growth fenestrations) and fluid can flow through the second set of fenestrations (also referred to as fluid fenestrations). The device 10 can have external grooves to provide space for bone growth, to provide space for bone to rebound into, to provide space for anchoring fluid to flow into once it flows out of the device 10, or any combination thereof.

The device 10 can have 1 to 150 or more fenestrations 74, including every 1 hole increment within this range, for example, 56 fenestrations 74. The shaft 12 of the device 10 can have one or multiple holes 74. The holes 74 can extend through the shaft 12. The holes 74 can extend through the threads (e.g., threads $12_T$). Any portion of the shaft 12 can have one or more fenestrations 74, for example, including the threads (e.g., $12_T$), between the threads $12_T$ (e.g., between adjacent threads), the tip 19, or any combination thereof. The fenestrations 74 can be laser cut into the shaft 12.

The fenestrations 74 can extend toward an outer surface of the device 10, toward an outer surface of the shaft 12, toward an inner surface of the shaft 12, or any combination thereof. Each fenestration 74 can define a fenestration path. Each fenestration 74 can be separate from some or all of the other fenestrations 74. As another example, two or more of the fenestrations 74 can be connected to each other with a connecting channel. The connecting channel can be or can be part of another fenestration 74. The connecting channel can be in the wall of the shaft 12, in the threads $12_T$, or both. The fenestrations 74 can have one or more inlets and one or more outlets, for example, one inlet and one outlet, one inlet and two outlets, or two inlets and one outlet. A fenestration 74 can have, for example, 1 to 10 or more inlets, including every 1 inlet increment within this range and can have, for example, 1 to 10 or more outlets, including every 1 outlet increment within this range. A fenestration 74 can have every inlet-outlet number combination. The inlets can be on an interior of the device 10 and the outlets can be on an exterior of the device 10. For example, each fenestration 74 can have an inlet opening and an outlet opening. The inlet opening can open along the exterior of the shaft 12. The outlet opening can fluidically connect the fenestration 74 to the exterior of the device 10, for example, to bone. The outlet opening can open along the interior of the shaft 12. The inlet opening can fluidically connect the fenestration 74 to an interior of the device, for example, to the shaft channel 28. If the direction of fluid flow is reversed, the inlets and outlets described above can be outlets and inlets, respectively.

The fenestration path can be curved, straight, include polyline paths (e.g., two or more straight and/or curved paths, for example, a zig-zag), or any combination thereof. The fenestration path can be multiple paths, for example, a network of open cells such that the cells form smaller openings within the fenestrations 74. The cells can form mesh-like openings in the fenestrations 74. The cells can be formed by a mesh attached to or integrated with the fenestrations 74. The mesh can extend partially or entirely across a cross-sectional area of the fenestrations 74. The connecting channel can be curved, straight, include polyline paths (e.g., two or more straight and/or curved paths, for example, a zig-zag), or any combination thereof.

The fenestrations 74 can have a tubular shape, for example, a cylindrical shape. The cylindrical shape can be straight, curved, or have multiple path segments such that the fenestrations 74 define mono-directional paths or polydirectional paths (e.g., two or more straight and/or curved paths, for example, a zig-zag). The fenestration paths can be tapered, non-tapered, or both. The fenestrations 74 can have a conical shape, including conical, truncated-conical, or frusto-conical. The fenestrations 74 can have a polyhedral shape, including polyhedral, truncated-polyhedral, or frusto-polyhedral. The fenestrations 74 can have a pyramidal shape, including pyramidal, truncated-pyramidal, or frusto-pyramidal. The fenestrations 74 can have the same or different shapes relative to one another. For example, a first fenestration 74 can have the same or different shape than a second fenestration 74.

The fenestrations 74 can be openings distributed along the shaft 12 along the device longitudinal axis $8_L$. For example, the fenestrations 74 can be elongated slots running down the axis of the device 10 or following the screw thread and/or screw pitch of the device 10 when the device 10 is a screw. For example, the fenestrations 74 can be arranged in a helical pattern along the threads $12_T$, along the space between the threads $12_T$, or both.

The fenestrations 74 can have a transverse component, a longitudinal component, or both, for example, relative to the device longitudinal axis $8_L$, the device transverse axis $8_T$, or both. The fenestrations 74 can extend entirely in a longitudinal direction, for example, relative to the device longitudinal axis $8_L$. The fenestrations 74 can extend at least partially in a longitudinal direction, for example, relative to the device longitudinal axis $8_L$. The fenestrations 74 can extend entirely in a transverse direction, for example, relative to the device transverse axis $8_T$. The fenestrations 74 can extend at least partially in a transverse direction, for example, relative to the device transverse axis $8_T$. For example, FIG. 1A illustrates that the fenestrations 74 can extend radially outward relative to the device longitudinal axis $8_L$, for example, along the device transverse axis $8_T$.

The fenestrations 74 can have slot, circular, elliptical, polygonal (e.g., diamond-shaped, star-shaped), and irregular-shaped cross-sections, or any combination thereof. For example, for fenestrations 74 having a slot shape, the slots can have stadium-shaped cross-sections, rectangular-shaped cross-sections, triangular-shaped cross-sections, diamond-shaped cross-sections, oval-shaped cross-sections, elliptical-shaped cross-sections, or any combination thereof. The fenestrations 74 can have one or multiple cross-sectional shapes.

The fenestrations 74 can have a constant cross-sectional area. The fenestrations 74 can be tapered such that the cross-sectional area of the fenestrations 74 increases or decreases along a length of the fenestrations 74. For example, the cross-sectional area of the fenestrations 74 can taper from a fenestration first cross-sectional area to a fenestration second cross-sectional area along the length of the fenestration path. The fenestration first cross-sectional area can be larger or smaller than the fenestration second cross-sectional area. The fenestration first cross-sectional area can be at a fenestration proximal end, for example, a proximal terminal end of the fenestration 74. The fenestration second cross-sectional area can be at a fenestration distal end, for example, a distal terminal end of the fenestration 74. The fenestration proximal terminal end of the fenestration can be closer to the device longitudinal axis $8_L$ than the fenestration distal terminal end. The fenestration proximal terminal end can abut the internal channel of the device 10 (e.g., channel 28). The fenestration proximal terminal end can connect the fenestration 74 to the internal channel of the device 10 (e.g., channel 28). The fenestrations 74 can have one or multiple tapered portions. The fenestration taper can have a constant taper, a step-wise taper, a progressively increasing or decreasing taper, or any combination thereof. The fenestrations 74 can have one or more tapered portions, one or more non-tapered portions, or any combination thereof.

The fenestrations 74 can have a maximum cross-sectional dimension of about 1.0 mm to about 5.0 mm or more, including every 0.1 mm increment within this range. The maximum cross-sectional dimension can be measured at the fenestration proximal end (e.g., at the fenestration proximal terminal end where the fenestration inlet is), at the fenestration distal end (e.g., at the fenestration distal terminal end where the fenestration outlet is), across the fenestration 74 at a location between the fenestration proximal and distal ends (e.g., at an intermediate region is between the proximal and distal ends), or any combination thereof. As another example, the fenestrations 74 can have a maximum cross-sectional area of about 1 mm² to about 25 mm² or more, including every 1 mm² increment within this range.

The fenestrations 74 on the distal end of the device 10 can be the same or different as the fenestrations 74 on the proximal end of the device 10. For example, the fenestrations 74 on the distal end of the device can have the same or different cross-sectional shape, the same or different taper or non-taper, the same or different size, or any combination thereof. For example, the fenestrations 74 on the distal end of the device 10 can have a constant cross-sectional area and the fenestrations 74 on the proximal end can define a tapered fenestration path, or vice versa.

The fenestrations 74 can advantageously allow bone cement to flow out of the device 10 (through one or more of the fenestrations 74) to secure the device 10 in place at the implant location. For example, after the device 10 is inserted into bone, bone cement can be injected through the device 10 (e.g., through the shaft 12) such that bone cement can flow out of the fenestrations 74 and fill the space surrounding the device 10, as indicated by bone cement flow arrows 78. Although only two arrows 78 are shown in FIG. 1A, arrows 78 indicating flow can emanate from any of the fenestrations 74 when fluid is forced through the device 10, for example, all of the fenestrations 74.

Bone cement can be injected into and/or through the channels of the device 10 that are within the shaft 12, for example, within and/or through the shaft channel 28, a bone needle channel 45, or both. The bone needle channel 45 can be in the tip 19. For example, FIG. 1A illustrates that bone cement can flow between the threads $12_T$, as indicated by bone cement flow arrows 78. FIG. 1A further illustrates that bone cement can flow out of the bone needle channel 45, as indicated by bone cement flow arrow 80.

The fenestrations 74 can have a size and shape that can provide fluid flow rates and fluid flow pressures that eliminate or inhibit unconstrained fluid flow into cracks and fissures in bone. The fenestrations 74 can have a size and shape so that a uniform flow field is created when fluid is injected through the device 10. The fenestrations 74 can have a size and shape so that a uniform flow field is created when fluid is forced through the device 10. The fluid can be anchoring fluid such as bone cement (e.g., polymethylmethacrylate (PMMA) bone cement). The fenestrations 74 can be arranged so that a uniform flow field is created when fluid is injected through the device 10. As another example, the fenestrations can be arranged so that a non-uniform flow field is created when fluid is injected through the device 10. The anchoring fluid (e.g., bone cement) can have one or multiple growth factors to encourage bone to grow into or around the implanted fluid.

The fenestrations 74 can provide resistance to flow through the device 10. The fenestrations 74 can provide uniform or non-uniform resistance to flow along the length of the device 10. The resistance can create a uniform flow field through the fenestrations 74 when fluid is injected through the device 10. For example, when the device 10 is implanted into nonhomogeneous bone (e.g., osteoporotic bone, bone having holes, bone having cracks) and fluid (e.g., anchoring fluid) is injected through the device 10, the fluid can flow through each hole 74 in a uniform manner (e.g., uniform flow rate, uniform flow pressure) such that the fenestrations 74 create uniform fluid flow along the length of the device 10.

The size and shape of the fenestrations 74 can control the flow of fluid through the device 10. The fenestrations can have a size and shape that provide a flow rate and a flow pressure when fluid is delivered through the fenestrations 74, for example, with a constant or variable delivery force. The flow rate can be constant, or can depend on the force at which fluid is injected into the device 10. The flow rate can be independent of the force and/or the flow rate at which fluid is injected into the device 10. The flow rate through all the fenestrations 74 can be the same for any given fluid delivery force into or applied to the device 10. The flow pressure can be constant, or can depend on the force at which fluid is injected into the device 10. The flow pressure through all the fenestrations 74 can be the same for any given fluid delivery force into the device 10.

The flow rate through the device 10 can be, for example, from about 0.25 cubic centimeters per second to about 3.00 cubic centimeters per second, or more narrowly, from about 0.80 cc/s to about 1.25 cc/s, including every 0.05 cc/s increment within these ranges (e.g., 0.50 cc/s, 0.80 cc/s, 1.00 cc/s, 1.25 cc/s). As another example, the flow rate through the device 10 can be, for example, from about 0.25 cc/min to about 3.00 cc/min, or more narrowly, from about 0.80 cc/min to about 1.25 cc/min, including every 0.05 cc/min increment within these ranges (e.g., 0.50 cc/min, 0.80 cc/min, 1.00 cc/min, 1.25 cc/min).

The flow rate through each of the fenestrations 74 (e.g., on a per fenestration basis) can be about 0.01 cc/s to about 0.50 cc/s, including every 0.01 cc/s increment within this range (e.g., 0.1 cc/s), or more narrowly, from about 0.005 cc/s to about 0.0250 cc/s, including every 0.001 cc/s increment within this range (e.g., 0.016 cc/s). Where the device 10 has fenestrations 74 with a single size, the fenestration flow rate can be determined by dividing the device flow rate by the number of fenestrations 74. For example, where the device 10 has 30 uniformly sized fenestrations 74 and the device flow rate is about 0.5 cc/s, the flow rate through each of the fenestrations 74 can be about 0.016 cc/s (e.g., 0.5 cc/s/30 fenestrations 74). Where the device 10 has fenestrations 74 of different sizes (e.g., two, three, four, five or more sizes), the flow rate through the differently sized fenestrations 74 can be the same or different from one another. For example, the fenestrations 74 of the device 10 can include a device first fenestration and a device second fenestration smaller than the device first fenestration. The device first fenestration can be proximal to the device second fenestration, distal to the device second fenestration, or even with the device second fenestration. The flow rate through the device first fenestration can be the same, larger than, or less than the flow rate through the device second fenestration. For example, the flow rate through the device first fenestration can be about 0.01 cc/s to about 0.50 cc/s, including every 0.01 cc/s increment within this range (e.g., 0.1 cc/s), or more narrowly, from about 0.005 cc/s to about 0.0250 cc/s, including every 0.001 cc/s increment within this range (e.g., 0.016 cc/s). The flow rate through the device second fenestration can be about 0.01 cc/s to about 0.50 cc/s, including every 0.01 cc/s increment within this range (e.g., 0.1 cc/s), or more narrowly, from about 0.005 cc/s to about 0.0250 cc/s, including every 0.001 cc/s increment within this range (e.g., 0.016 cc/s).

The fluid delivery pressure (also referred to as the flow pressure) can be, for example, from about 400 psi to about 2000 psi, including every 100 psi range within this range, including every 1 psi increment within these ranges, or any combination thereof (e.g., about 450 psi). For example, a 5 cc syringe can be capable of producing 450 psi of pressure. The fluid delivery pressure can be uniform through the fenestrations 74 or can depend on the size and shape of the fenestrations 74 where the device 10 has fenestrations 74 of different sizes. For example, the fluid delivery pressure through the device first fenestration can be the same, larger than, or less than the fluid delivery pressure through the device second fenestration.

The fenestrations 74, by providing a uniform resistance to flow exiting the device 10, can eliminate or reduce the effects of paths of less resistance in bone (e.g., areas having imperfections, compromised areas, weak areas, non-homogeneous areas, areas with cracks, areas with osteoporotic bone) so that the fluid can flow uniformly out of the device 10 through the fenestrations 74, so that the fluid flow out of any one of the fenestrations 74 (e.g., as measured by flow rate or flow pressure) does not exceed about 5% to about 100% of the fluid flow out of any other of the fenestrations 74, so that the fluid flow out of the fenestrations 74 (e.g., as measured by flow rate or flow pressure) is within a 5% to 20% tolerance of a target flow value associated with a given delivery force, or so that any combination of these three metrics for the flow of fluid out of the device 10 is satisfied or intentionally approximated. The percentage ranges in this paragraph can include any 1% increment within these ranges. The fenestrations 74 can control the flow out of and/or into the device 10.

The fenestrations 74 can create a uniform fluid region partially or entirely around the device 10 in homogeneous bone, non-homogeneous bone, or both. For devices where the fluid flow out of the device is not controlled, the flow rate out of some fenestrations 74 may be greater than other fenestrations 74 such that the fluid flows out of the device at a greater rate near paths of less resistance in the bone. The fenestrations 74 can be sized and shaped to prevent larger flow rates in or near paths of less resistance, for example, by limiting the flow rate and flow pressures through the fenestrations 74, thereby limiting the flow rate and flow pressures in bone regions having paths of less resistance.

The fenestrations 74 can advantageously allow fluid (e.g., anchoring fluid) to be injected in a central cannula of the device 10 with no or significantly less concern (e.g., as compared to conventional fluid augmentation attachment devices) about pressurized fluid from leaking out of the bone. The bone can be a vertebral body. The cannula can include the channel 28. Fenestrations 74 having a small size (e.g., having the dimensions described above) can provide significant resistance to flow of the fluid (e.g, viscous bone cement). This resistance, by design, can cause the fluid to weep from the surface of the device 10 out of the fenestrations 74 when fluid is forced through the device 10. This weeping effect does not allow for a path of least resistance to form if the bone is compromised with a crack or fissure. The fenestrations 74 can thereby inhibit or prevent the formation of flows having a flow rate or flow pressure that is dependent on the bone structure. For example, the fenestrations 74 can inhibit or prevent the formation of high flows or high flow regions (e.g., as compared to other flow regions) from developing as a result of internal bone geometry that is less resistant to fluid flow than surrounding areas. The fenestrations 74 can prevent or inhibit the formation of fluid paths of less resistance through the surrounding bone such that fluid flow through the device is dependent on the fenestrations 74, not on the internal bone geometry, or at least less dependent on the internal bone geometry, for example, as compared to conventional devices that do not have the fenestrations as described, contemplated, and/or illustrated herein. With the fenestrations 74, a maximum fluid distance from the device 10 can be reliably estimated and achieved regardless of the surrounding bone structure. Current devices have holes which allow jets of bone cement to be injected into the vertebral body. However, if a crack is present for conventional devices (i.e., not those described, contemplated and illustrated herein), the jets of bone cement will flow through the path of least resistance, which can cause the bone cement to flow or leak to undesired locations. Leakage of bone cement can cause injury to the patient. The fenestrations 74 can prevent or inhibit undesired flows from forming that can cause such injury.

FIG. 1A further illustrates that the device 10 can have one or more radiopaque markers 82 that can aid in placement of the device 10.

A bone spike (e.g., bone needle 44, wire 116, wire 117) can extend through the device 10, for example, through the shaft channel 28 along the device longitudinal axis $8_L$. The channel 28 can be advantageous, for example, for delivery of the device 10 over a needle, wire, bone spike, or any combination thereof. The bone spike can be configured to stabilize the device 10 early on during the insertion process and/or throughout the insertion process. The bone spike can be removed at some point during the insertion process, or after the device 10 has been fully implanted. The bone spike can pass through the center of the device 10. The bone spike can be slideable within the shaft channel 28. The attachment tool can removably receive the needle. The muffler can removably receive the needle.

Figure 2A:
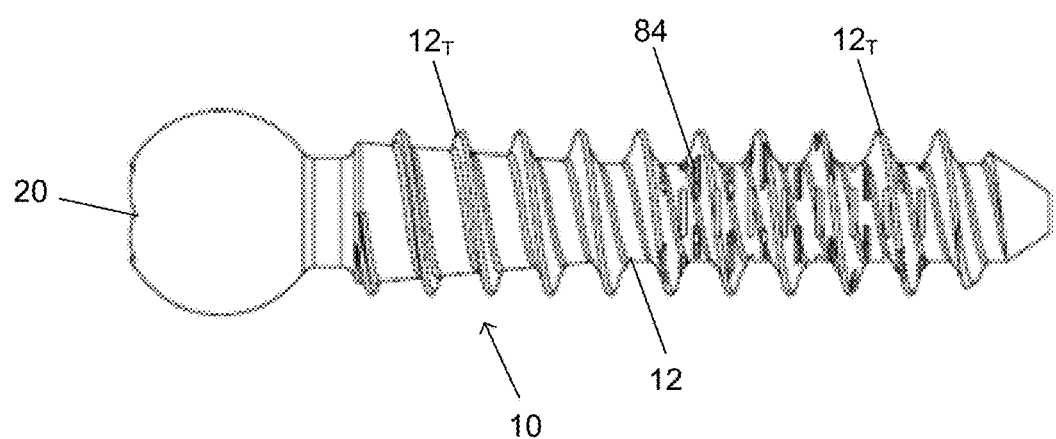
FIG. 2A illustrates a variation of an attachment device.
Figure 2B:
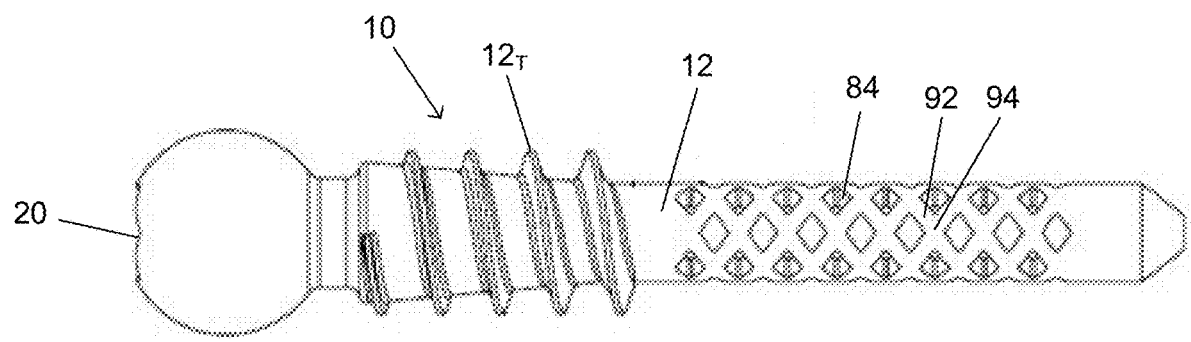
FIG. 2B illustrates the attachment device of FIG. 2A with the threads shown as translucent.

FIGS. 2A and 2B illustrate that the device 10 can have one or more fenestrations 84 (also referred to as holes or cells). The fenestrations 84 can have the same or different functions as the fenestrations 74. As another example, the fenestrations 84 can be the fenestrations 74. The device 10 can have 1 to 200 or more fenestrations 84, including every 1 hole increment within this range, for example, 64 fenestrations 84. The fenestrations 84 can have circular, elliptical, and/or polygonal (e.g., diamond) cross sections. The fenestrations 84 can have a diamond shape. The fenestrations 84 can advantageously allow bone to grow into the various components of the device 10 to secure the device 10 in place at the implant location. Anchoring fluid can be injected through the fenestrations 84.

The device 10 can have fenestrations 74, fenestrations 84, or both. When fluid is forced through the device 10, fluid can flow through fenestrations 74 and 84, through fenestrations 74 but not through fenestrations 84, or through fenestrations 84 but not through fenestrations 74. Bone can grow into the fenestrations that do not have fluid, for example, some or all of fenestrations 74, some or all of fenestrations 84, or any combination thereof. As another example, bone can rebound into the device 10 (e.g., into the fenestrations 74, 84, or both).

The fenestrations 74 can be anchoring fluid fenestrations, bone fenestrations, or both. The fenestrations 84 can be anchoring fluid fenestrations, bone fenestrations, or both.

FIG. 2A further illustrates that the fenestrations (e.g., 74 and/or 84) can extend through the threads $12_T$, through the wall of the shaft 12, or through both.

FIG. 2B further illustrates the shaft 12 without the threads $12_T$ on the non-tapered portion of the shaft 12 so that the fenestrations 84 can be more easily seen extending through the wall of the shaft. The device 10 (e.g., the shaft 12) can have struts 92 attached to each other at joints 94. The struts 92 can define the perimeters of the fenestrations 84.

Any of the devices 10 described, contemplated and illustrated herein can have a fixed length. The fixed length can be non-expandable.

Figure 3A:
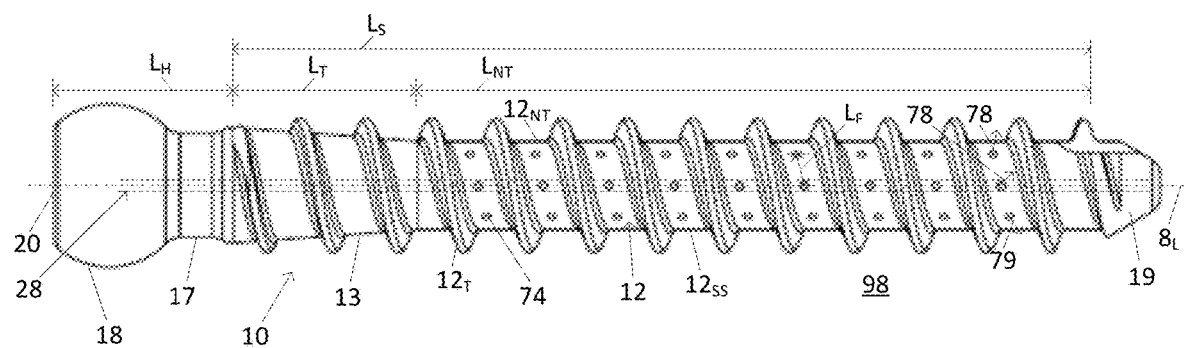
FIG. 3A illustrates a side view of a variation of an attachment device.

FIG. 3A illustrates that the device 10 can have an arrangement of fenestrations 74 along and around the device longitudinal axis $8_L$. The arrangement can be a circumferential arrangement such as a helical arrangement. The fenestrations 74 can be arranged along the length of the shaft 12 (e.g., along the shaft length $L_S$).

The fenestrations 74 can extend through the shaft 12 in the tapered portion 13, the non-tapered portion $12_{NT}$, or both. The fenestrations 74 can extend through the threads $12_T$ in the tapered portion 13, the non-tapered portion $12_{NT}$, or both. The fenestrations can extend through the shaft 12, through the threads $12_T$, or both. The shaft 12 can have threads $12_T$ with and/or without sections of the shaft 12 extending between the threads $12_T$. The shaft 12 can have threads $12_T$ with and/or without sections of the shaft 12 extending between the threads $12_T$ in the thread pitch. The sections of the shaft 12 that extend longitudinally between the threads $12_T$ can be referred to as shaft sections $12_{SS}$. A shaft section $12_{SS}$ can extend co-helically around the device 10 with the threads $12_T$. The fenestrations 74 can extend through the shaft sections $12_{SS}$ in the tapered portion 13, the non-tapered portion $12_{NT}$, or both. The fenestrations 74 can extend through the threads and sections $12_T$, $12_{SS}$ in the tapered portion 13, the non-tapered portions $12_{NT}$, or both. For devices where there is no shaft section $12_{SS}$ in the thread pitches, the fenestrations 74 can extend through the shaft 12 underneath the threads $12_T$ and then through the threads $12_T$. For example, FIG. 3A illustrates that the fenestrations 14 can extend through the non-tapered portion $12_{NT}$ but not through the tapered portion 13; however, the fenestrations 74 can be positioned through the shaft 12 in the tapered portion 13 in addition to or in lieu of the fenestrations 74 on the non-tapered portion $12_{NT}$. FIG. 3A further illustrates that the fenestrations 74 can extend through the shaft sections $12_{SS}$ between threads $12_T$. The holes 74 on the side wall of the device 10 can advantageously allow fluid (e.g., anchoring fluid such as bone cement) to flow through the device 10 and then into surrounding bone (e.g., a vertebra).

The spacing between adjacent fenestrations 74 can be constant long the length of the device 10, or can increase, decrease, or both. For example, FIG. 3A illustrates that the fenestrations can be separated by a length $L_F$. The length $L_F$ can extend along the outer surface of the shaft 12, for example, such that the length $L_F$ is an arc along a helix on which the fenestrations 74 are positioned. The length $L_F$ can be measured along a surface of the device 10. The length $L_F$ can be from about 0.5 mm to about 50.0 mm or more, more narrowly from about 0.5 mm to about 30.0 mm, more narrowly from about 0.5 mm to about 10.0 mm, or more narrowly still from about 0.5 mm to about 5.0 mm, including every 0.5 mm increment within these ranges.

FIG. 3A further illustrates that the shaft channel 28 can extend partially or entirely through the device 10 along the device longitudinal axis $8_L$. The channel 28 can be a central channel of the device 10, for example, a central cannula that is coaxial with the device longitudinal axis $8_L$. The channel 28 central axis can be offset or centered with the device longitudinal axis $8_L$.

FIG. 3A further illustrates the device 10 without a channel 45. However, the device 10, for example, illustrated in FIG. 3A, can have a channel 45 that extends through the tip 19 (e.g., as shown in FIG. 1A or any of the other figures).

FIG. 3A further illustrates that fluid (e.g., anchoring fluid) can flow out of the fenestrations 74, as indicated by the arrows 78.

FIG. 3A further illustrates that the device 10 can be inserted into bone 98. As shown, the fluid arrows 78 indicate that the fluid can flow into the bone 98, weep into the bone 98, or both.

Figure 3B:
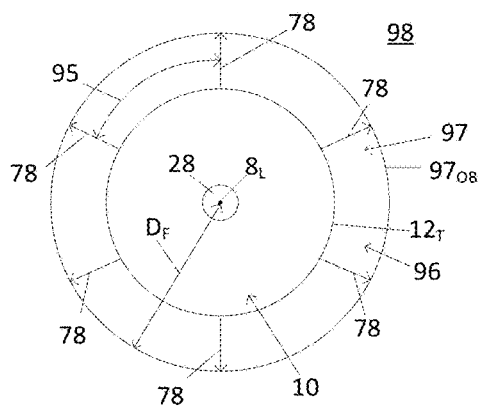
FIG. 3B illustrates a variation of an end view of the attachment device of FIG. 3A taken along line 3B-3B.

FIG. 3B illustrates that a fluid region 97 (also referred to as a fluid distribution) can form around the device 10 when the fluid 96 flows out of the fenestrations 10 as indicated by arrows 78. The fluid region 97 can extend partially or entirely around the device longitudinal axis $8_L$. The fluid region 97 can have a uniform or a non-uniform shape around the device 10. The fluid region 97 can have a regular or irregular shape. The fluid region 97 can form a shell (also referred to as an envelope) around the device 10. For example, the fluid region 97 can have an outer boundary $97_{OB}$. The fluid region outer boundary $97_{OB}$ can be a distance $D_F$ away from the device 10. The distance $D_F$ can be the maximum distance the fluid 96 permeates, weeps, or flows away from the device into the surrounding bone 98. The distance $D_F$ can be measured transversely away from the device longitudinal axis $8_L$, transversely away from the shaft 12 (e.g., from the threads $12_T$, from the shaft sections $12_{SS}$), or any combination thereof. For example, FIG. 3B illustrates that the distance $D_F$ can be measured transversely away from the device longitudinal axis to a point along the fluid region outer boundary $97_{OB}$. The distance $D_F$ can be, for example, about 1 mm to about 50 mm or more, including every 1 mm increment within this range.

FIG. 3B further illustrates that the device 10 can be inserted into the bone 98. Once the device 10 is inserted into the bone 98, a tool (e.g., attachment tool 48, a fluid filled syringe attached to the attachment tool 48) can force fluid (e.g., fluid 96) into the device 10 such that the fluid flows through the fenestrations 74 and into the bone 98. The fluid 96 can continue to be forced through the device 10 until a desired distance $D_F$ is achieved. The fenestrations 74 can control the fluid permeation rate and/or permeation pressure into the bone such that a uniform fluid region is created around the device 10, for example, as shown by the fluid region 97. For example, FIG. 3B illustrates that a shell 97 of fluid can be formed around the device 10 (e.g., a spinal screw). When the fluid 96 is injected through the device 10, the shell 97 that forms can have a cylinder-like shape. The shell 97 can be symmetrical across one, two, or three mutually perpendicular axes.

FIG. 3B further illustrates that the fenestrations 74 can be separated by an angle 95. The angle 95 can range from about 5 degrees to about 360 degrees or more, including every 1 degree increment within this range (e.g., 30 degrees, 60 degrees, 720 degrees). For example, FIG. 3B illustrates that the fenestrations 74 can be separated by 60 degrees along the helical arrangement.

FIGS. 3A and 3B further illustrate that the fenestration distal openings can be a constant distance away from the device longitudinal axis $8_L$. However, the fenestration distal openings can be the same or a different distance from the device longitudinal axis $8_L$ as other fenestration distal openings. The length of the fenestration paths can be constant or varied along the length of the device 10.

FIGS. 3A and 3B further illustrate that the fluid 96 can increase the anchor force with which the device 10 can be attached to the bone 98, for example, relative to when the device 10 is implanted without the fluid 96 and/or relative to when the device 10 is implanted with fluid openings that do not control the flow out of the device 10 as the fenestrations 74 are configured to accomplish. The fenestrations 74 can control the fluid flow through the device 10 by preventing the fluid flow from exceeding one or more threshold flow parameters through the fenestrations 74. The one or more threshold flow parameters can include a threshold flow rate, a threshold flow pressure, or both.

The threshold flow rate can be, for example, from about 0.25 cc/s to about 3.00 cc/s, or more narrowly, from about 0.80 cc/s to about 1.25 cc/s, including every 0.05 cc/s increment within these ranges (e.g., 0.50 cc/s, 0.80 cc/s, 1.00 cc/s, 1.25 cc/s). As another example, the threshold flow rate through the device 10 can be, for example, from about 0.25 cc/min to about 3.00 cc/min, or more narrowly, from about 0.80 cc/min to about 1.25 cc/min, including every 0.05 cc/min increment within these ranges (e.g., 0.50 cc/min, 0.80 cc/min, 1.00 cc/min, 1.25 cc/min).

The threshold flow rate through each of the fenestrations 74 (e.g., on a per fenestration basis) can be about 0.01 cc/s to about 0.50 cc/s, including every 0.01 cc/s increment within this range (e.g., 0.1 cc/s), or more narrowly, from about 0.005 cc/s to about 0.0250 cc/s, including every 0.001 cc/s increment within this range (e.g., 0.016 cc/s). Where the device 10 has fenestrations 74 with a single size, the threshold fenestration flow rate can be determined by dividing the threshold device flow rate by the number of fenestrations 74. For example, where the device 10 has 30 uniformly sized fenestrations 74 and the threshold device flow rate is about 0.5 cc/s, the threshold flow rate through each of the fenestrations 74 can be about 0.016 cc/s (e.g., 0.5 cc/s/30 fenestrations 74). Where the device 10 has fenestrations 74 of different sizes (e.g., two, three, four, five or more sizes), the threshold flow rate through the differently sized fenestrations 74 can be the same or different from one another. For example, the fenestrations 74 of the device 10 can include a device first fenestration and a device second fenestration smaller than the device first fenestration. The device first fenestration can be proximal to the device second fenestration, distal to the device second fenestration, or even with the device second fenestration. The threshold flow rate through the device first fenestration can be the same, larger than, or less than the threshold flow rate through the device second fenestration. For example, the threshold flow rate through the device first fenestration can be about 0.01 cc/s to about 0.50 cc/s, including every 0.01 cc/s increment within this range (e.g., 0.1 cc/s), or more narrowly, from about 0.005 cc/s to about 0.0250 cc/s, including every 0.001 cc/s increment within this range (e.g., 0.016 cc/s). The threshold flow rate through the device second fenestration can be about 0.01 cc/s to about 0.50 cc/s, including every 0.01 cc/s increment within this range (e.g., 0.1 cc/s), or more narrowly, from about 0.005 cc/s to about 0.0250 cc/s, including every 0.001 cc/s increment within this range (e.g., 0.016 cc/s).

The threshold flow pressure (also referred to as the threshold fluid delivery pressure) can be, for example, from about 400 psi to about 2000 psi, including every 100 psi range within this range, including every 1 psi increment within these ranges, or any combination thereof (e.g., about 450 psi). For example, a 5 cc syringe can be capable of producing 450 psi of pressure. The threshold fluid delivery pressure can be uniform through the fenestrations 74 or can depend on the size and shape of the fenestrations 74 for devices 10 having fenestrations 74 of different sizes. For example, the threshold fluid delivery pressure through the device first fenestration can be the same, larger than, or less than the fluid delivery pressure through the device second fenestration.

The fluid 96 can flow through the fenestrations 74 out into the bone 98. Once the fluid 96 is outside of the device 10, the fluid 96 will follow the path of least resistance. If the bone 98 is porous (e.g., osteoporotic) or has blood vessels or cracks, the fluid flow will be greater through these areas of less flow resistance if the flow through the device 10 is not controlled. The unregulated flow of fluid into these areas of less flow resistance can cause complications. The fenestrations 74 can regulate the flow of the fluid 96 into the bone 98 surrounding the device 10 by preventing the fluid flow through the fenestrations 74 from exceeding one or more of the threshold flow parameters. The fenestrations 74 can thereby advantageously prevent or inhibit unwanted flow rates which can lead to excessive fluid permeation into areas having less flow resistance. In this way, the injection of fluid into bone (e.g., bone 98) through a porous device (e.g., device 10) can be controlled. For example, the fenestrations 74 can be microfluidic channels within the wall of the shaft 12 that create predictive fluid flow per unit time such that jetting or the formation of high flow rates into low resistive areas of bone can be inhibited or prevented.

The fenestrations 74 can be positioned on the device 10 (e.g., along the shaft 12) based on bone imaging data (e.g., x-rays), for example, of the bone into which the device 10 is to be implanted. The number, size, shape and placement of the fenestrations 74 can be customized for the bone 98 into which the device 10 is to be attached.

The fluid 96 can harden after a hardening period. The hardening period can be, for example, about 30 seconds to about 10 minutes.

Figure 4A:
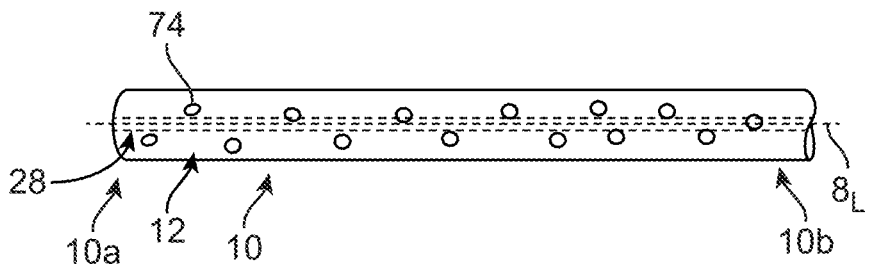
FIG. 4A illustrates a side view of a variation of an attachment device.

FIG. 4A illustrates that the shaft 12 can have uniformly sized and shaped fenestrations 74. The fenestrations 74 can have a constant size along the length of the shaft 12 or along a portion of the length of the shaft 12. The fenestrations 74 can have a constant shape along the length of the shaft 12 or along a portion of the length of the shaft 12. For example, the fenestrations 74 can be cylindrical tubes with circular cross-sections.

Figure 4B:
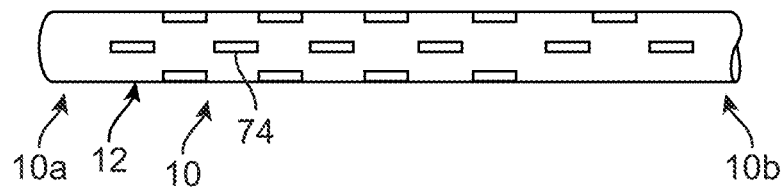
FIG. 4B illustrates a side view of a variation of an attachment device.

FIG. 4B illustrates that the fenestrations 74 can be slots (e.g., rectangular slots). The slots can have two shorter sides and two longer sides. The short sides can extend along a length of the shaft 12, along an arc around a portion of the circumference of the shaft 12, or both (e.g., for diagonally positioned slots). The long sides can extend along a length of the shaft 12, along an arc around a portion of the circumference of the shaft 12, or both (e.g., for diagonally positioned slots). For example, FIG. 4B illustrates that the long sides of the slots can extend in a longitudinal direction parallel with the device longitudinal axis $8_L$ and that the short sides of the slots can extend partially around the circumference of the shaft in a plane perpendicular to the device longitudinal axis $8_L$. The fenestrations 74 (e.g., slots) can have center longitudinal axis and a center transverse axis perpendicular to the center longitudinal axis.

Figure 4C:
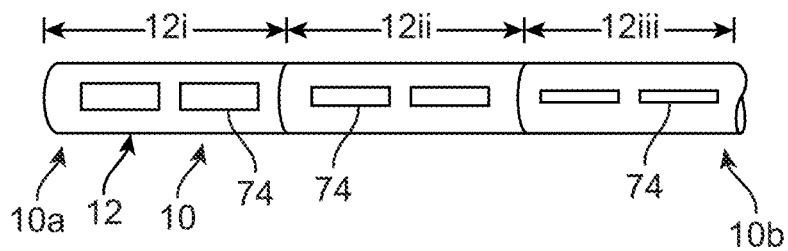
FIG. 4C illustrates a side view of a variation of an attachment device.

FIG. 4C illustrates that the device 10 can have fenestrations 74 with multiple sizes, for example, small, medium and large. The different sized fenestrations 74 can be arranged randomly on the shaft 12. The different sized fenestrations can be arranged in a gradient along the length of the shaft 12, for example, from smaller to larger and/or vice versa. The different sized fenestrations 74 can be arranged on different regions of the shaft 12 according to the size of the fenestration 74. FIG. 4C illustrates that the shaft 12 can have shaft first, second and third regions $12i$, $12ii$, $12iii$. Each shaft region (e.g., $12i$, $12ii$, $12iii$) can have zero, one, or multiple fenestrations 74. The size of the fenestrations 74 can be larger in the shaft first region $12i$ than in the shaft second region 12*ii* and larger in the shaft second region 12*ii* than in the shaft third region 12*iii*, or vice versa. For example, large fenestrations can be in shaft region 12*i*, medium fenestrations can be in shaft region 12*ii*, and small fenestrations can be in shaft region 12*iii*. The size of the fenestrations 74 can be smaller in the shaft first region 12*i* than in the shaft second region 12*ii* and smaller in the shaft second region 12*ii* than in shaft third region 12*iii*, or vice versa. For example, small fenestrations can be in shaft region 12*i*, medium fenestrations can be in shaft region 12*ii*, and large fenestrations can be in shaft region 12*iii*. As yet another example, large fenestrations can be in shaft region 12*i*, small fenestrations can be in shaft region 12*ii* and medium fenestrations can be in shaft region 12*iii*. The size of the fenestrations 74 in each shaft region 12 can be constant or varied. The arrangement of different sized fenestrations 74 into a gradient can advantageously create a uniform flow field through and around the device 10. The shaft first region 12*i* can be on the device proximal end 10*a* and the shaft third region can be on the device distal end 10*b*, or vice versa. The terms small, medium and large in relation to the fenestration sizes can be relative to each other such that the smallest fenestration can be the small size, the next smallest fenestration can be the medium size and the next smallest fenestration can be the large size. For example, the small, medium and large sizes can be the sizes of three differently sized small fenestrations. As another example, the small, medium and large sizes can be the sizes of three differently sized large fenestrations.

Figure 4D:
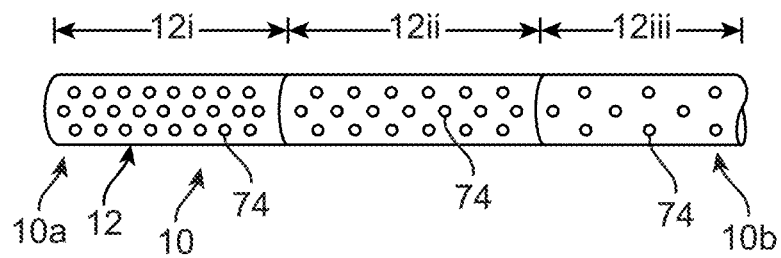
FIG. 4D illustrates a side view of a variation of an attachment device.

FIG. 4D illustrates that the number of fenestrations 74 can be different in different regions of the shaft 12. The fenestrations 74 can be arranged to form a gradient along a length of the device 10. For example, the number of fenestrations on the device proximal end 10*a* can be greater than the number of fenestrations on the device distal end 10*b*, or vice versa. FIG. 4D illustrates that more fenestrations can be in shaft region 12*i* than 12*ii* and more can be in shaft region 12*ii* than 12*iii*. As another example, more fenestrations can be in shaft region 12*iii* than 12*ii* and more can be in shaft region 12*ii* than 12*i*.

Figure 4E:
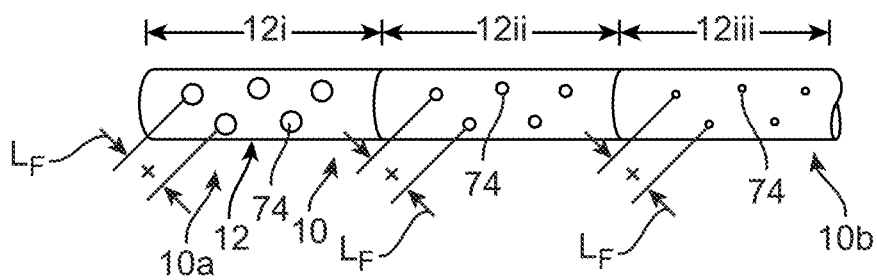
FIG. 4E illustrates a side view of a variation of an attachment device.

FIG. 4E illustrates another variation of a fenestration gradient in which the fenestration number in each of the shaft regions (e.g., 12*i*, 12*ii*, 12*iii*) is the same and where the size of the fenestrations in the different regions (e.g., 12*i*, 12*ii*, 12*iii*) is different from one or more of the other regions.

FIG. 4E further illustrates that the length $L_F$ can increase, decrease, or stay the same as the fenestrations 74 increase or decrease in size from one shaft region to the next.

Figure 4F:
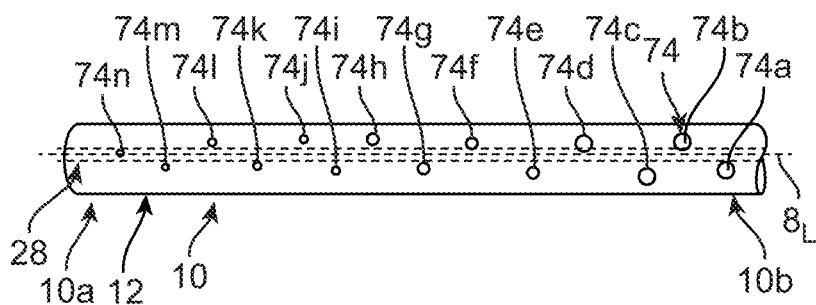
FIG. 4F illustrates a side view of a variation of an attachment device.

FIG. 4F illustrates that the size of the fenestrations 74 can progressively increase, decrease, or both along a length of the device 10. For example, the fenestrations 74*a*-74*n* can progressively increase in size from the device proximal end 10*a* to the device distal end 10*b*, or vice versa. As another example, the fenestrations 74 (e.g., fenestrations 74*a*-74*n*) can progressively increase in size from a proximal fenestration (e.g., fenestration 74*a*) to a middle fenestration (e.g., 74*g* or 74*h*) and can progressively decrease in size from the middle fenestration to a distal fenestration (e.g., fenestration 74*n*). As yet another example, the fenestrations 74 (e.g., fenestrations 74*a*-74*n*) can progressively decrease in size from a proximal fenestration (e.g., fenestration 74*a*) to a middle fenestration (e.g., 74*g* or 74*h*) and can progressively increase in size from the middle fenestration to a distal fenestration (e.g., fenestration 74*n*).

FIGS. 4D-4F illustrate that the fenestrations 74 can be arranged in one or multiple gradients along a length of the shaft 12, for example, fenestration size gradients, fenestration number gradients, fenestration density gradients, or any combination thereof. Each shaft region (e.g., 12*i*, 12*ii*, 12*iii*) can have the same or different fenestration size, fenestration shape, fenestration density, fenestration gradient, or any combination thereof another shaft region. The shaft regions can have the same or different dimensions as one another.

The shafts 12 in FIGS. 4A-4E are illustrated without threads $12_T$. However the shafts 12 in FIGS. 4A-4F can have threads, for example, threads $12_T$.

FIG. 4G illustrates that the fenestrations 74 can have a rectangular shape.

FIG. 4H illustrates that a longitudinal axis of the fenestrations 74 can be angled relative to the device longitudinal axis, for example, by about 10 degrees to about 90 degrees, including every 1 degree increment within this range (e.g., about 45 degrees).

FIG. 4I illustrates that the fenestrations 74 can be adjacent to one another.

FIG. 4J illustrates that the fenestrations 74 can have a triangular shape.

FIG. 5 illustrates that the fenestrations 74 can define a sinusoidal fenestration path. FIG. 5 further illustrates that the fenestration 74 can have a fenestration distal end $74_{DE}$ and a fenestration proximal end $74_{PE}$. The fenestration path can extend between the fenestration distal and proximal ends $74_{DE}$, $74_{PE}$. The fenestration distal end $74_{DE}$ can open toward the environment (e.g., bone 98) and the fenestration proximal end $74_{PE}$ can open toward the cannula of the shaft 12 (e.g., channel 28). The fenestration distal end $74_{DE}$ can be the fenestration outlet and the fenestration proximal end $74_{PE}$ can be the fenestration inlet or vice versa depending on the direction of fluid flow.

FIG. 6A illustrates that the fenestrations 74 can have one or more fluid resistive structures 104 (also referred to as flow restrictors). The fluid resistive structures 104 can be one or multiple baffles, liners, mesh, or any combination thereof. The fluid resistive structures can be attached to or integrated with the device 10.

FIG. 6B illustrates that the fluid resistive structure 104 can extend across the fenestration 74 at the fenestration distal end.

FIG. 6C illustrates that the fluid resistive structure 104 can extend across the fenestration path between the fenestration proximal and distal ends, for example, at a midpoint between the fenestration proximal and distal ends.

FIG. 6D illustrates that the fluid resistive structure 104 can extend across the fenestration at the fenestration proximal end.

FIGS. 6A-6D further illustrate that the fluid resistive structures 104 decrease the side of the fenestrations 74 to increase the resistance to fluid flow.

FIGS. 5-6D illustrate that fenestration paths can be tortuous (e.g., sinusoidal saw tooth), non-tortuous (e.g., straight), flow uninhibited (e.g., no flow resistive structure), flow inhibited (e.g., the fenestration includes a flow resistive structure 104), or any combination thereof.

FIG. 7 illustrates that the device 10 can have one or multiple exterior cutting ports 106. The cutting ports 106 can cut tissue and fluid (e.g., bone cement) when the device 10 is rotated in a first direction and can slide past tissue (e.g., bone 98) without cutting it when the device 10 is rotated in a second direction opposite the first direction.

A portion of the fenestrations 74 can form the exterior cutting ports 106. For example, the fenestration distal ends $74_{DE}$ can have a cutting side 106*a* and a blunt side 106*b*. The cutting side 106*a* of the ports 106 can have a cutting edge to cut the fluid 96 (e.g., hardened fluid 96) when the device 10 is rotated in the direction of arrow 108. The cutting edge can be a sharpened edge, for example, a tapered edge as shown. The blunt side 106*b* of the ports 106 can have a non-cutting edge that does not cut the fluid 96 (e.g., hardened fluid 96) when the device 10 is rotated in the direction of arrow 110. The blunt edge can be a dull edge, for example, a rounded surface as shown.

Additionally or alternatively, the device 10 can have exterior cutting ports 106 that are separate from the fenestrations 74. As another example, the ports 106 can be grooves in or indents on an exterior surface of the shaft 12 that do not extend through the shaft 12 to the shaft channel 28.

FIG. 7 further illustrates that the fluid 96 can harden outside and inside the device, for example, in the bone 98, in a space between the bone 98 and the device 10, in the fenestrations 74, in the device cannula (e.g., channel 28), or any combination thereof.

Figure 8A:
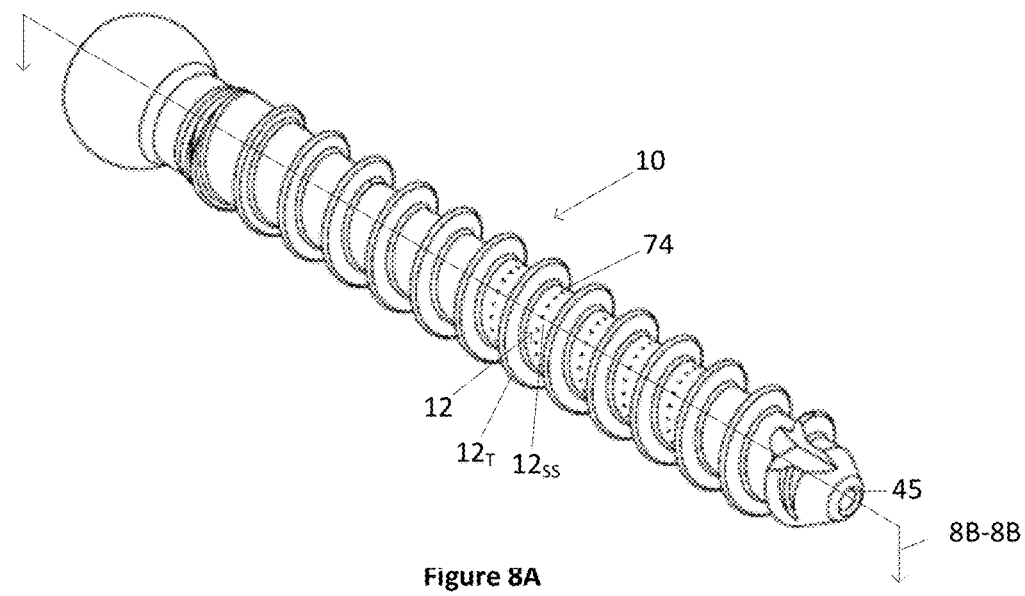
FIG. 8A illustrates a perspective view of a variation an attachment device.

FIG. 8A illustrates that the fenestrations 74 of the device 10 can be laser cut holes. It has been found experimentally that laser cut holes or slots with a small size, for example, having a cross-sectional area from about 1 mm$^2$ to about 25 mm$^2$, including every 1 mm$^2$ increment within this range, can provide significant resistance to the flow of the fluid 96 (e.g., viscous bone cement). The cross-section can be, for example, the cross-section of the inlet and/or outlet of the fenestrations. Such resistance, by design, can cause the bone cement to weep from the surface of the device 10 irrespective of the surrounding bone structure, for example, whether the bone has a non-homogeneous structure (e.g., is porous and has one or more paths of least resistance) or whether the bone has a homogeneous structure (e.g., does not have a path of least resistance). The fenestrations 74 can be spaced equally apart along in a helical pattern around the shaft 12. The fenestrations 74 can be positioned, for example, along 1 to 40 or more helical revolutions around the shaft 12 (e.g., along 5 helical revolutions). The fenestrations 74 can be positioned through the shaft sections 12$_{SS}$, for example, along 5 helical revolutions around the shaft 12.

Figure 8B:
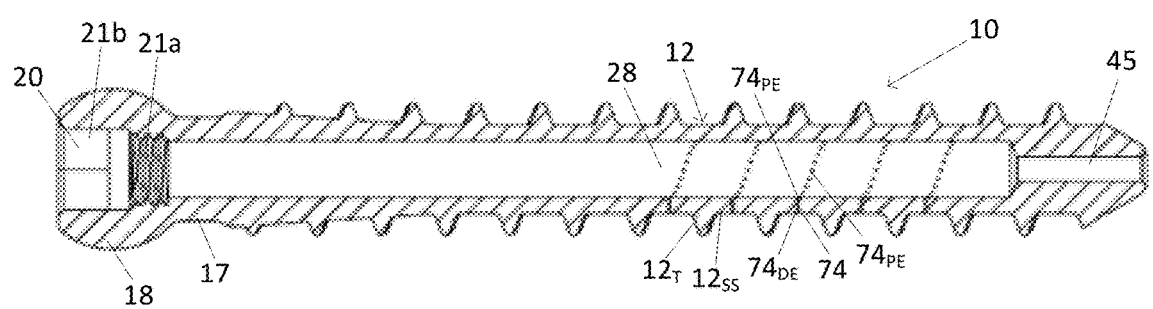
FIG. 8B illustrates a variation of a longitudinal cross-sectional view of the attachment device of FIG. 8A taken along line 8B-8B.

FIG. 8B illustrates that the fenestrations 74 can extend radially away from the device longitudinal axis 8$_L$. The fenestration paths can extend perpendicularly or non-perpendicularly away from the device longitudinal axis 8$_L$. For example, the fenestrations 74 can extend away from the device longitudinal axis 8$_L$ at a fenestration angle, where the fenestration angle can be from about 10 degrees to about 170 degrees, including every 1 degree increment within this range (e.g., 45 degrees, 90 degrees, 135 degrees). The fenestration path can extend through the wall of the shaft 12 at one or more angles. For example, FIG. 8B illustrates that the fenestration can be straight and extend through the shaft wall at about 90 degrees relative to the device longitudinal axis 8$_L$. The fenestration distal end 74$_{DE}$ can be in the shaft section 12$_{SS}$, for example, in the thread pitch (e.g., halfway across the thread pitch).

FIG. 8B further illustrates that the tool attachment port 20 can be a chamber in the end cap 18. The tool attachment port 20 can have a tool first engager 21*a*, a tool second engager 21*b*, or both. FIG. 8B illustrates that the tool first engager 21*a* can include screw threads and that the tool second engager can be a chamber with curved and/or flat sides forming a chamber having a polygonal cross-section (e.g., a polygonal cross-section). A first tool can engage with the tool first engager 21*a*, the tool second engager 21*b*, or both. A second tool can engage with the tool first engager 21*a*, the tool second engager 21*b*, or both. For example, the first tool can engage with the tool first engager 21*a* and the second tool can engage with the tool second engager 21*b*. For example, the attachment tool 48 can be engageable with the tool first engager 21*a*, the tool second engager 21*b*, or both. As another example, the driver 50 can be engageable with the tool first engager 21*a*, the tool second engager 21*b*, or both.

Figure 9:
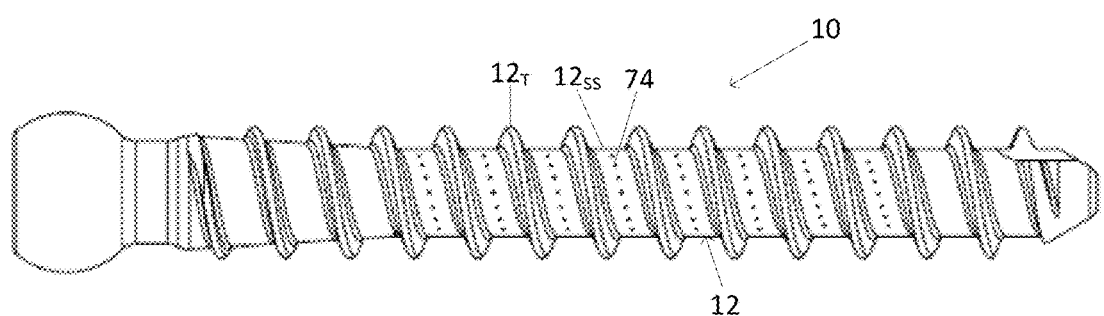
FIG. 9 illustrates a side view of a variation of an attachment device.

FIG. 9 illustrates that the fenestrations 74 can be positioned in the shaft sections 12$_{SS}$, for example, in the shaft sections 12$_{SS}$ along 8 helical revolutions around the shaft 12.

Figure 10A:
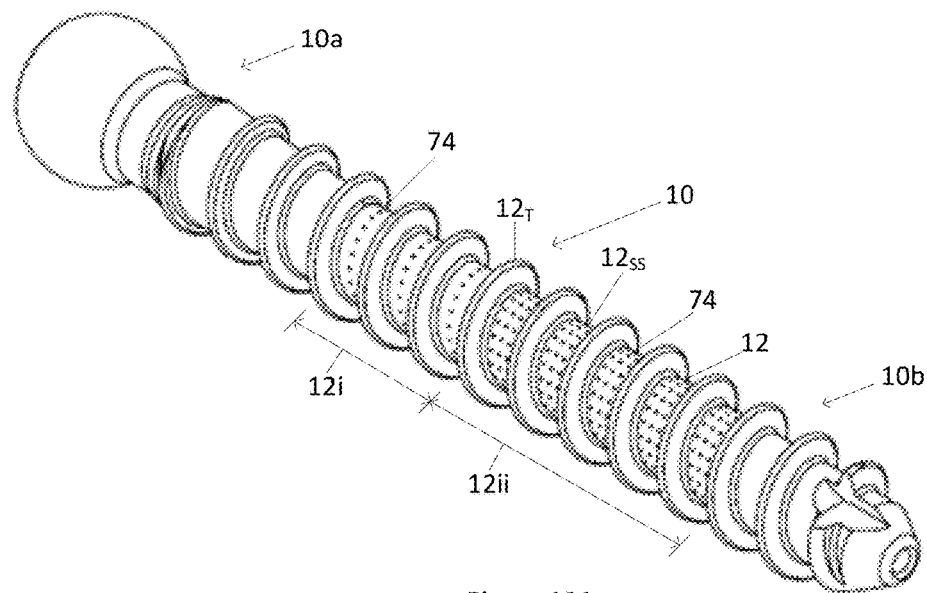
FIG. 10A illustrates a perspective view of a variation an attachment device.
Figure 10B:
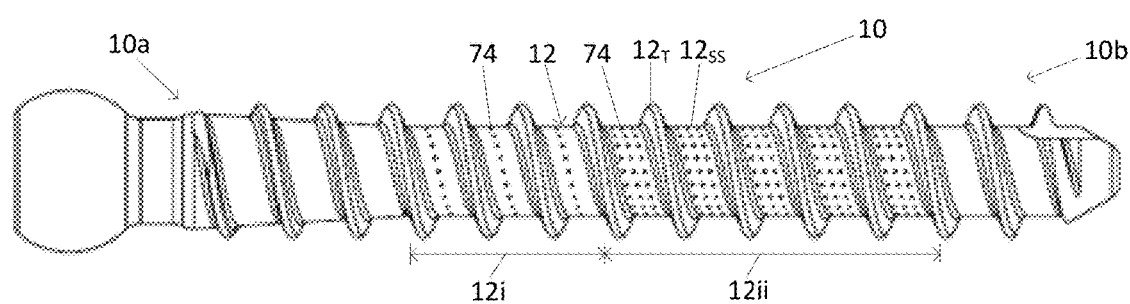
FIG. 10B illustrates a variation of a side view of the attachment device of FIG. 10A.

FIGS. 10A and 10B illustrate that the fenestrations 74 can be arranged in a gradient pattern. For example, FIGS. 10A and 10B illustrate that the density of fenestrations 74 can increase form the device proximal end 10*a* to the device distal end 10*b*. The gradient pattern can allow for a consistent amount of fluid to pass through the wall of the device 10. More holes can be placed at the device distal end 10*b* than the device proximal end 10*b*. Increasing the number or the size of the fenestrations 74 on the device distal end 10*b* can accommodate for the fluid pressure decrease that can be caused by the passage of fluid through the more proximal holes. The fenestration distribution in FIGS. 10A and 10B can advantageously achieve equal flow of fluid through the wall of the device 10 when fluid is delivered. FIGS. 10A and 10B illustrate that a single line of fenestrations can extend around the shaft in a first shaft region 12*i* and that three lines of fenestrations can extend around the shaft in a shaft second region 12*ii*. FIGS. 10A and 10B further illustrate that the fenestrations 74 can be distributed along the length of the device 10 as shown.

Figure 11:
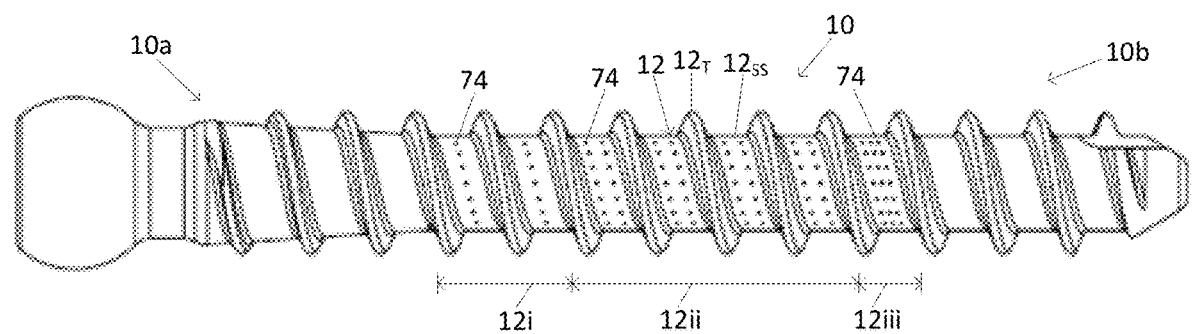
FIG. 11 illustrates a side view of a variation of an attachment device.

FIG. 11 illustrates that the fenestrations 74 can be arranged in a gradient pattern having three fenestration regions with more fenestrations on the device distal end 10*b* than the device proximal end 10*a*. The fenestration density can increase from the device proximal end 10*a* to the device distal end 10*b*. The fenestration distribution in FIG. 11 can advantageously achieve equal flow of fluid through the wall of the device 10. FIG. 11 illustrates that one line of fenestrations can extend around the shaft in a first shaft region 12*i*, two lines of fenestrations can extend around the shaft in a shaft second region 12*ii*, and three lines of fenestrations can extend around the shaft in a shaft third region 12*iii*. FIG. 11 further illustrates that the fenestrations 74 can be distributed along the length of the device 10 as shown.

Figure 12A:
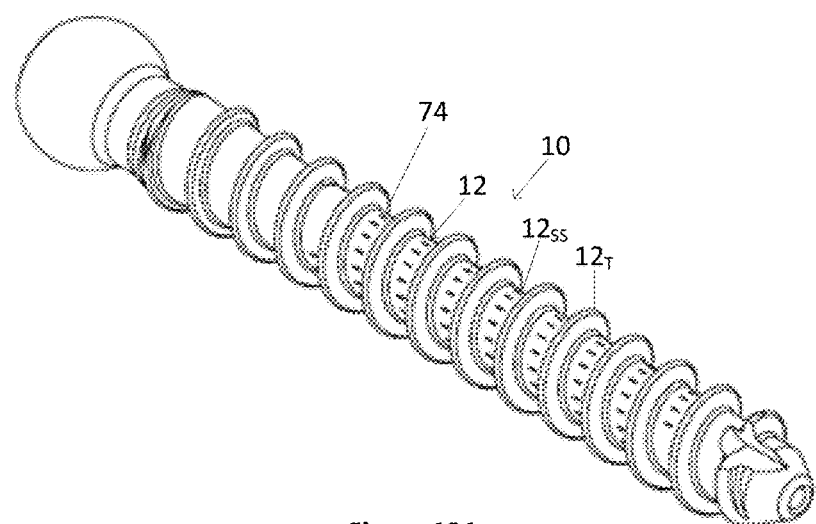
FIG. 12A illustrates a perspective view of a variation an attachment device.
Figure 12B:
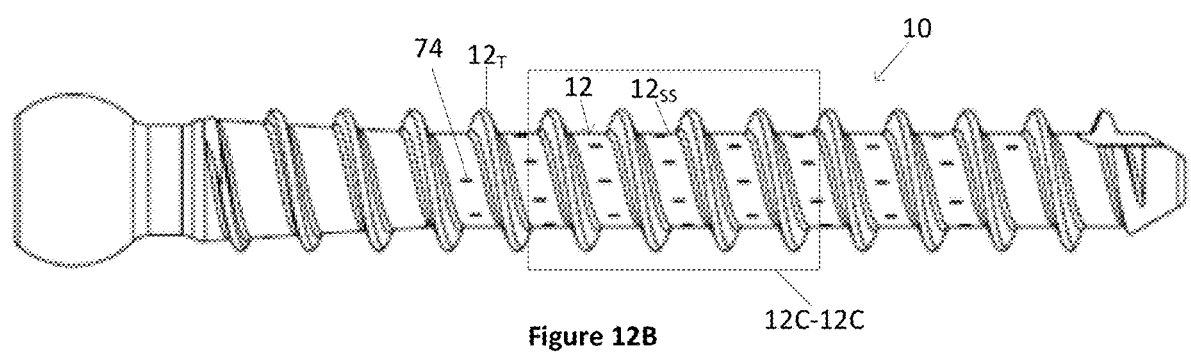
FIG. 12B illustrates a variation of a side view of the attachment device of FIG. 12A.
Figure 12C:
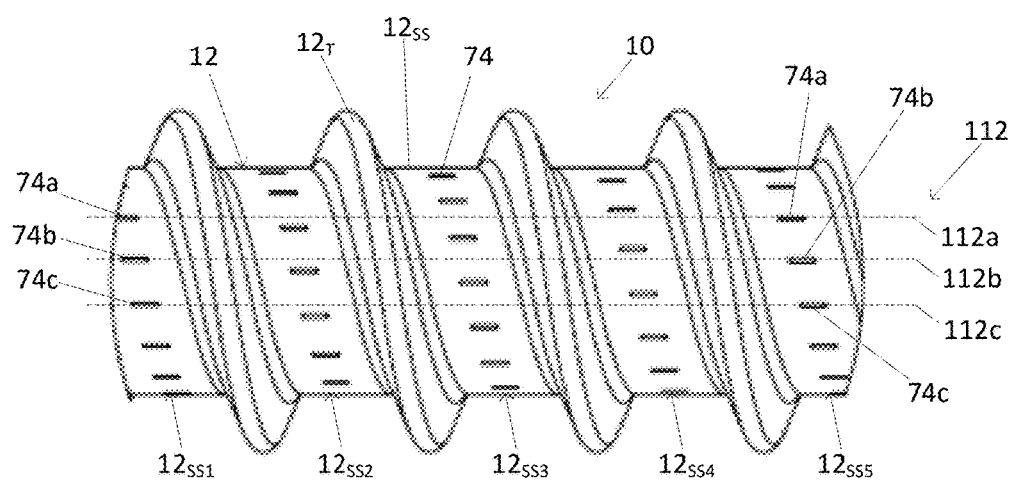
FIG. 12C is a magnified view of the attachment device of FIG. 12B at section 12C-12C.

FIGS. 12A-12C illustrate that the fenestrations 74 can be slots. The slots can be laser cut slots. It has been found experimentally that slots can be advantageous over round or radial holes when designed to be very small, for example, when the cross-sectional area of the fenestration is from about 1 mm$^2$ to about 25 mm$^2$, including every 1 mm$^2$ increment within this range. Bone cement tends to separate into its constituents during high pressure delivery through very small holes, for example, holes having cross-sectional areas less than from about 1 mm$^2$ to about 25 mm$^2$, including every 1 mm$^2$ increment within this range. These cross-sections can be, for example, the cross-section of the inlet and/or outlet of the holes. Slots (e.g., laser cut slots) can fix this by having a first dimension within the feature (e.g., the fenestration 74) much larger than a second dimension. The first dimension can be the length of the fenestration 74 and the second dimension can be the width of the fenestration. FIG. 12C further illustrates that the slots can have a stadium shape. FIG. 12C further illustrates that the fenestrations 74 can be spaced apart to be offset along fenestration placement axes 112. The fenestrations 74 can be distributed to repeat along a placement axis 112 every N revolutions around the shaft 12, where N can be 1 to 40 or more, including every 1 revolution increment within this range. Additionally or alternatively, N can be number of shaft sections between threads. For example, FIG. 12C illustrates that N can be 5 revolutions or 5 shaft sections (e.g., see shaft sections $12_{SS1}$, $12_{SS2}$, $12_{SS3}$, $12_{SS4}$, $12_{SS5}$), where the two fenestrations labeled 74a lie on the 112a distribution axis, the two fenestrations labeled 74b lie on the 112b distribution axis, and the two fenestrations labeled 74c lie on the 112c distribution axis. The device 10 can have 1 to 100 or more shaft sections $12_{SS}$.

Figure 13:
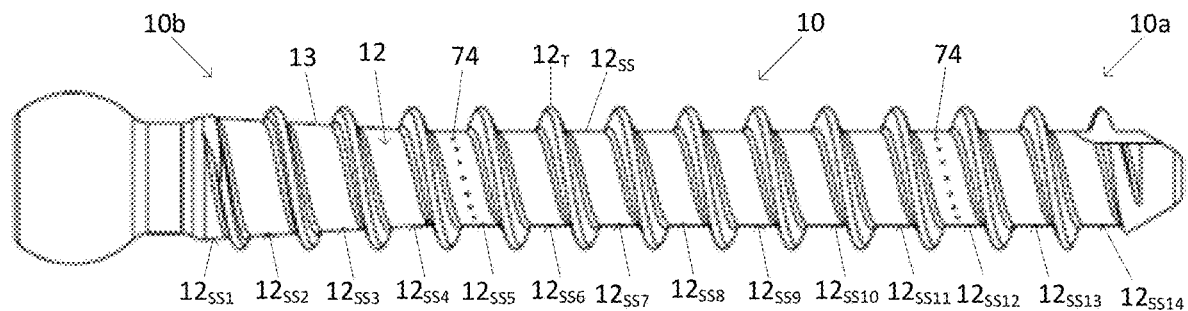
FIG. 13 illustrates a side view of a variation of an attachment device.

FIG. 13 illustrates that the fenestrations 74 can be distributed on the device 10 as shown, with fenestrations 74 at two ends of the device 10. The two ends of the device 10 can be the device proximal and distal ends 10a, 10b. As shown, the fenestrations 74 can be distributed in two regions on opposite sides of a center of the device (e.g., a transverse center of the device 10, a transverse center of the shaft 12). The device 10 can have 14 shaft sections $12_{SS}$ (e.g., shaft sections $12_{SS1}$-$12_{SS14}$). The fenestrations 74 can be distributed in any of the shaft sections $12_{SS}$. For example, FIG. 13 illustrates that the fenestrations 74 can be distributed in shaft sections $12_{SS5}$ and $12_{SS12}$ as numbered proximally to distally. Having the fenestrations 74 at the ends of the shaft 12 can desirably allow for a wide distribution of the fluid 96 into surrounding bone (e.g., bone 98). A significant increase in anchor strength has been found with a reduction of the volume of bone cement used where the fluid 96 is distributed from fenestrations 74 on opposite sides of the shaft 12. This can be advantageous, as bone cement can release a significant amount of heat during curing (polymerization).

Figure 14A:
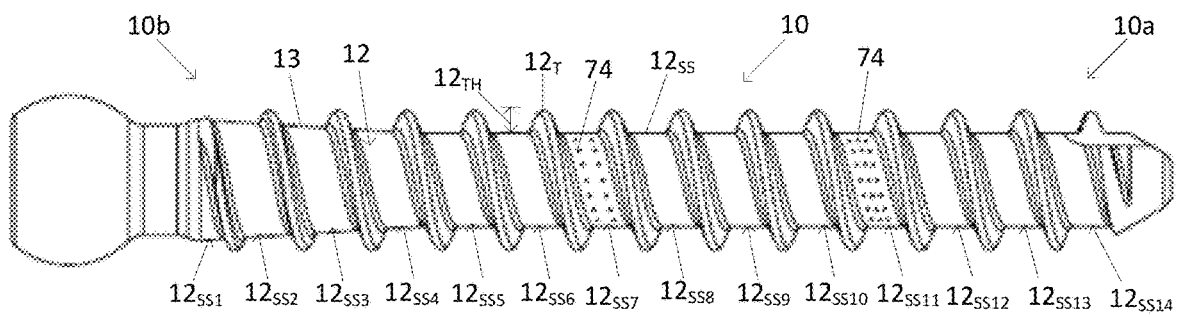
FIG. 14A illustrates a side view of a variation of an attachment device.

FIG. 14A illustrates that the fenestrations 74 can be arranged in a gradient pattern such that there are more fenestrations closer to the device distal end 10b than the device proximal end 10a. The fenestrations 74 can be distributed in shaft sections $12_{SS7}$ and $12_{SS11}$. FIG. 14A further illustrates that the shaft section $12_{SS7}$ can have a less fenestrations 74 than the shaft section $12_{SS11}$, for example, 10-50% less, 33% less, or as another example, 1 to 20 or more fenestrations less, 7 fenestrations less). FIG. 14A further illustrates that the threads $12_T$ can have a thread height $12_{TH}$ of about 1.50 mm to about 4.00 mm, including every 0.25 mm increment within this range (e.g., 1.50 mm, 2.00 mm).

Figure 14B:
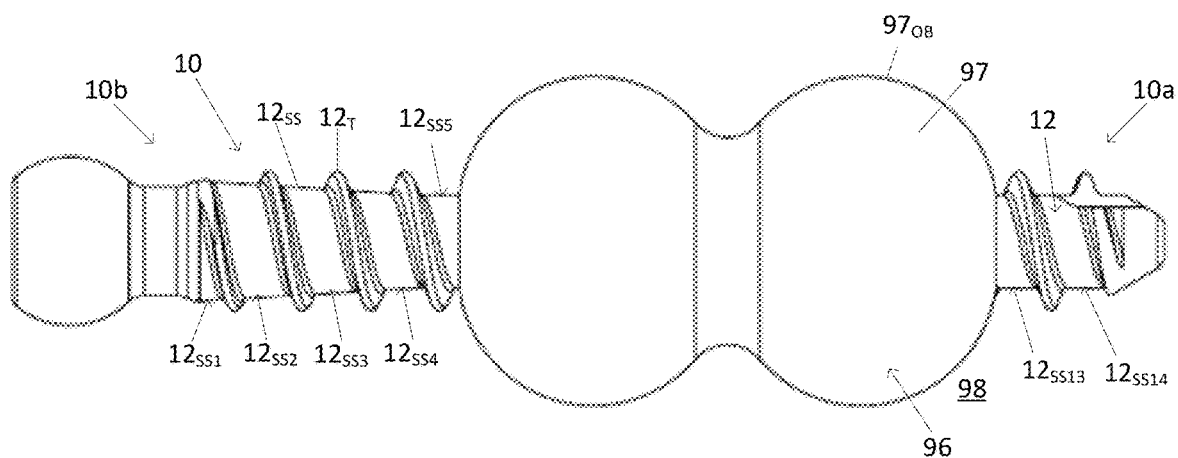
FIG. 14B illustrates a side view of a variation of a fluid distribution from fluid injected through the device of FIG. 14A.

FIG. 14B illustrates the fluid distribution 97 that can form when fluid is distributed through the device 10 of FIG. 14A. The fluid distribution 97 can allow for more interaction (e.g., more surface area) of the fluid 96 with the bone, for example, with osteoporotic cancellous bone.

Figure 15A:
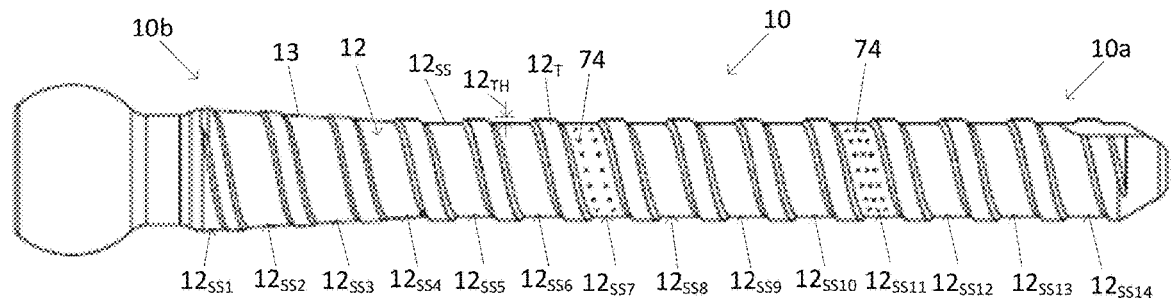
FIG. 15A illustrates a side view of a variation of an attachment device.
Figure 15B:
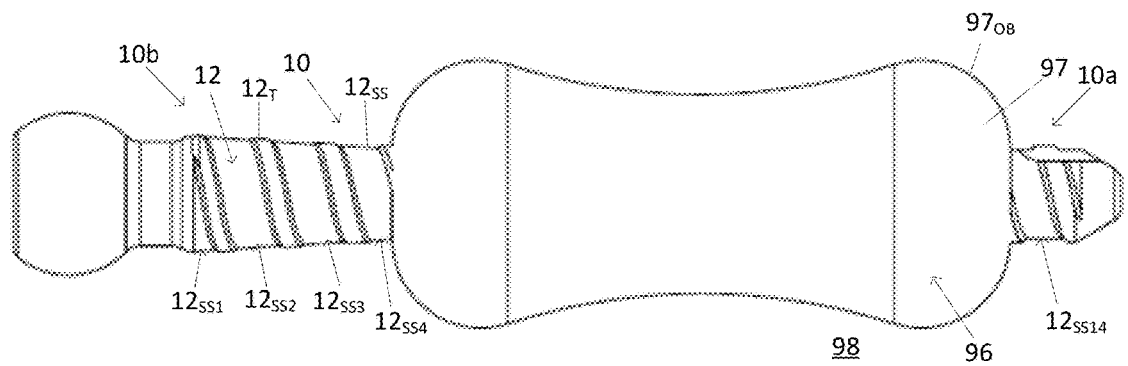
FIG. 15B illustrates a side view of a variation of a fluid distribution from fluid injected through the device of FIG. 15A.

FIG. 15A illustrates the device 10 of FIG. 14A with a smaller thread height $12_{TH}$. The smaller thread height $12_{TH}$ can be, for example, from about 0.25 mm to about 3.50 mm, including every 0.25 mm increment within this range (e.g., 1.00 mm, 1.50 mm, 3.25 mm). A thread height $12_{TH}$ within this range can allow for a device 10 to be used in small anatomy patients such as children and petite adults. Advantageously, and as the fluid distribution 97 in FIG. 15B illustrates, the device 10 having threads $12_T$ with a smaller thread height $12_{TH}$ can retain the strength, or most of the strength, associated with the fluid distribution 97 distributed by the device 10 of FIG. 14A. The strength of the fluid 96 can distribute the load within the stabilization hardware relative to the bone (e.g., bone 98) which allows for the thread profile to be minimized. A smaller thread height $12_{TH}$ also allows for easier device removal from the fluid 96 as there is less surface area between the device 10 and the fluid 96.

FIGS. 15A and 15B further illustrate that the device 10 can have typical course thread heights, shorter thread heights as shown, no threads, or any combination thereof. Shorter or no threads can allow for greater porosity (e.g., a thicker device wall can handle more fenestrations/holes and larger inner cannulation). Shorter or no threads can provide easier screw removal after cement injection, for example, because there is less thread surface for the cement to stick to.

Figure 16:
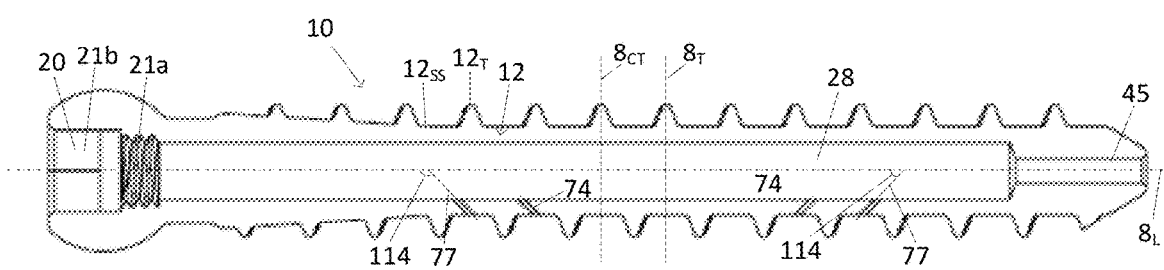
FIG. 16 illustrates a longitudinal cross-sectional view of a variation of an attachment device.

FIG. 16 illustrates that the fenestrations 74 can be off axis from radial axes extending from the device longitudinal axis $8_L$. For example, the fenestrations 74 can be angled relative to the device longitudinal axis $8_L$ with an angle 114. These angles 114 can desirably give the fluid 96 a trajectory towards the center of the bone 98 (e.g., vertebral body), towards the center of the implant location in the bone 98, towards a longitudinal center of the device 10, towards a longitudinal center of the shaft 12, or any combination thereof. The angle 114 can be from about 10 degrees to about 170 degrees, including every 5 degree increment within this range (e.g., 15 degrees, 30 degrees, 45 degrees, 60 degrees, 75 degrees, 90 degrees, 105 degrees, 120 degrees, 135 degrees, 150 degrees, 165 degrees). The angle can be measured between the device longitudinal axis $8_L$ and a fenestration axis 77, for example, counterclockwise from the device longitudinal axis $8_L$. The fenestration axis 77 can be a longitudinal axis of the fenestration 74, for example, a center longitudinal axis. The angle 114 can be greater than 90 degrees for the proximally positioned fenestrations 74 and can be less than 90 degrees for the distally positioned fenestrations, where the device transverse axis $8_T$ or any other transverse axis $8_T$ between the device proximal and distal terminal ends. The angle 114 can be the same for each of the proximal fenestrations 74 (e.g., the two leftmost fenestrations 74 in FIG. 16) or can progressively approach 90 degrees as the positions of the fenestrations 74 approaches the device transverse axis $8_T$. The angle 114 can be the same for each of the distal fenestrations 74 (e.g., the two rightmost fenestrations 74 in FIG. 16) or can progressively approach 90 degrees as the positions of the fenestrations 74 approaches the device transverse axis $8_T$. The device transverse axis $8_T$ can be offset from the center transverse axis of the device. The device center transverse axis is shown in FIG. 16 as axis $8_{CT}$. Anywhere in this application, in this and any other context, the device longitudinal and transverse axes (e.g., axes $8_L$, $8_T$, $8_{CT}$) can be device longitudinal and transverse planes.

Figure 17A:
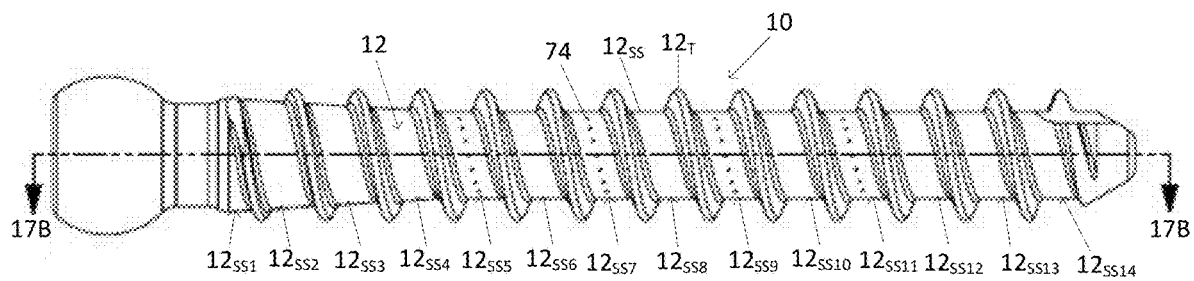
FIG. 17A illustrates a side view of a variation of an attachment device.

FIG. 17A illustrates that the fenestrations 74 can be distributed in shaft sections $12_{SS5}$, $12_{SS7}$, $12_{SS9}$ and $12_{SS11}$. The device 10 can have fenestrations 74 distributed on the opposite sides of shaft sections $12_{SS4}$, $12_{SS6}$, $12_{SS8}$, $12_{SS10}$, $12_{SS12}$, or any combination thereof, including the opposite sides of any of the other labeled shaft sections $12_{SS}$.

Figure 17B:
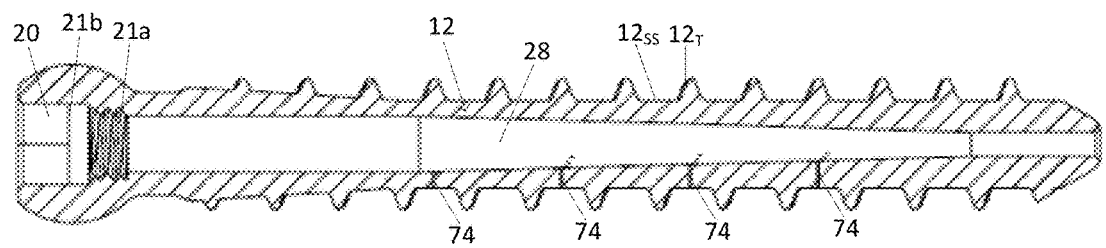
FIG. 17B illustrates a variation of a longitudinal cross-sectional view of the attachment device of FIG. 17A taken along line 17B-17B.

FIG. 17B illustrates that the device 10 can have a tapered central cannula (e.g., tapered channel 28) to create even fluid distribution through the wall of the device 10. The tapered channel 28 can enable the device 10 to create even fluid distribution through the wall of the device 10 without having to change the shape or density of the fenestrations 74 (also referred to as side wall penetrations). The length of the fenestrations 74 can progressively get larger as the channel 28 tapers from a first cross-sectional size to a second cross-sectional size smaller than the first cross-sectional size, for example, as shown by the increasing length of the fenestrations 74 from the leftmost to rightmost fenestration 74 in FIG. 17B.

Figure 17C:
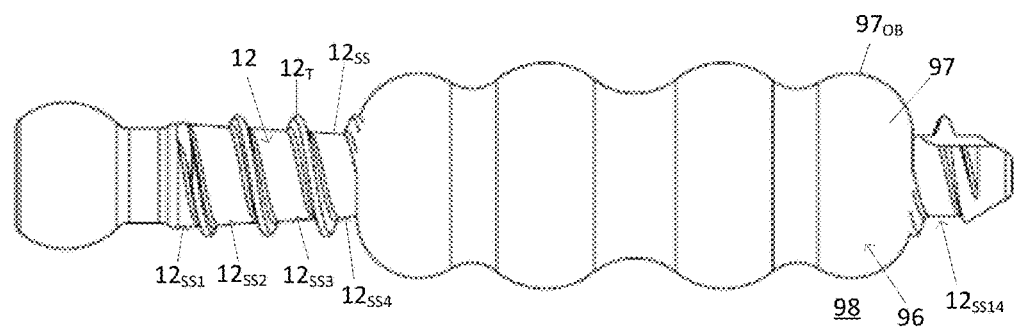
FIG. 17C illustrates a side view of a variation of a fluid distribution from fluid injected through the device of FIG. 17A.

FIG. 17C illustrates the fluid distribution 97 that can form when fluid is distributed through the device 10 of FIG. 17A.

Figure 18A:
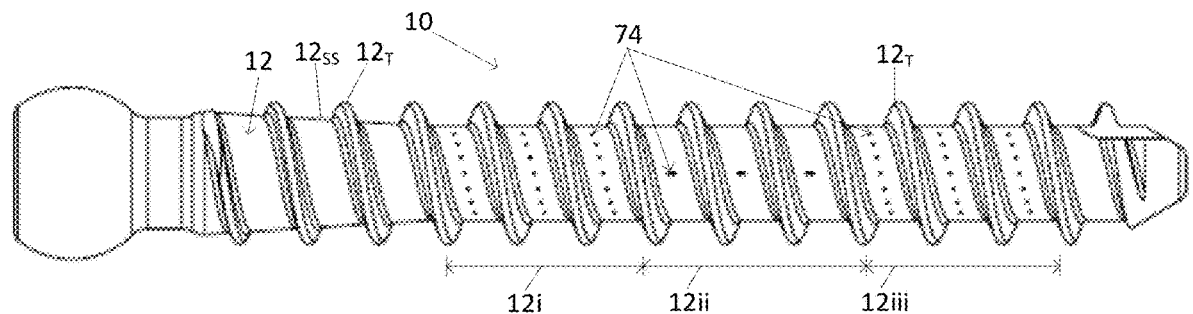
FIG. 18A illustrates a side view of a variation of an attachment device.

FIG. 18A illustrates that the device 10 can have fenestrations 74 with different sizes and shapes. For example, the device 10 can have one or multiple fenestrations 74 having a first shape $74_{S1}$ and one or multiple fenestrations 74 having a second shape $74_{S2}$ different from the first shape $74_{S1}$. FIG. 18A illustrates that the first shape $74_{S1}$ can be circular holes and the second shape $74_{S2}$ can be elongated slots. For example, the fenestrations 74 in the shaft first and third regions 12*i*, 12*iii* can have the fenestration first shape $74_{S1}$ and the fenestrations 74 in the shaft second region (e.g., between the shaft first and third regions 12*i*, 12*ii*) can have the fenestration second shape $74_{S2}$. Mixing different types of fenestrations 74 together on the same device 10 (e.g., based on size, shape and/or number) can allow for a unique and advantageous distribution of the fluid 96.

Figure 18B:
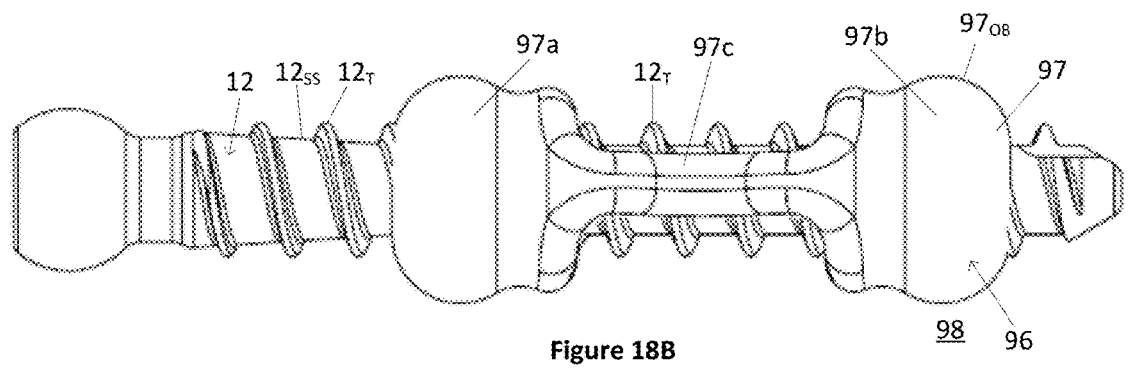
FIG. 18B illustrates a side view of a variation of a fluid distribution from fluid injected through the device of FIG. 18A.

FIG. 18B illustrates the fluid distribution 97 that can form when fluid is distributed through the device 10 of FIG. 18A. The fluid distribution 97 can have two ends 97*a* and 97*b* and a section 97*c* between the ends 97*a* and 97*b*. The first and second ends 97*a*, 97*b* can have a bulbous shape and the section 97*c* can have a flat shape.

Figure 18C:
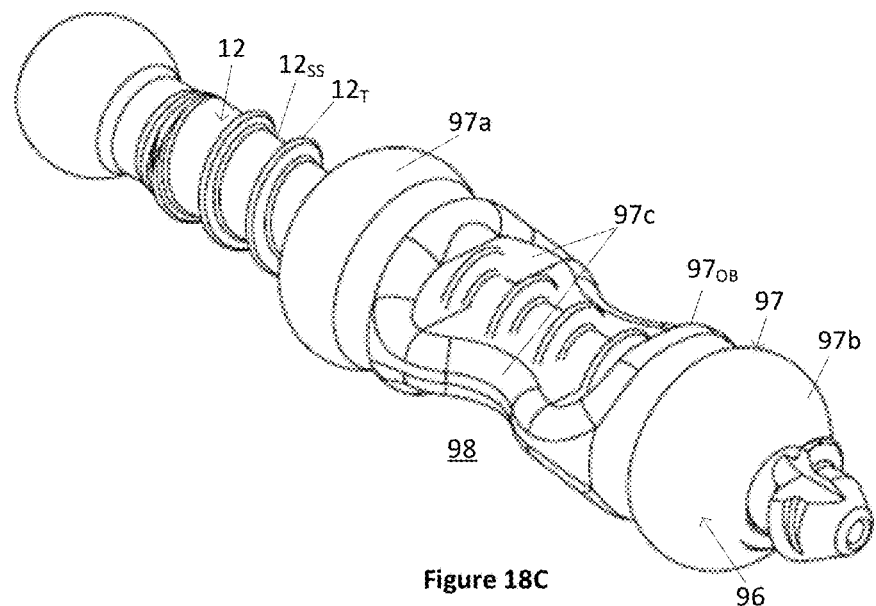
FIG. 18C illustrates a perspective view of a variation of a fluid distribution from fluid injected through the device of FIG. 18A.

FIG. 18C illustrates that the flat sections 97*c* and 97*d* can provide increased torque strength of the fluid 96 relative to the bone 98 (e.g., vertebral body).

Figure 19A:
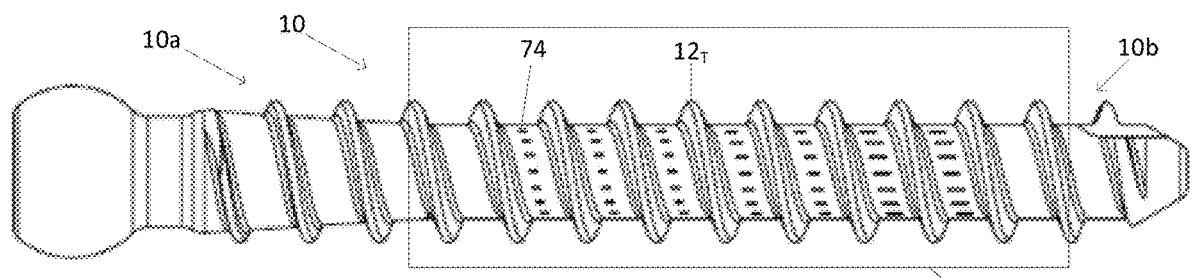
FIG. 19A illustrates a side view of a variation of an attachment device.

FIG. 19A illustrates that a flow gradient can be created by increasing the length of the fenestrations 74 proximal to distal along the device 10. Such an arrangement of the fenestrations can produce a uniform flow field away from the device when fluid is forced through the device 10. As another example, the fenestrations 74 can be arranged so that the flow field away from the device 10 can be non-uniform. Where a non-uniform flow field is desired, the number, size, shape and arrangement of fenestrations 74 can produce two or more flow rates away from the device or a flow field gradient away from the device that has a higher or lower flow rate away from the device 10 from one or more first fenestrations as compared to one or more second fenestrations. The fenestrations 74 can be holes or slots.

Figure 19B:
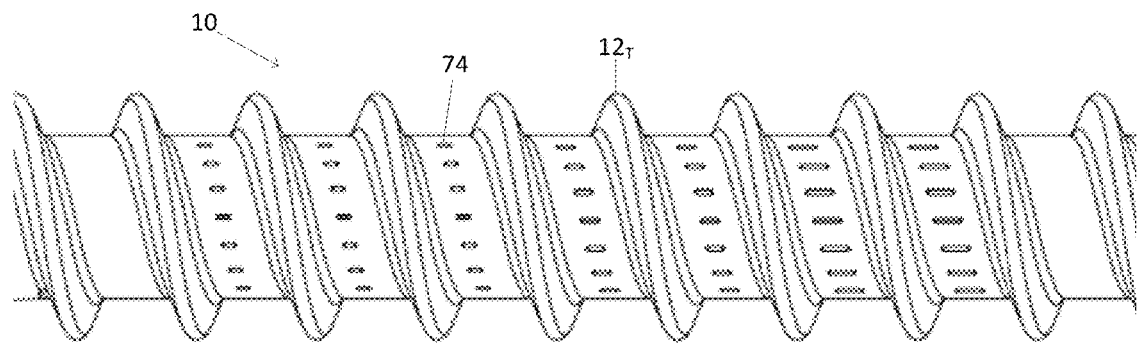
FIG. 19B is a magnified view of the attachment device of FIG. 19A at section 19B-19B.

FIG. 19B illustrates that the fenestrations can have a stadium shape.

Figure 20A:
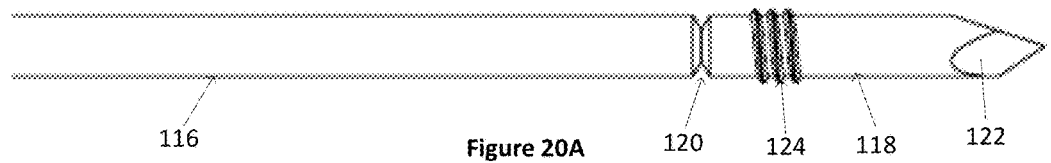
FIG. 20A illustrates a side view of a variation of a wire and a plug.

FIG. 20A illustrates a guide wire (e.g., K wire) 116 having a distal plug 118. The plug 118 can be integrated with or attached to the wire 116. The wire 116 can be a bone piercing shaft. For example, the wire 116 can be a bone spike such as the bone spike referred to elsewhere in this disclosure. The plug 118 can be attached to the device 10. The plug 118 can be attached to the device distal end 10*b*, for example, in the channel 45. The plug 118 can plug the device distal channel (e.g., channel 45) so that the fluid 96 cannot flow through the channel 45 when fluid is being distributed into the device 10 and through the fenestrations 74 into surrounding bone. The plug 118 can entirely block the flow of fluid through the device distal channel, or the plug 118 can have a fenestration (e.g., fenestration 74) that allows the fluid to flow through the device distal channel. Blocking the device distal channel 45 can allow a uniform flow field to form when the fluid 96 is forced through the device 10. The fenestration 74 in the plug 118 can reduce the flow rate through the device distal channel so that a uniform flow field is created. Additionally or alternatively, the device distal channel can be left open so that the fluid 96 can flow through it (e.g., channel 45). Fluid 96 can be delivered through the device 10 with or without the wire 116 in the channel 28.

The shaft of the wire 116 can have a break point 120. The break point 120 can extend partially or entirely around the circumference of the wire 120. The break point 120 can be a notch in the wire 116, for example, a circumferential notch. The notch can have a V-shape. The break point 120 (e.g., notch) can be a stress riser in the wire 116, for example, causing larger stresses to form in and near the notch as compared to other sections of the wire 116 when force is applied to the wire 116, for example, tensile force, compressive force, radial force, torsional force, or any combination thereof. The plug 118 can break off from the wire 116 at the break point 120 when a threshold force is applied to at the break point 120. The threshold force can be the result of torsion of the shaft of the wire 116.

The plug 118 can have a plug tip 122 that can pierce bone (e.g., bone 98). The plug tip 122 can be sharp. The plug tip 122 can have one or multiple cutting faces.

The plug 118 can have a plug engager 124. The plug engager 124 can be configured to engage with the device 10. The plug engager 124 can be on the plug proximal or distal end. FIG. 20A illustrates that the plug engager 124 can be screw threads or ribs. The plug engager 124 can be a bulge or protrusion on the shaft of the plug 118 to accommodate a friction or snap fit with a device engager attached to or integrated with the device 10. The device engager can be in the channel 45. The device engager can be in the shaft channel (e.g., channel 28). The plug engager 124 can removably or permanently engage with the device engager. The device engager can be threads on the interior of the distal end of the device (e.g., in the channel 28, in the channel 45). The device engager can be screw threads, or can be a male or female portion configured to receive or engage with the plug engager 124, for example, ribs.

In use, the wire 116 can be inserted into bone (e.g., bone 98). For example, the wire 116 can be inserted through a pedicle and into the vertebral body, and can continued to be inserted until the correct depth is confirmed (e.g., with imaging). The device 10 can then be put over (e.g., slid over) the wire 116 and the device 10 can be screwed into the vertebral body to the correct depth. The wire 116 can be in the cannulated channel of the device when the device 10 is being put over the wire. The wire 116 can then be pulled back into the device 10. Once the plug engager 124 meets or engages with the device engager (e.g., when their respective threads meet, when their respective ribs meet), the wire 116 can be removably attached to the device 10 via engagement between the plug and device engagers. A torsional force, longitudinal force, or both can then be applied to the shaft of the wire 116, for example, to screw the plug engager 124 threads to the device engager threads. This can break the wire 116 at the break point 120, leaving the plug 118 in the device 10. The wire 116 can then be withdrawn from the device 10, leaving the plug 118 in place. Once the wire 116 is removed, the fluid can be injected into the device 10.

Figure 20B:
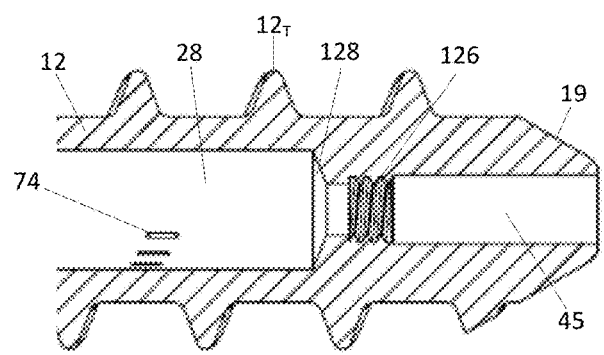
FIG. 20B illustrates a cropped longitudinal cross-sectional view of a variation of an attachment device.

FIG. 20B illustrates that the device 10 can have a device engager 126. The plug and device engagers 124, 126 can be engaged with one another, for example, via a screw fit, friction fit, snap fit, magnetic fit, glue fit, or any combination thereof.

FIG. 20B further illustrates that the internal channel (e.g., channel 28) can taper toward the channel 45, for example, in taper region 128. The taper region 128 can create a space for the wire 116 to deflect, bend, break, or deform into when the plug 118 is detached from the wire 116.

FIG. 20B further illustrates a configuration of the device 10 before the device 10 is inserted over the wire 116 and attached to tissue (e.g., bone).

Figure 20C:
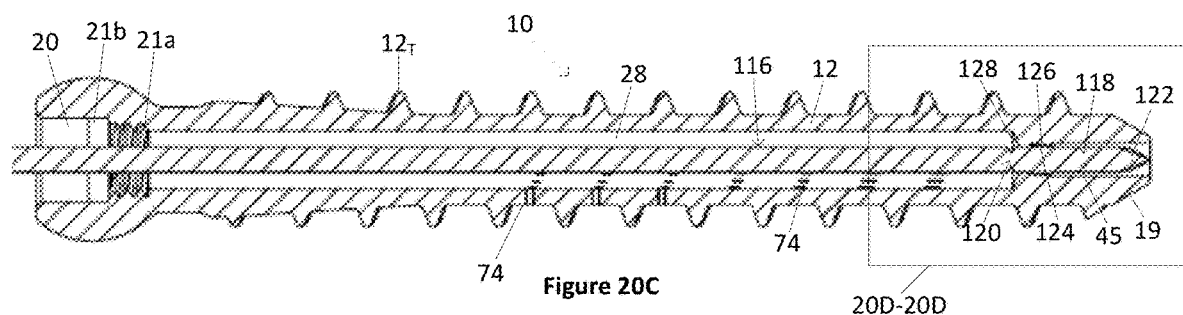
FIG. 20C illustrates a variation longitudinal cross-sectional view of the attachment device of FIG. 20B with the wire and plug of FIG. 20A in the attachment device.

FIG. 20C illustrates that the plug and device engagers 124, 126 can be connected to one another, for example, with a screw fit. The plug 118 can be translated and/or rotated distally past the device engager 126 such that some or all of the plug and/or some of the wire 116 extends out of the device 10. For example, the device engager 126 can allow the plug engager 124 to move past the device engager 126 in a first longitudinal direction but not in a second longitudinal direction opposite the first longitudinal direction. As another example, the device engager 126 can resist movement of the plug engager 124 past the device engager 126 less in the first longitudinal direction than in the second longitudinal direction. The first longitudinal direction can be a proximal to distal direction. The second longitudinal direction can be a distal to proximal direction. As yet another example, the plug engager 124 can be prevented from moving past the device engager 126 in the first longitudinal direction such that the tip 122 is prevented from extending past the tip 19 as shown in FIG. 20C or so that only the tip 122 can be translated out of the channel 45 and function as an anterior cortical purchase.

Figure 20D:
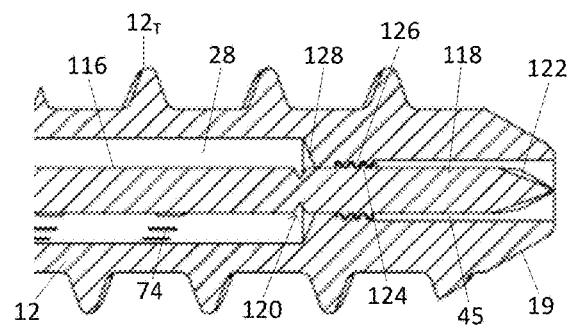
FIG. 20D is a magnified view of the attachment device of FIG. 20C at section 20D-20D.

FIG. 20D again illustrates that the wire 116 can be threaded into the device 10, for example, via the plug and device engagers 124, 126. FIG. 20D further illustrates that the device tip 19 can be flush with the wire tip 122 when the plug engager 124 is engaged with the device engager 126. For example, the distal terminal end of the device tip 19 can be flush with the distal terminal end of the wire tip 122. As another example, the device tip 19 can extend out of the channel 25 and beyond the terminal distal end of the device tip 19 when the plug and device engagers 124, 126 are engaged with one another.

Figure 20E:
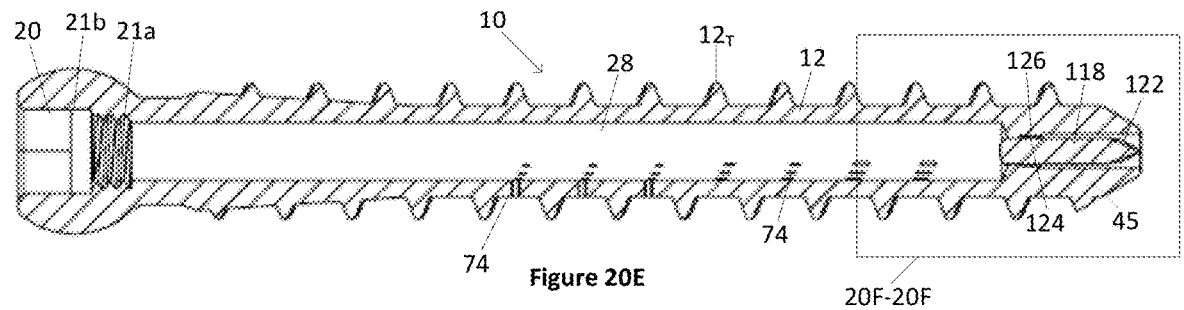
FIG. 20E illustrates a variation longitudinal cross-sectional view of the attachment device of FIG. 20C with the plug in the attachment device.

FIG. 20E illustrates the wire 116 broken at the break point 120, leaving the plug 118 attached to the device 10. For example, FIG. 20E illustrates the wire and device assembly 116, 10 after the proximal end of the wire 116 is snapped (e.g., radially snapped) and removed. The plug 118 can prevent fluid (e.g., fluid 96) from flowing through the channel 45.

Figure 20F:
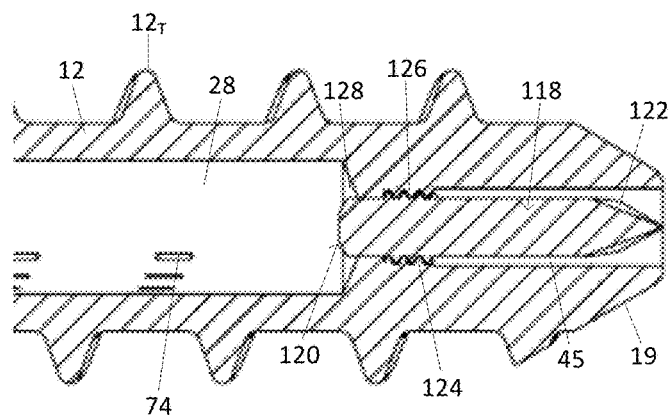
FIG. 20F is a magnified view of the attachment device of FIG. 20E at section 20E-20F.

FIG. 20F illustrates that the plug 118 can remain attached to the device 10 when the wire 116 is detached proximal the break point 120.

Figure 21A:
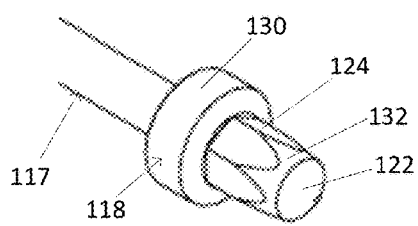
FIG. 21A illustrates a perspective view of a variation of a wire and a plug.

FIG. 21A illustrates a wire 117 with the plug 118. The wire 117 can be inserted into the device 10 after the wire 116 is removed. The wire 117 can be cannulated such that it can be slid over wire 116 when the wire 116 is in the device 10. The plug 118 can be cannulated such that it can be slid over the wire 116 when the wire 116 is in the device 10. As another example, the wire 117 can be the same as the wire 116 such that FIG. 21A illustrates another variation of a wire and plug 116, 118.

FIG. 21A further illustrates that the plug 118 can have a collar 130, that the plug engager 124 can have hex feature configured to engage with one or multiple corresponding flat surfaces (e.g., a corresponding hex feature) of the device engager 126, that the plug tip 122 can include a taper 132 configured to engage with the tapered region 128 of the device 10 to guide the plug 118 into the device distal channel without breaking the plug 118 from the break point 120, that the terminal distal end of the plug tip 122 can be a flat surface perpendicular to or at a non-perpendicular angle with the device longitudinal axis $8_L$, or any combination thereof. The terminal distal end of the plug tip 122 can be a blunt tip or a sharp tip. Additionally or alternatively, the collar 130 can be the plug engager 124 and can engage with a distal end of the device internal channel (e.g., channel 28) with a screw fit, friction fit, snap fit, magnetic fit, glue fit, or any combination thereof.

Figure 21B:
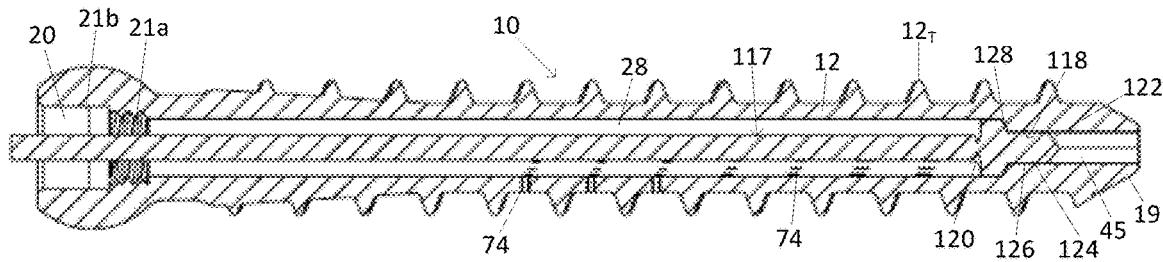
FIG. 21B illustrates a longitudinal cross-sectional view of a variation of an attachment device with the wire and plug of FIG. 21A in the attachment device.

FIG. 21B illustrates that the wire 117 having the plug 118 can be inserted into the device 10 after the wire 116 with or without a bone spike is removed from the device 10. FIG. 21B further illustrates that the plug and device engagers 124, 126 can be connected to one another, for example, with a friction fit between the hex features of the plug and device engagers 124, 126. Additionally or alternatively, FIG. 21B further illustrates that the collar 130 can engage with a tapered portion of the channel 28 to form a friction fit between the plug 118 and the device 10.

Figure 21C:
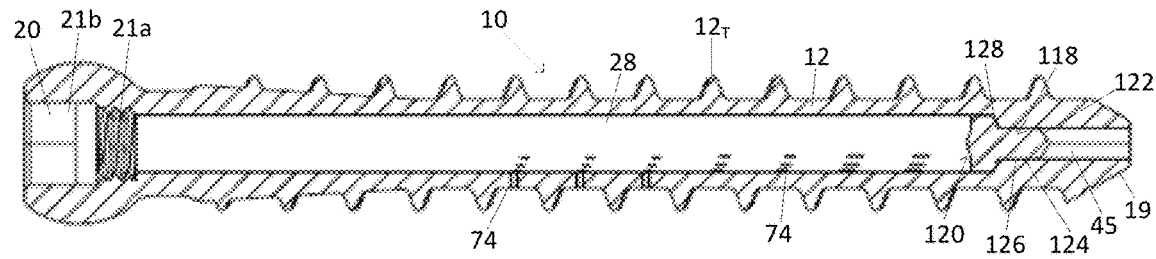
FIG. 21C illustrates a variation longitudinal cross-sectional view of the attachment device of FIG. 21B with the plug in the attachment device.

FIG. 21C illustrates the wire 117 broken at the break point 120, leaving the plug 118 attached to the device 10. For example, FIG. 21C illustrates the wire and device assembly 117, 10 after the proximal end of the wire 117 (e.g., the portion proximal to the plug engager 124) is snapped and removed. As another example, FIG. 21C illustrates the wire and device assembly 116, 10 after the proximal end of the wire 116 (e.g., the portion proximal to the plug engager 124) is snapped and removed. The plug 118 can prevent fluid (e.g., fluid 96) from flowing through the channel 45 from inside to outside the device 10, from outside to inside the device 10, or both. FIG. 21C further illustrates that the plug tip 122 can be tapered and have a distal terminal point.

Figure 22A:
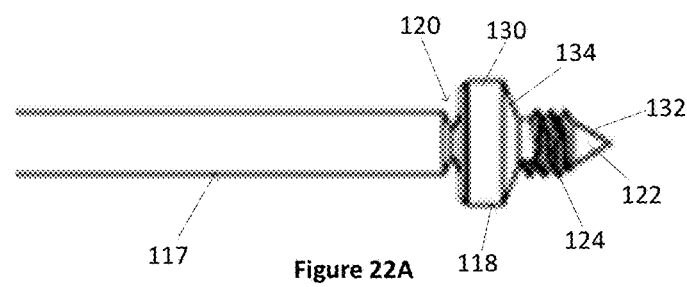
FIG. 22A illustrates a perspective view of a variation of a wire and a plug.

FIG. 22A illustrates that the plug 118 can have a tapered region 134 configured to engage with the tapered region 128 of the device 10. When the plug 118 is attached to the device 10, the plug tapered region 134 can be seated in the device tapered region 128. When the plug 118 plugs the device 10, the plug tapered region 134 can be seated in the device tapered region 128.

FIG. 22A further illustrates that the plug engager 124 can be threaded. The plug engager 124 can be threaded with internal threads of the device 10, for example, threads of the device engager 126.

Figure 22B:
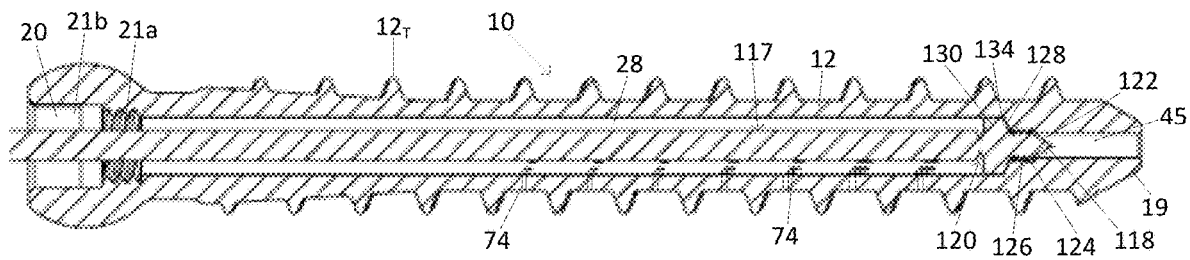
FIG. 22B illustrates a longitudinal cross-sectional view of a variation of an attachment device with the wire and plug of FIG. 22A in the attachment device.

FIG. 22B illustrates that the wire 117 having the plug 118 can be inserted into the device 10 after the wire 116 is removed from the device 10. FIG. 22B further illustrates that the plug and device engagers 124, 126 can be connected to one another, for example, with a screw fit via the threads of the plug and device engagers 124, 126. Additionally or alternatively, FIG. 22B further illustrates that the collar 130 e.g., the plug tapered region 134) can engage with the device tapered portion 128 with a friction fit, snap fit, magnetic fit, glue fit, or any combination thereof.

The plug 118 can be integrated with or attached to the wire 116 or to the wire 117. For example, the plug 118 can be inserted into and attached to the device 10 after the wire 116 is removed such that the plug 118 is not attached to or integrated with the wire 116, but rather attached to a separate wire or insertion tool that can be inserted into the device 10 once the wire 116 is removed (e.g., wire 117). The separate wire or insertion tool (e.g., wire 117) can leave the plug 118 in place engaged with the device engager 126 when the separate wire or insertion tool is removed from the device 10. The first wire (e.g., 116) can have a bone spike. The first wire 116, second wire 117, or both can be cannulated. The plug 118 can be cannulated or not cannulated. As yet another example, the plug 118 can be inserted over the wire 116 before the wire 116 is removed from the device 10, for example, when the device 10 is in the desired location in the bone (e.g., vertebral body).

Figure 23:
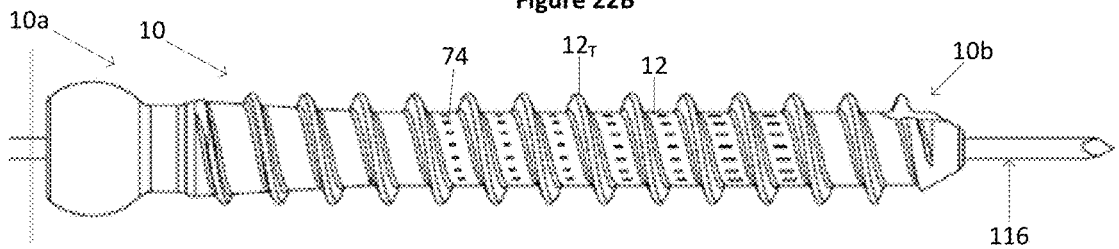
FIG. 23 illustrates a side view of a variation on an attachment device inserted over a wire.

FIG. 23 illustrates the device 10 (e.g., the device 10 of FIGS. 19A-22B, or of any other figure) inserted over the wire 116. The wire 116 can have the plug 118. As another example, the wire 116 does not have the plug 118.

FIG. 23 further illustrates that the fluid 96 can be injected into the device 10 while the device 10 is on the wire 116.

Figure 24A:
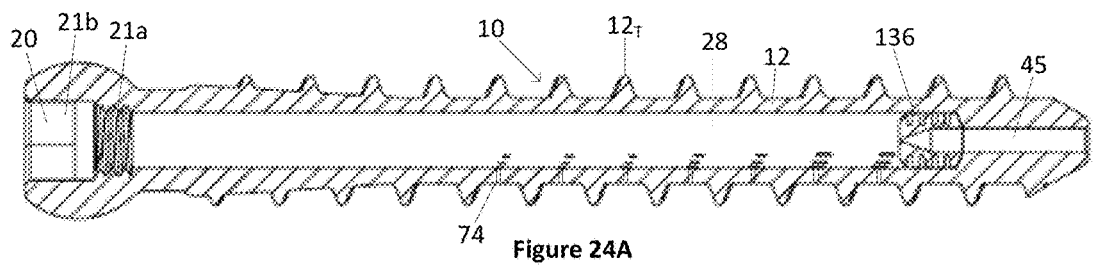
FIG. 24A illustrates a longitudinal cross-sectional view of a variation of an attachment device having a valve.

FIG. 24A illustrates that the device 10 can have a check valve 136. The check valve 136 can be an internal passive check valve. The check valve 136 can be an injection molded polyurethane check valve. The check valve 136 can be in the device 10 (e.g., in the channel 28). For example, the check valve 136 can be positioned in the distal end of the device cannula 28 or in the channel 45, for example, at the distal end of the channel 45. The check valve 136 allows the device 10 to pass over the wire 116, allows the wire 116 to be removed and stops fluid from passing into the channel 28 through the channel 45 when the wire 116 is removed (e.g., withdrawn) from the device 10. In this way, the check valve 136 can function as a fluid plug (e.g., plug 118).

Figure 24B:
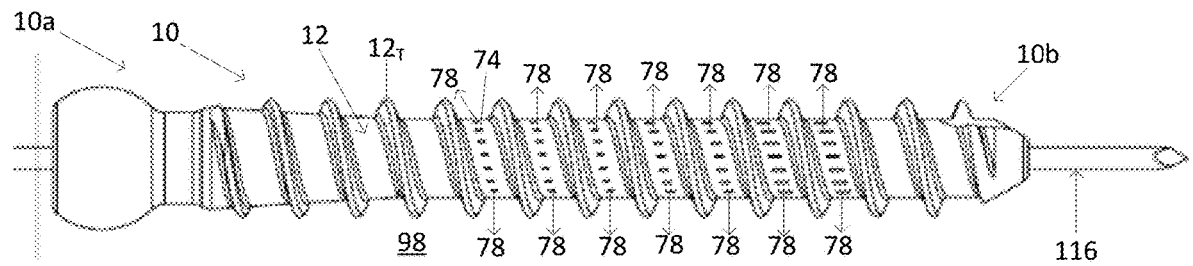
FIG. 24B illustrates a side view of the attachment device of FIG. 24A when fluid is injected through the attachment device.

FIG. 24B illustrates that the fluid 96 can flow through the device 10 when the device 10 is removably attached to the wire 116, as indicated by flow arrows 78. As another example, the fluid 96 can flow through the device 10 after the wire 116 and/or the wire 117 are removed from the device 10, as indicated by flow arrows 78. The arrows 78 are exemplary; the fluid can flow out of some or all of the fenestrations 74 of any of the devices 10 disclosed, contemplated or illustrated herein. As another example, FIG. 24B illustrates that the fluid 96 can flow through the device 10 after the wire 116 is partially or entirely withdrawn from the device 10. The flow is indicated by flow arrows 78.

Figure 25A:
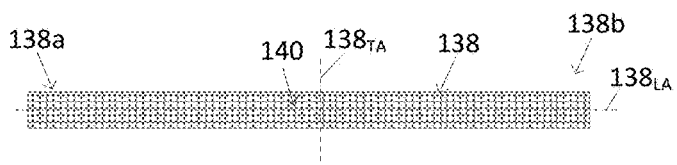
FIG. 25A illustrates a schematic of a variation of a muffler.

FIG. 25A illustrates a variation of a muffler 138. The muffler 138 can have a muffler proximal end 138a and a muffler distal end 138b. The muffler 138 can be cannulated. The muffler 138 can be a rigid or flexible tube. The tube can be a mesh, a shaft, or both. The muffler 138 can be a liner, an insert, a sleeve, a needle, or any combination thereof.

The muffler 138 can be attached to or integrated with the device 10. The muffler 138 can be attached to or integrated with a conventional attachment device (e.g., with a conventional pedicle screw). The device 10 and the conventional attachment device are both referred to as the device for ease of reference herein. While conventional devices are also referred to as devices 200, any reference to a device 200 is also a reference to any of the devices 10. Similarly, any reference to a device 10 is also a reference to any of the devices 200. The muffler 138 can be permanently or removably inserted in, attached to, or integrated with the device 10, for example, in the device channel (e.g., channel 28). The muffler 138 can be live within the device 10, it can be inserted into the device 10 when needed, or it can be part of the fluid injection system. The muffler 138 can be live within the device 10, it can be inserted into the device 10 when needed, or it can be part of the device delivery system. The muffler can be made of fabric, metal, polymer (e.g., plastic), composite material, or any combination thereof. For example, the muffler 138 can be made of steel, titanium, nickel-titanium (e.g., Nitinol), platinum (Pt), polyethylene terephthalate (PET), polypropylene (PP), polytetrafluoroethylene (PTFE), nylon, or any combination thereof.

The muffler 138 can be a flow controller. The muffler 138 can be a flow restrictor. The fluid 96 can be injected through the muffler 138, for example, when the muffler 138 is in the device 10. The muffler 138 can be porous to control the flow of fluid through the muffler 138. The distal tip of the muffler 138 can be closed so that the injected fluid can flow through the device fenestrations (e.g., fenestrations 74) and not out the device distal tip (e.g., through channel 45). Closing the muffler tip can be accomplished by crimping the tube tip, plugging the tip, tapering the fabric versions to a jammed condition with limited or no permeability, or any combination thereof.

The muffler 138 can be porous to control the fluid injection into bone through the device 10, through conventional porous attachment devices (e.g., existing fenestrated bone screws), or both. For example, the muffler 138 can have muffler fenestrations 140. The fenestrations 140 can be flow channels (e.g., microfluidic channels) within the muffler wall. The fenestrations 140 can be cells in a mesh. The fenestrations 140 can create predictive fluid flow per unit time through the muffler 138 so that the flow through the device fenestrations is controlled. The fenestrations 74 can limit, regulate and control fluid flow through the device 10. The muffler 138 can limit, regulate and control fluid flow through the device 10, for example, through the fenestrations 74. For example, flow through the fenestrations in conventional devices can be limited, regulated and controlled via limited, regulated and controlled fluid flow through the muffler 138.

The muffler 138 can prevent uncontrolled jetting and high flow rates through the device fenestrations and into low resistive voids in bone, for example, by controlling the flow of fluid through the device 10 and/or through conventional devices. The muffler 138 can create a uniform flow field through the device fenestrations (e.g., fenestrations 74) to create the fluid distribution 97. The muffler 138 can create a restrictive path for the fluid 96 to flow through before flowing through the device fenestrations (e.g., fenestrations 74 or fenestrations in conventional devices). The restrictive path can be straight or tortuous. The muffler 138 can inhibit or prevent the formation of non-uniform flow through the device fenestrations.

The muffle 138 (e.g., via the restrictive microfluidic path) can control the fluid mechanics and fluid dynamics properties of and through the device 10. The fluid mechanic properties can include the fluid flow rate and the fluid flow pressure. The combination and control of such properties can produce a controllable flow gradient in which the fluid 96 can controllably flow through the device fenestrations. The muffler 138 can create a uniform flow field through the attachment devices 10 as opposed to the non-uniform flow fields associated with conventional devices (e.g., caused by paths of least resistance in bone and device fenestrations not sized, shaped, or arranged to provide uniform flow fields in nonhomogeneous bone). Fluid distributions 97 of various shapes can created by controlling the flow through the device 10, through conventional devices, or both, for example, with different numbers, sizes, shapes and/or densities of device fenestrations 74 and/or of muffler fenestrations 140.

When conventional attachment devices are placed in nonhomogeneous bone (e.g., bone having non-uniform porosity, gaps, holes, cracks, for example, from osteoporosis), the flow through the device fenestrations can be non-uniform since the fluid can follow the path of least resistance. When conventional attachment devices having the muffler 138 are placed in nonhomogeneous bone, the fluid 96 can flow through each device hole in a uniform manner (e.g., uniform flow rate, uniform flow pressure). The muffler 138 can regulate the flow through the device fenestrations (e.g., of conventional attachment devices) to inhibit or prevent non-uniform fluid flow (e.g., jetting). The muffler 138 can inhibit or prevent paths of least resistance in bone from affecting the flow of fluid through the device fenestrations. In this way, uniform fluid distributions (e.g., distributions 97) can advantageously be created using conventional attachment devices with the muffler 138. The term device fenestrations includes, for example, device fenestrations 74 and conventional device fenestrations.

The fenestrations 140 can have a size and shape that can provide fluid flow rates and fluid flow pressures that eliminate or inhibit unregulated fluid flow into cracks and fissures in bone. The fenestrations 140 can have a size and shape so that a uniform flow field through the device fenestrations (e.g., fenestrations 74, conventional device fenestrations) is created when fluid is injected through the muffler 138 when the muffler 138 is in the device. The fenestrations 140 can be arranged so that a uniform flow field is created when fluid is injected through the device. This uniform flow field can create the fluid distribution 97. As another example, the fenestrations 140 can be arranged so that multiple (e.g., 2, 3, 4, 5, 6, or more) uniform flow fields are created when fluid is injected through the device. These multiple flow fields can create fluid distributions 97 having various shapes.

The fenestrations 140 can provide resistance to flow through the device. The fenestrations 140 can provide uniform or non-uniform resistance to flow along the length of the device. The resistance can create a uniform flow field through the fenestrations 140 when fluid is injected through the muffler 138 such that the muffler 138 determines the flow rate through the device fenestrations. For example, when the device is implanted into nonhomogeneous bone (e.g., osteoporotic bone, bone having holes, bone having cracks) and fluid (e.g., anchoring fluid) is injected through the device, the fluid can flow through each hole 140 in a uniform manner (e.g., uniform flow rate, uniform flow pressure) such that the fenestrations 140 create uniform fluid flow along the length of the device.

The size and shape of the fenestrations 140 can control the flow of fluid through the device fenestrations (e.g., fenestrations 74, conventional fenestrations). The muffler fenestrations 140 can have a size and shape that provide a flow rate and a flow pressure when fluid is delivered through the fenestrations 140, for example, with a constant or variable delivery force. The flow rate can be constant, or can depend on the force at which fluid is injected into the muffler 140. The flow rate through all the fenestrations 140 can be the same for any given fluid delivery force into the device. The flow pressure can be constant, or can depend on the force at which fluid is injected into the muffler 138. The flow pressure through all the fenestrations 140 can be the same for any given fluid delivery force into the device 10. The flow rate through the muffler 138 can be, for example, from about 0.25 cubic centimeters per second to about 3.00 cubic centimeters per second, or more narrowly, from about 0.80 cc/s to about 1.25 cc/s, including every 0.05 cc/s increment within these ranges (e.g., 0.50 cc/s, 0.80 cc/s, 1.00 cc/s, 1.25 cc/s). These flow rates can be muffler threshold flow rates. As another example, the flow rate through the muffler 138 can be, for example, from about 0.25 cc/min to about 3.00 cc/min, or more narrowly, from about 0.80 cc/min to about 1.25 cc/min, including every 0.05 cc/min increment within these ranges (e.g., 0.50 cc/min, 0.80 cc/min, 1.00 cc/min, 1.25 cc/min). These flow rates can be muffler threshold flow rates.

The flow rate through each of the fenestrations 140 (e.g., on a per fenestration basis) can be about 0.01 cc/s to about 0.50 cc/s, including every 0.01 cc/s increment within this range (e.g., 0.1 cc/s), or more narrowly, from about 0.005 cc/s to about 0.0250 cc/s, including every 0.001 cc/s increment within this range (e.g., 0.016 cc/s). These flow rates can be threshold flow rates. Where the muffler 138 has fenestrations 140 with a single size, the fenestration flow rate can be determined by dividing the muffler flow rate by the number of fenestrations 140. For example, where the muffler 138 has 30 uniformly sized fenestrations 140 and the muffler flow rate is about 0.5 cc/s, the flow rate through each of the fenestrations 140 can be about 0.016 cc/s (e.g., 0.5 cc/s/30 fenestrations 140). Where the muffler 138 has fenestrations 140 of different sizes (e.g., two, three, four, five or more sizes), the flow rate through the differently sized fenestrations 140 can be the same or different from one another. For example, the fenestrations 140 of the muffler 138 can include a muffler first fenestration and a muffler second fenestration smaller than the muffler first fenestration. The muffler first fenestration can be proximal to the muffler second fenestration, distal to the muffler second fenestration, or even with the muffler second fenestration. The flow rate through the muffler first fenestration can be the same, larger than, or less than the flow rate through the muffler second fenestration. For example, the flow rate through the muffler first fenestration can be about 0.01 cc/s to about 0.50 cc/s, including every 0.01 cc/s increment within this range (e.g., 0.1 cc/s), or more narrowly, from about 0.005 cc/s to about 0.0250 cc/s, including every 0.001 cc/s increment within this range (e.g., 0.016 cc/s). The flow rate through the muffler second fenestration can be about 0.01 cc/s to about 0.50 cc/s, including every 0.01 cc/s increment within this range (e.g., 0.1 cc/s), or more narrowly, from about 0.005 cc/s to about 0.0250 cc/s, including every 0.001 cc/s increment within this range (e.g., 0.016 cc/s). The foregoing flow rates can be muffler fenestration threshold flow rates.

The fluid delivery pressure through the muffler (also referred to as the muffler pressure) can be, for example, from about 400 psi to about 2000 psi, including every 100 psi range within this range, including every 1 psi increment within these ranges, or any combination thereof (e.g., about 450 psi). These pressures can be threshold pressures. For example, a 5 cc syringe can be capable of producing 450 psi of pressure. The fluid delivery pressure can be uniform through the fenestrations 140 or can depend on the size and shape of the fenestrations 140 where the muffler 138 has fenestrations 140 of different sizes. For example, the fluid delivery pressure through the muffler first fenestration can be the same, larger than, or less than the fluid delivery pressure through the muffler second fenestration.

The fenestrations 140, by providing a uniform resistance to flow exiting the muffler 138, can eliminate or reduce the effects of paths of less resistance in bone (e.g., areas having imperfections, compromised areas, weak areas, non-homogeneous areas, areas with cracks, areas with osteoporotic bone) so that the fluid 96 can flow uniformly through the device fenestrations, so that the fluid flow out of any one of the device fenestrations (e.g., as measured by flow rate or flow pressure) does not exceed about 5% to about 100% of the fluid flow out of any other of the device fenestrations, so that the fluid flow out of the device fenestrations (e.g., as measured by flow rate or flow pressure) is within a 5% to 20% tolerance of a target flow value associated with a given delivery force, or so that any combination of these three metrics for the flow of fluid out of the device (e.g., device 10, conventional device) is satisfied or intentionally approximated. The percentage ranges in this paragraph can include any 1% increment within these ranges.

The controlled flow through the fenestrations 140, and subsequently through the device fenestrations, can create a uniform fluid region (e.g., region 97) partially or entirely around the device in homogeneous bone, non-homogeneous bone, or both. For example, the uniform flow region 97 can have the shapes disclosed herein. For devices where the fluid flow out of the device is not controlled (e.g., for conventional devices), the flow rate out of some device fenestrations may be greater than other device fenestrations such that the fluid flows out of the device at a greater rate near paths of less resistance in the bone. The fenestrations 140 can be sized and shaped to prevent larger flow rates in or near paths of less resistance, for example, by controlling the flow rate and flow pressures through the device fenestrations. The muffler 138 can create a controlled flow and pressure gradient.

FIG. 25A further illustrates that the muffler 138 can have muffler longitudinal and transverse axes $138_{LA}$ and $138_{TA}$. The axes $138_{LA}$ and $138_{TA}$ can be straight or curved. The axes $138_{LA}$ and $138_{TA}$ can be perpendicular to one another. The axis $138_{LA}$ can be a center longitudinal axis of the muffler 138 or can be a longitudinal axis offset from the center longitudinal axis. The axis $138_{TA}$ can be a center transverse axis of the muffler 138 or can be a transverse axis offset from the center transverse axis.

The muffler 138 can be rigid, flexible, deformable, or any combination thereof. The muffler 138 can be expandable and/or contractible along the axis $138_{LA}$, $138_{TA}$, or both. The muffler can have a fixed length.

The muffler 138 can be a tube with a micro pattern of fenestrations 140. The muffler 138 can be a laser tube.

The muffler 138 can be a fabric tube, for example, a woven sleeve, a braided sleeve, or both.

The muffler 138 can be a single or multiple layer tube. The muffler 138 can be a single tube or multiple tubes. For example, the muffler 138 can be a telescopable muffler 138 having two or more tubes (e.g., 2, 3, 4, 5, 6, or more tubes). A telescopable muffler 138 can advantageously allow the muffler 138 to have an adjustable size (e.g., adjustable length). As another example, the telescopable muffler 138 can have an adjustable flow rate. For example, where the muffler 138 has three tubes, the muffler 138 can be adjusted between first, second and third flow rates, where the first flow rate can be when a first tube is extended distal to the second and third tubes, the second flow rate can be when the first tube is inside or over the second tube, and the third flow rate can be when the first and second tubes are inside or over the third tube. The first flow rate can be greater than the second flow rate and the second flow rate can be greater than the third flow rate. As another example, the muffler 138 can be telescopable such that the flow through the muffler 138 is the same for any length of the muffler. This can advantageously allow the muffler 138 to be used with devices having different lengths.

The muffler 138 and the muffler fenestrations 140 can have any of the same or different properties as the device 10 and device fenestrations 74 described, contemplated or illustrated herein with reference to, for example, FIGS. 1A-24B, including the size, shape, number and arrangement (e.g., gradient and non-gradient arrangements) of the device fenestrations 74.

The muffler 138 can have controlled porosity.

The muffler 138 can have a gradient, for example, a proximal to distal permeability increase, or vice versa.

The muffler 138 can stand within the inner cannulation of the device.

The muffler 138 can have a column strength that can resist the flow of the fluid 96 (e.g., bone cement) through the fenestrations 140. The fluid 96 can flow through the fenestrations 140 with or without deforming the fenestrations 140.

The muffler 138 can be press fit or slip fit into the device channel. The muffler 138 can be self-expanding (e.g., grip inner device wall) into the device.

Figure 25B:
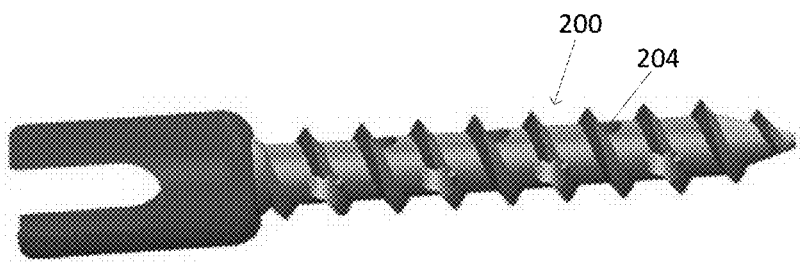
FIG. 25B illustrates a variation of a conventional attachment device.
Figure 25C:
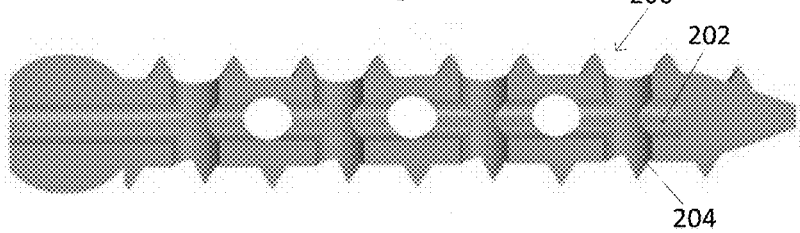
FIG. 25C illustrates a variation of a longitudinal cross-sectional view of the attachment device of FIG. 25B.
Figure 25D:
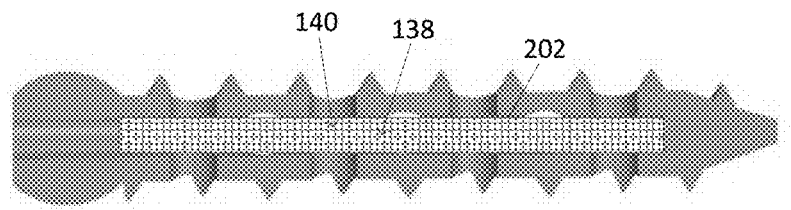
FIG. 25D illustrates the attachment device of FIG. 25C with the muffler of FIG. 25A inserted into the attachment device.

The muffler 138 can be used with a specifically designed cannulated/fenestrated attachment device (e.g., device 10) or it can be used with any off the shelf bone cement injectable screw. For example, FIGS. 25B and 25C illustrate a conventional attachment device 200 having a cannulation 202 (also referred to as a device channel) and conventional fenestrations 204. FIG. 25D illustrates that the muffler 138 can be removably or permanently attached to the device (e.g., device 10, device 200) in the device channel (e.g., channel 28, channel 202) to control and regulate the flow of fluid out of the device 200 through the device fenestrations 204. The muffler 138 can be insertable into the devices (e.g., 10 and 200). The muffler 138 can be detachable from the devices. The muffler 138 can be permanently attached to the devices. The muffler 138 can be removably attachable to the devices. For example, the muffler 138 can be removably attached to the devices and not be removed from the device after the fluid 96 is delivered. As another example, the muffler 138 can be removably attached to the devices and be removed from the device after the fluid 96 is delivered. As yet another example, the muffler 138 can be removably attached to the devices and be implanted with the devices.

Figure 26A:
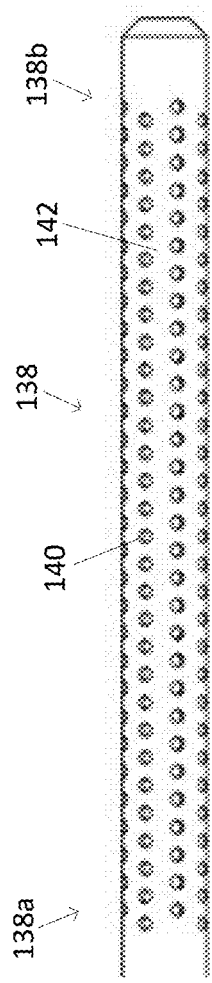
FIG. 26A illustrates a side view of a variation of a muffler.

FIG. 26A illustrates that the muffler fenestrations 140 can be circular and that the muffler 138 can have a muffler wall 142.

FIG. 26A further illustrates that the muffler can be non-threaded; however, the outer surface of the muffler 138 can have screw threads configured to engage with screw threads on the inner surface of the device channel (e.g., channel 28, channel 202).

FIG. 26A further illustrates that that the muffler 138 can be a live-in liner. The muffler 138 can remain in the device (e.g., device 10, device 200) after the device is implanted and fluid 96 is injected into the bone.

Figure 26B:
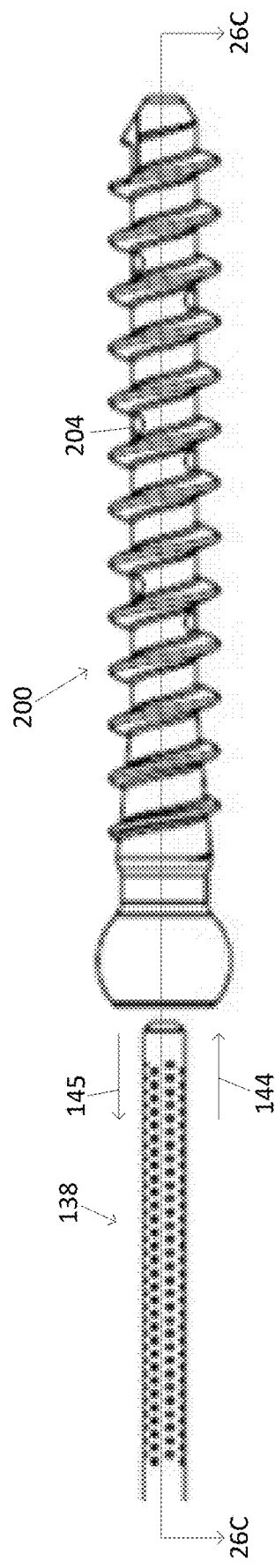
FIG. 26B illustrates the muffler of FIG. 26A and a variation of an attachment device.

FIG. 26B illustrates that that the muffler 138 can be inserted into the device (e.g., device 10, device 200), as indicated by arrow 144. The muffler 138 can be translated into the device channel (e.g., channel 28, channel 202), rotated into the device channel, or both. The muffler 138 and the device can be engaged with one another, for example, via a screw fit, friction fit, snap fit, magnetic fit, glue fit, loose fit, or any combination thereof.

FIG. 26B further illustrates that that the muffler 138 can be removed from the device (e.g., device 10, device 200) after being inserted into it, as indicated by arrow 145. The muffler 138 can be translated out of the device channel (e.g., channel 28, channel 202), rotated out of the device channel, or both.

Figure 26C:
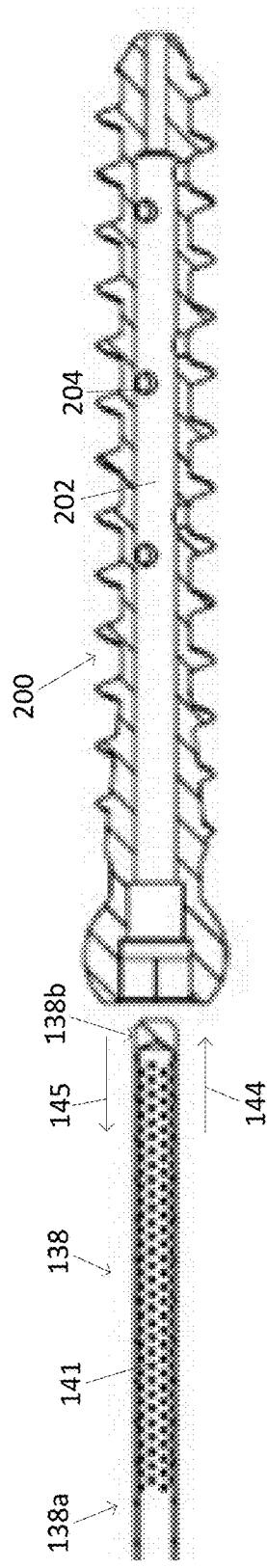
FIG. 26C illustrates a variation of a longitudinal cross-sectional view of the muffler and attachment device of FIG. 26B taken along line 26C-26C.

FIG. 26C illustrates that the distal terminal end of the muffler 138 can be closed and that the muffler 138 can have a muffler channel 141.

FIGS. 26B and 26C illustrate that the muffler 138 can be inserted into any variation of a conventional device 200. The muffler 138 can be permanently or removably inserted into the device 200, as indicated by arrow 144. As another example, the muffler 138 can be removed from the device 200 after fluid is delivered through the muffler and device 138, 200 into bone near the device 200, as indicated by arrow 145. The fluid in the bone can have the fluid distribution 97.

Figure 26D:
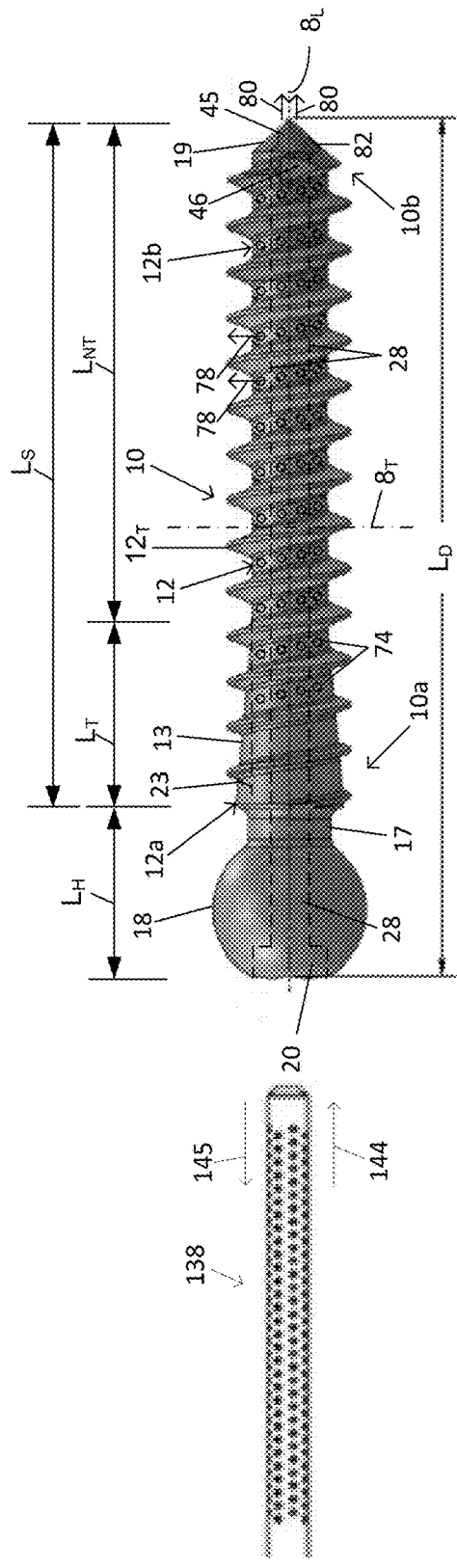
FIG. 26D illustrates the muffler of FIG. 26A and the attachment device of FIG. 1A.
Figure 26E:
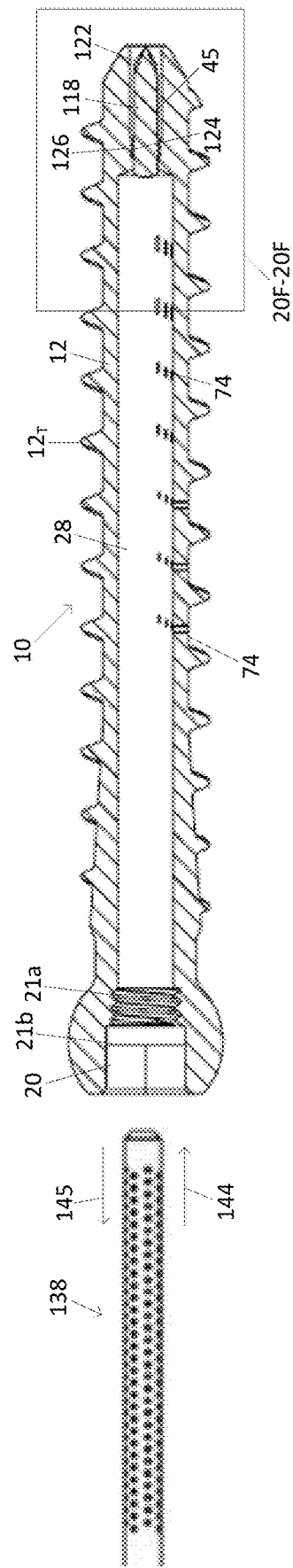
FIG. 26E illustrates the muffler of FIG. 26A and the attachment device of FIG. 20E.

FIGS. 26D and 26E illustrate that the muffler 138 can be inserted into any variation of the device 10. The muffler 138 can be permanently or removably inserted into the device 10, as indicated by arrow 144. As another example, the muffler 138 can be removed from the device 10 after fluid is delivered through the muffler and device 138, 10 into bone near the device 10, as indicated by arrow 145. The fluid in the bone can have the fluid distribution 97.

Figure 27A:
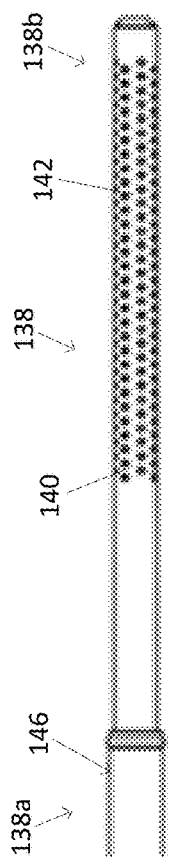
FIG. 27A illustrates a side view of a variation of a muffler.

FIG. 27A illustrates that the muffler 138 can be a removable insert. The muffler 138 can have a tool connector 146. The tool connector 146 can have a lip 147. The muffler proximal end 138a can have the tool connector 146. The tool connector 146 can be attached to or integrated with the muffler 138. The tool connector 146 can be removably attached to the muffler 138. The tool connector 146 can be attached to a fluid reservoir, attachment tool (e.g., attachment tool 48), or both. The tool connector 146 can fit into the attachment port 20. The muffler 138 can engage with the tool first engager 21*a*, the tool second engager 21*b*, or both. For example, the tool connector 146 can be removably engageable with the tool first engager 21*a*, the tool second engager 21*b*, or both. The attachment tool 48 can be an insertion tool. The fluid reservoir can be, for example, a syringe having a fluid chamber.

Having the muffler 138 be a removable insert or otherwise removably attachable to the devices described herein (e.g., devices 10, devices 200) can advantageously leave a space inside the devices that is open after fluid (e.g., fluid 96) is delivered and the muffler 138 is removed from the device. The space can remain open temporarily or permanently. The space can advantageously inhibit or prevent post-implantation migration of the fluid 96 away from the device. For example, the space can bias movement of fluid post-implantation toward the device (e.g., toward a center of the device 10). The center of the device 10 can be the device longitudinal axis $8_L$. This can desirably help reduce the risk of the fluid 96 from causing complications post-implantation of the device by migrating (e.g., creeping) away from the device before the fluid 96 sets or fully hardens.

As another example, the removal of the muffler 138 from the device can create a vacuum which can pull the fluid 96 toward the device. This can help reduce the amount of post-implantation migration of the fluid 96. When the muffler 138 is removed from the device, some or all of the fluid inside the device channel 28 can be removed, leaving an open space. As yet another example, when the muffler 138 is removed, the fluid 96 in the device channel 28 can remain in the device channel 28 such that no open space is formed by the removal of fluid when the muffler 138 is removed.

The muffler 138 can be removed from the device when the fluid 96 is not hardened, partially hardened, or fully hardened. The fenestrations 140 can have fluid cutting edges to help with the removal of the muffler 138. Bone can grow into the open space left behind after the muffler 138 is removed. As another example, the fluid 96 can inhibit or prevent bone from growing into the open space. The open space can be defined by the device (e.g., a wall or surface of the device) and/or by the fluid 96 (e.g., the fluid 96 in the fenestrations 74 and/or the fluid 96 coated on an outer and/or inner surface of the device). For example, the open space can be a channel of the device (e.g., device 10, device 200), such as channel 28, channel 45, channel 202, or any combination thereof. The open space can be the entire channel of the device or any portion thereof.

Figure 27B:
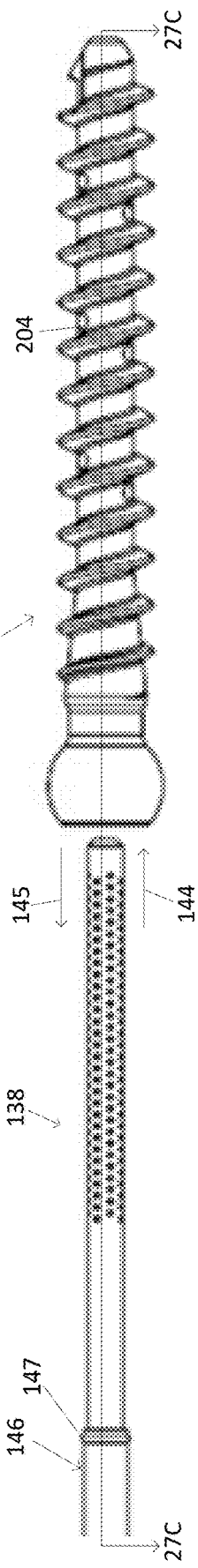
FIG. 27B illustrates the muffler of FIG. 27A and a variation of an attachment device.

FIG. 27B illustrates that the muffler 138 can be removably inserted into the device (e.g., device 10, device 200), as indicated by arrow 144. The muffler 138 can be translated into the device channel (e.g., channel 20, channel 202), rotated into the device channel, or both. The muffler 138 and the device can be engaged with one another, for example, via a releasable screw fit, friction fit, snap fit, magnetic fit, glue fit, loose fit, or any combination thereof.

FIG. 27B further illustrates that that the muffler 138 can be removed from the device (e.g., device 10, device 200) after being inserted into it, as indicated by arrow 145. The muffler 138 can be translated out of the device channel (e.g., channel 28, channel 202), rotated out of the device channel, or both.

Figure 27C:
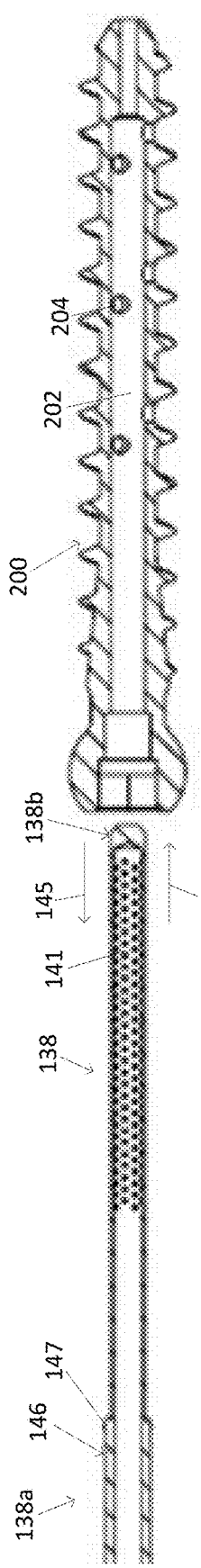
FIG. 27C illustrates a variation of a longitudinal cross-sectional view of the muffler and attachment device of FIG. 26B taken along line 27C-27C.

FIG. 27C illustrates that the removable muffler 138 can have a closed distal terminal end.

Figure 27D:
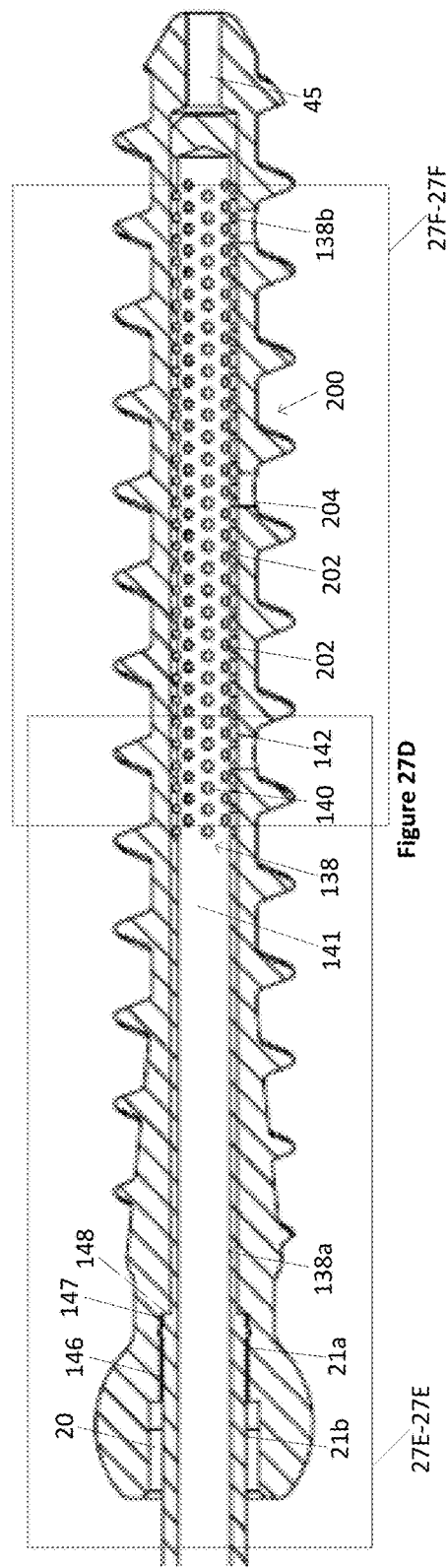
FIG. 27D illustrates the muffler and attachment device of FIG. 27C with the muffler in the attachment device.

FIG. 27D illustrates that the muffler the lip 147 can engage with a tool seat 148 to prevent over insertion of the muffler in the device channel (e.g., channel 202). The tool connector 146 can be inserted into the tool attachment port 20. The tool connector 146 can have a shape that matches the shape of the tool attachment port 20 (e.g., a hexagonal shape).

FIG. 27D further illustrates that when the muffler 138 is inserted into the device (e.g., device 10, device 200), some of the muffler fenestrations 140 can be aligned with the device fenestrations (e.g., fenestrations 74, fenestrations 204) and some of the muffler fenestrations 140 can be aligned with the wall of the of device between the device fenestrations. The muffler fenestrations 140 aligned with the device wall can be misaligned with the device fenestrations. When the muffler 138 is inserted into the device and there is space between the outer surface of the muffler 138 and the inner surface that defines the device channel, fluid can flow through muffler fenestrations 140 that are aligned and misaligned with the device fenestrations. When the muffler 138 is inserted into the device and there is not space between the outer surface of the muffler 138 and the inner surface that defines the device channel, fluid can flow through muffler fenestrations 140 aligned with the device fenestrations but not through the misaligned muffler fenestrations 140. The muffler 138 can thereby function as a universal flow controller for any given attachment device, as the density of the muffler fenestrations 140 along the length of the muffler 138 can desirably help ensure that regardless of the attachment device that the muffler 138 is inserted into, the muffler 138 can regulate the flow through the attachment device.

The muffler 138 can have one or multiple fluid delivery positions while partially or fully inserted into the device. For example, the muffler 138 can be fully inserted into the device and can be rotated into two or more multiple positions (e.g., 2 to 5 or more positions) that have a different amount of overlap between the device and muffler fenestrations 74, 140 and 204, 140. For example, the device can have stops which can secure the muffler 138 into three fluid delivery positions. The stops can be friction stops such as bumps. When the muffler 138 is in the first fluid delivery position, the overlap between the muffler and device fenestrations can be 100% such that the muffler fenestrations 140 are 100% unobstructed, allowing for the fluid to flow through the muffler and device at full capacity. When the muffler 138 is in the second fluid delivery position, the overlap between the muffler and device fenestrations can be from about 15% to about 75%, including every 5% increment within this range (e.g., 50%), such that the muffler fenestrations 140 are 15% to 75% unobstructed (e.g., 50% obstructed), allowing for the fluid to flow through the muffler and device at 15% to 75% capacity (e.g., 50% capacity). For example, when the muffler 138 is in the second fluid delivery position, a portion of the device fenestrations can overlap with a first portion of the muffler fenestrations 140 and a portion of the shaft wall can overlap with a second portion of the muffler fenestrations 140. When the muffler 138 is in the third fluid delivery position, the overlap between the muffler and device fenestrations can be from about 15% to about 75%, including every 5% increment within this range (e.g., 25%), such that the muffler fenestrations 140 are 15% to 75% unobstructed (e.g., 25% obstructed), allowing for the fluid to flow through the muffler and device at 15% to 75% capacity (e.g., 25% capacity). For example, when the muffler 138 is in the third fluid delivery position, a portion of the device fenestrations can overlap with a first portion of the muffler fenestrations 140 and a portion of the shaft wall can overlap with a second portion of the muffler fenestrations 140. The muffler 138 can be rotated in a first direction (e.g., clockwise) from the first to second, second to third, and third to first fluid delivery positions. The muffler 138 can be rotated in a second direction (e.g., counterclockwise) from the first to second, second to third, and third to first fluid delivery positions. The muffler 138 can be initially inserted into the first, second, or third fluid delivery position. Toggling the muffler 138 between the various fluid delivery positions can advantageously allow control over the flow through the muffler and device into the surrounding bone. As another example, the muffler 138 can be rotated without regard to any friction stops or specific positions. The user can rotate the muffler 138 into any fluid delivery position, or where the muffler and device are configured to have multiple step-wise fluid delivery positions, the user can rotate the muffler into any of the defined positions (e.g., first, second, or third fluid delivery position) as desired. In this way the device fenestrations 74, the muffler fenestrations 140, the rotational position of the muffler 138 when partially or fully inserted into the device, or any combination thereof can control the fluid flow through the device and into surrounding bone.

The density of the muffler fenestrations 140 can be, for example, from 1 to 20 or more fenestrations 140 per about 0.5 cm² to about 1.5 cm² of the device 10, including every 1 fenestration 140 increment within this range and every 0.1 cm² increment within this range. The size, shape, number and arrangement of device fenestrations can be different for different attachment devices. The muffler fenestration density can advantageously allow the muffler 138 to be used with a variety of different attachment devices. The size, shape, number and arrangement of the muffler fenestrations 140 can desirably allow the muffler to function as a universal flow controller. For example, the muffler 138 can have longitudinal slots extending along the length of the muffler 138. The muffler can have 5 to 50 or more longitudinal slots that run a length of the muffler 138 (e.g., the length where the muffler fenestrations 140 are shown in FIG. 27D). So that the muffler 138 can function as a universal flow controller, such elongated slots can be separated by the distance $L_F$, for example, from about 0.50 mm to about 4.00 mm, or more narrowly from about 0.50 mm to about 3.00 mm, or more narrowly from about 0.50 mm to about 2.00 mm, or more narrowly from about 0.5 mm to about 1.00 mm, including every 0.25 mm increment within these ranges. The distance $L_F$ can for such elongated slots can be measure long a perimeter (e.g., circumference) of the muffler 138.

FIG. 27D further illustrates that the muffler and device longitudinal axes can be concentric with one another.

Figure 27E:
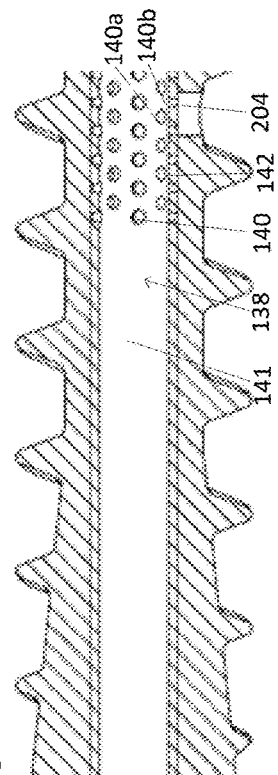
FIG. 27E is a magnified view of the muffler and attachment device of FIG. 27D at section 27E-27E.

FIG. 27E illustrates that a muffler first fenestration 140a and a muffler second fenestration 140b can be aligned with one of the device fenestrations (e.g., fenestrations 74, fenestrations 204). Zero, one or multiple muffler fenestrations 140 can be aligned with the device fenestrations when the muffler 138 is inserted into the device. The number of muffler fenestrations 140 aligned with each of the device fenestrations can be the same or different from one another such that zero muffler fenestrations can be aligned with some of the device fenestrations, one muffler fenestration 140 or a portion thereof can be aligned with some of the device fenestrations, two or more muffler fenestrations 140 or portions thereof can be aligned with some of the device fenestrations, or any combination thereof.

The size, shape, number and arrangement of the muffler fenestrations 140 can desirably allow for at least a portion of the muffler fenestrations to align with the device fenestrations so that flow can be controlled through the device.

FIG. 27E further illustrates that the tool connector 146 can have a device engager 149 and that the device can have a muffler engager 151. The device and muffler engagers 149, 151 can be engaged with one another, for example, via a screw fit, friction fit, snap fit, magnetic fit, glue fit, loose fit, or any combination thereof.

Figure 27F:
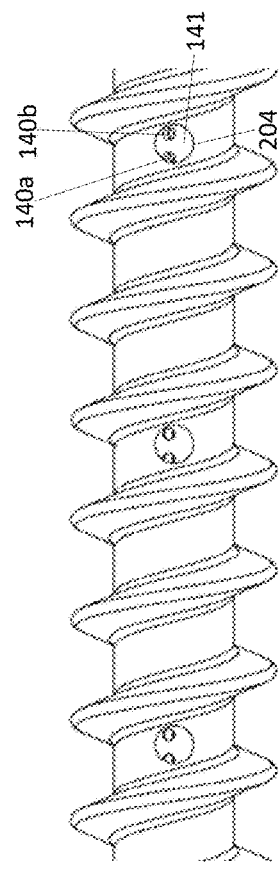
FIG. 27F is a magnified side view of the muffler and attachment device of FIG. 27D at section 27F-27F.

FIG. 27F illustrates that a portion of the muffler first fenestration 140a and the entire cross-sectional area of the muffler second fenestration 140b can be aligned with one of the device fenestrations (e.g., fenestrations 74, fenestrations 204).

FIGS. 27A-27F illustrate that the muffler 138 can be inserted into any variation of a conventional device 200. The muffler 138 can be permanently or removably inserted into the device 200, as indicated by arrow 144. Where the muffler 138 is permanently inserted into the device 200, the tool connector 146 can be detached from the muffler 138 so that the muffler and device 138, 200 can be implanted in bone. In this way the muffler 138 can be implanted in bone inside the device 200. As another example, where the muffler 138 is permanently inserted into the device 200, a tool can be detached from the tool connector 146 so that the tool connector, muffler and device 146, 138, 200 can be implanted in bone. In this way the tool connector and muffler 146, 138 can be implanted in bone inside the device 200. As another example, the muffler 138 can be removed from the device 200 after fluid is delivered through the muffler and device 138, 200 into bone near the device 200. Removal of the muffler 138 from the device 200 can be indicated by arrow 145. For variations in which the muffler 138 remains in the device 200 such that the muffler and device 138, 200 are both implanted in bone, arrow 145 can indicate the tool connector 146 being detached from the muffler 138, the device 200, or both. The tool connector 146 and/or a tool attached to the tool connector 146 can be used to insert the muffler 138 into the device 200, can be used to insert the device 200 into the bone, or both. The tool can be the attachment tool 48, a fluid delivery tool, or a tool that can both insert the muffler 138 into the device 200 and deliver fluid through the muffler and device 138, 200. The tool connector 146 and/or the tool can remove the muffler 138 from the device 200, can remove the device 200 from the bone, can remove the device 200 from the fluid (e.g., after implantation), or any combination thereof. The fluid delivered into the bone through the device 200 can have the fluid distribution 97.

Figure 27G:
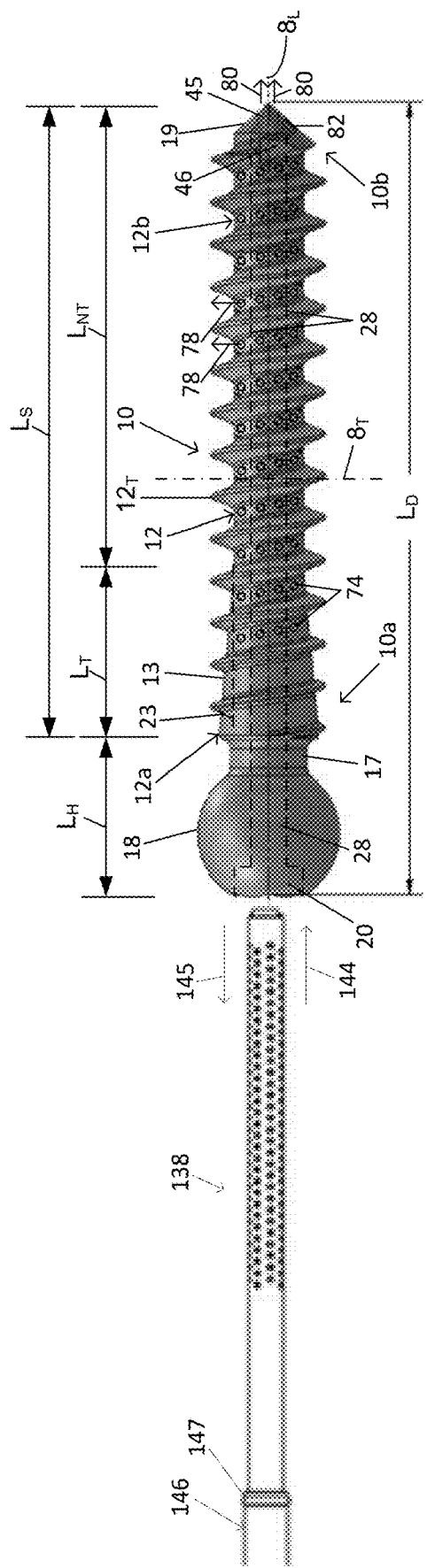
FIG. 27G illustrates the muffler of FIG. 27A and the attachment device of FIG. 1A.
Figure 27H:
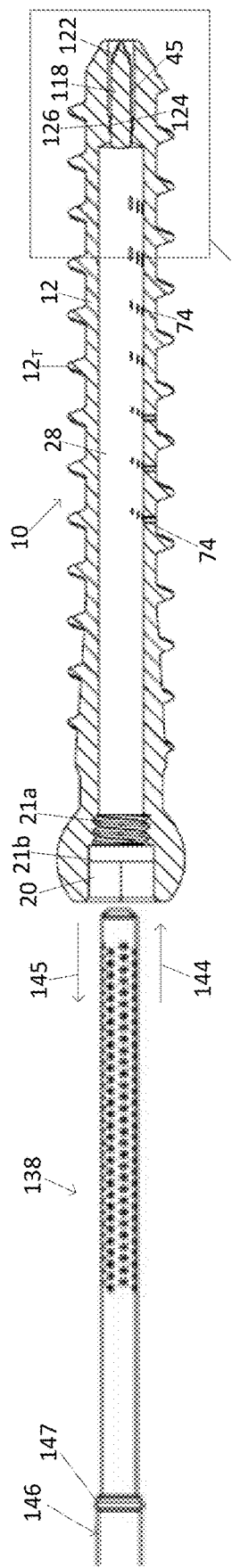
FIG. 27H illustrates the muffler of FIG. 27A and the attachment device of FIG. 20E.

FIGS. 27G and 27H illustrate that the muffler 138 can be inserted into any variation of the device 10. The muffler 138 can be permanently or removably inserted into the device 10, as indicated by arrow 144. Where the muffler 138 is permanently inserted into the device 10, the tool connector 146 can be detached from the muffler 138 so that the muffler and device 138, 10 can be implanted in bone. In this way the muffler 138 can be implanted in bone inside the device 10. As another example, where the muffler 138 is permanently inserted into the device 10, a tool can be detached from the tool connector 146 so that the tool connector, muffler and device 146, 138, 10 can be implanted in bone. In this way the tool connector and muffler 146, 138 can be implanted in bone inside the device 10. As another example, the muffler 138 can be removed from the device 10 after fluid is delivered through the muffler and device 138, 10 into bone near the device 10. Removal of the muffler 138 from the device 10 can be indicated by arrow 145. For variations in which the muffler 138 remains in the device 10 such that the muffler and device 138, 10 are both implanted in bone, arrow 145 can indicate the tool connector 146 being detached from the muffler 138, the device 10, or both. The tool connector 146 and/or a tool attached to the tool connector 146 can be used to insert the muffler 138 into the device 10, can be used to insert the device 10 into the bone, or both. The tool can be the attachment tool 48, a fluid delivery tool, or a tool that can both insert the muffler 138 into the device 10 and deliver fluid through the muffler and device 138, 10. The tool connector 146 and/or the tool can remove the muffler 138 from the device 10, can remove the device 10 from the bone, can remove the device 10 from the fluid (e.g., after implantation), or any combination thereof. The fluid delivered into the bone through the device 10 can have the fluid distribution 97.

FIG. 28A illustrates that the muffler 138 can be a mesh tube. The cells or openings in the mesh can be the muffler fenestrations 140. The mesh can include one or multiple struts. The muffler fenestrations 140 can be the space between the struts. The struts can be solid or can have one or more muffler fenestrations 140.

The muffler 138 can have a proximal connector 139a and a distal connector 139b. The proximal connector 139a can be a tube that connects the muffler 138 to the tool connector 146. The distal connector 139b can be a tube. The distal connector 139b can be a cap. The distal end of the mesh can be connected to the muffler distal connector 139b and the proximal end of the mesh can be connected to the muffler proximal connector 139a. The tool connector 146 can be a fluid reservoir engager or can be connected to a fluid reservoir engager.

The proximal connector 139a can be removably attached to the tool connector 146 such that the muffler 138 can be implanted with the device. For example, the muffler 138 can be detached from the tool connector 146 after the fluid 96 is injected into the bone through the muffler 138 and the device. The connector 146 can then be withdrawn from the device, leaving the muffler 138 in place so that the muffler 138 can be a live-in liner or a live-in insert.

FIG. 28B illustrates that the muffler 138 can be inserted in the device according to arrow 144.

FIG. 28B further illustrates that that the muffler 138 can be removed from the device (e.g., device 10, device 200) after being inserted into it, as indicated by arrow 145. The muffler 138 can be translated out of the device channel (e.g., channel 28, channel 202), rotated out of the device channel, or both.

FIG. 28C illustrates that the muffler distal end 138b can have a terminal distal end $138b_{TE}$ that can be closed or open.

FIG. 28C further illustrates that the muffler 138 can have a position index 150. The position index 150 can be on the muffler 138 (e.g., the muffler shaft, the muffler mesh, the proximal connector 139a, the distal connector 139b), the tool connector 146, or any combination thereof. The device (e.g., device 10, device 200) can have a position index 152, for example, on the cap 18, the neck 17, the device shaft, or any combination thereof. The muffler position index 150 can be aligned with the device position index 152 to align the muffler fenestrations 140 with the device fenestrations (e.g., fenestrations 74, fenestrations 204). The position indexes 150 and 152 can be radiopaque.

FIG. 28D illustrates that the muffler fenestrations 140 can defined between the mesh struts and joints 154, 155. FIG. 28D illustrates that some or all a portion of multiple fenestrations 140 in the mesh can be aligned with the device fenestrations (e.g., fenestrations 74, fenestrations 204) when the muffler 138 is inserted into the device. For example, FIG. 28D illustrates that a portion of the muffler fenestrations 140a-140f can be at least partially aligned with the device fenestration 204a. As another example, FIG. 28D illustrates that a portion of the muffler fenestrations 140g-140k can be at least partially aligned with the device fenestration 204b.

FIGS. 28A-28D illustrate that the muffler 138 can be inserted into any variation of a conventional device 200. The muffler 138 can be permanently or removably inserted into the device 200, as indicated by arrow 144. Where the muffler 138 is permanently inserted into the device 200, the tool connector 146 can be detached from the muffler 138 so that the muffler and device 138, 200 can be implanted in bone. In this way the muffler 138 can be implanted in bone inside the device 200. As another example, where the muffler 138 is permanently inserted into the device 200, a tool can be detached from the tool connector 146 so that the tool connector, muffler and device 146, 138, 200 can be implanted in bone. In this way the tool connector and muffler 146, 138 can be implanted in bone inside the device 200. As another example, the muffler 138 can be removed from the device 200 after fluid is delivered through the muffler and device 138, 200 into bone near the device 200. Removal of the muffler 138 from the device 200 can be indicated by arrow 145. For variations in which the muffler 138 remains in the device 200 such that the muffler and device 138, 200 are both implanted in bone, arrow 145 can indicate the tool connector 146 being detached from the muffler 138, the device 200, or both. The tool connector 146 and/or a tool attached to the tool connector 146 can be used to insert the muffler 138 into the device 200, can be used to insert the device 200 into the bone, or both. The tool can be the attachment tool 48, a fluid delivery tool, or a tool that can both insert the muffler 138 into the device 200 and deliver fluid through the muffler and device 138, 200. The tool connector 146 and/or the tool can remove the muffler 138 from the device 200, can remove the device 200 from the bone, can remove the device 200 from the fluid (e.g., after implantation), or any combination thereof. The fluid delivered into the bone through the device 200 can have the fluid distribution 97.

FIGS. 28E and 28F illustrate that the muffler 138 can be inserted into any variation of the device 10. The muffler 138 can be permanently or removably inserted into the device 10, as indicated by arrow 144. Where the muffler 138 is permanently inserted into the device 10, the tool connector 146 can be detached from the muffler 138 so that the muffler and device 138, 10 can be implanted in bone. In this way the muffler 138 can be implanted in bone inside the device 10. As another example, where the muffler 138 is permanently inserted into the device 10, a tool can be detached from the tool connector 146 so that the tool connector, muffler and device 146, 138, 10 can be implanted in bone. In this way the tool connector and muffler 146, 138 can be implanted in bone inside the device 10. As another example, the muffler 138 can be removed from the device 10 after fluid is delivered through the muffler and device 138, 10 into bone near the device 10. Removal of the muffler 138 from the device 10 can be indicated by arrow 145. For variations in which the muffler 138 remains in the device 10 such that the muffler and device 138, 10 are both implanted in bone, arrow 145 can indicate the tool connector 146 being detached from the muffler 138, the device 10, or both. The tool connector 146 and/or a tool attached to the tool connector 146 can be used to insert the muffler 138 into the device 10, can be used to insert the device 10 into the bone, or both. The tool can be the attachment tool 48, a fluid delivery tool, or a tool that can both insert the muffler 138 into the device 10 and deliver fluid through the muffler and device 138, 10. The tool connector 146 and/or the tool can remove the muffler 138 from the device 10, can remove the device 10 from the bone, can remove the device 10 from the fluid (e.g., after implantation), or any combination thereof. The fluid delivered into the bone through the device 10 can have the fluid distribution 97.

Figure 29A:
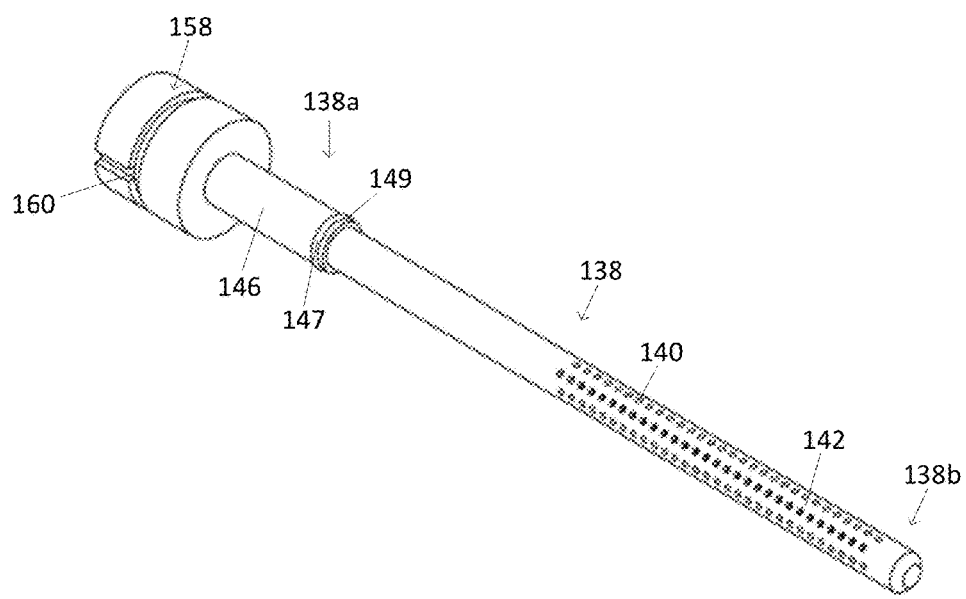
FIG. 29A illustrates a perspective view of a variation of a muffler.
Figure 29B:
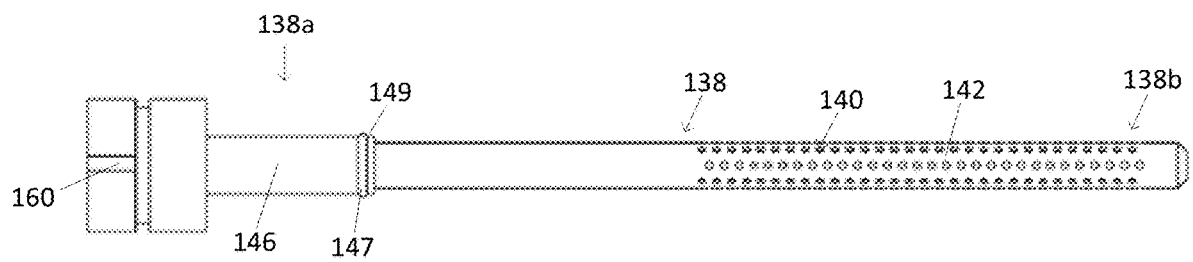
FIG. 29B illustrates a side view of the muffler of FIG. 29A.

FIGS. 29A and 29B illustrate that the device engager 149 can be screw threads. The device engager 149 can be screwed to corresponding threads on the muffler engager 151. FIGS. 29A and 29B further illustrate that a connector 158 can be attached to or integrated with the connector 146. The connector 158 can be a tool connector. For example, the connector 158 can be a reservoir connector, a bone attachment tool connector, or both. The connector 158 can connect to a fluid injector, an attachment tool, or both. The connector 158 can have grooves 160 configured for translational and/or rotational engagement with a tool. The tool can have a reservoir. The reservoir can be filled with fluid (e.g., fluid 96). The grooves 160 can lock the muffler 138 to the reservoir (not shown). The grooves can include a longitudinal groove connected to a circumferential groove.

FIG. 30A-30C illustrate that the muffler 138 can be coupled to the connector 158, that the muffler fenestrations 140 can be circular holes and that the muffler fenestrations 140 can be arranged in longitudinal rows. The muffler fenestrations 140 can be arranged in a helical pattern around the shaft of the muffler 138.

FIGS. 31A-31C illustrate that the muffler 138 can be coupled to the connector 158, that the muffler fenestrations 140 can be slots (e.g., rectangular slots, stadium-shaped slots) and that the muffler fenestrations 140 can be arranged in longitudinal rows. The muffler fenestrations 140 can be arranged in a helical pattern around the shaft of the muffler 138.

FIGS. 32A-32C illustrate that the muffler 138 can be coupled to the connector 158, that the muffler fenestrations 140 can be slots (e.g., rectangular slots, stadium-shaped slots) and that the muffler fenestrations 140 can be arranged in longitudinal rows. The muffler fenestrations 140 can be arranged in a helical pattern around the shaft of the muffler 138.

Figure 33:
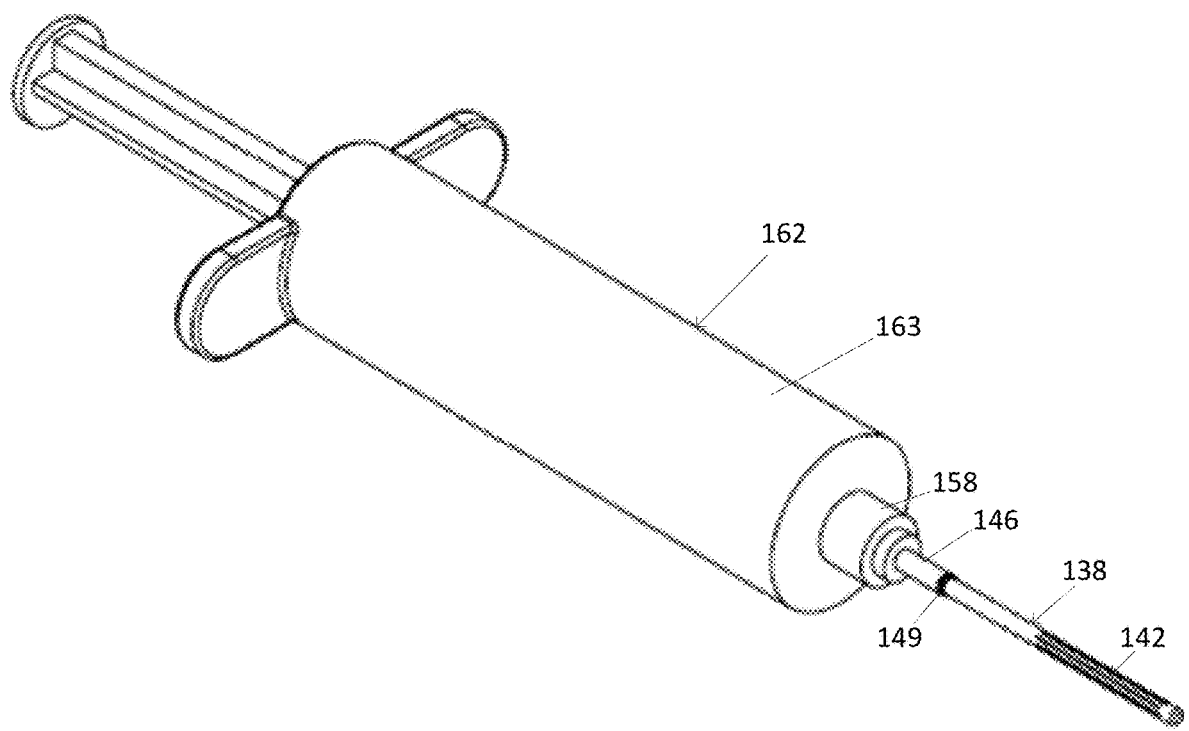
FIG. 33 illustrates a perspective view of a variation of a fluid delivery system.

FIG. 33 illustrates that the muffler 138 can be attached to a tool. The tool can be an attachment device, an injector, or any combination thereof. For example, the tool can be the tool 48, an injector 162, or any combination of features of the tool 48 and the injector 162 in a single tool. The muffler 138 can be connected to the tool via the connector 158. The injector can be a fluid injector (e.g., bone cement injector). The connector 158 can be attached to or integrated with the injector 162. The connector 158 can be removably attached to the injector 162. The injector 162 can be a pump, syringe, fluid deliverer, or any combination thereof. For example, FIG. 33 illustrates that the injector 162 can be a syringe. The injector 162 can hold the fluid 96, for example, in a reservoir 163. The injector 162 can be separate from or attached to the reservoir 163. The injector 162 can deliver the fluid 96 through the muffler 138 and the device into bone (e.g., bone 98).

Figure 34A:
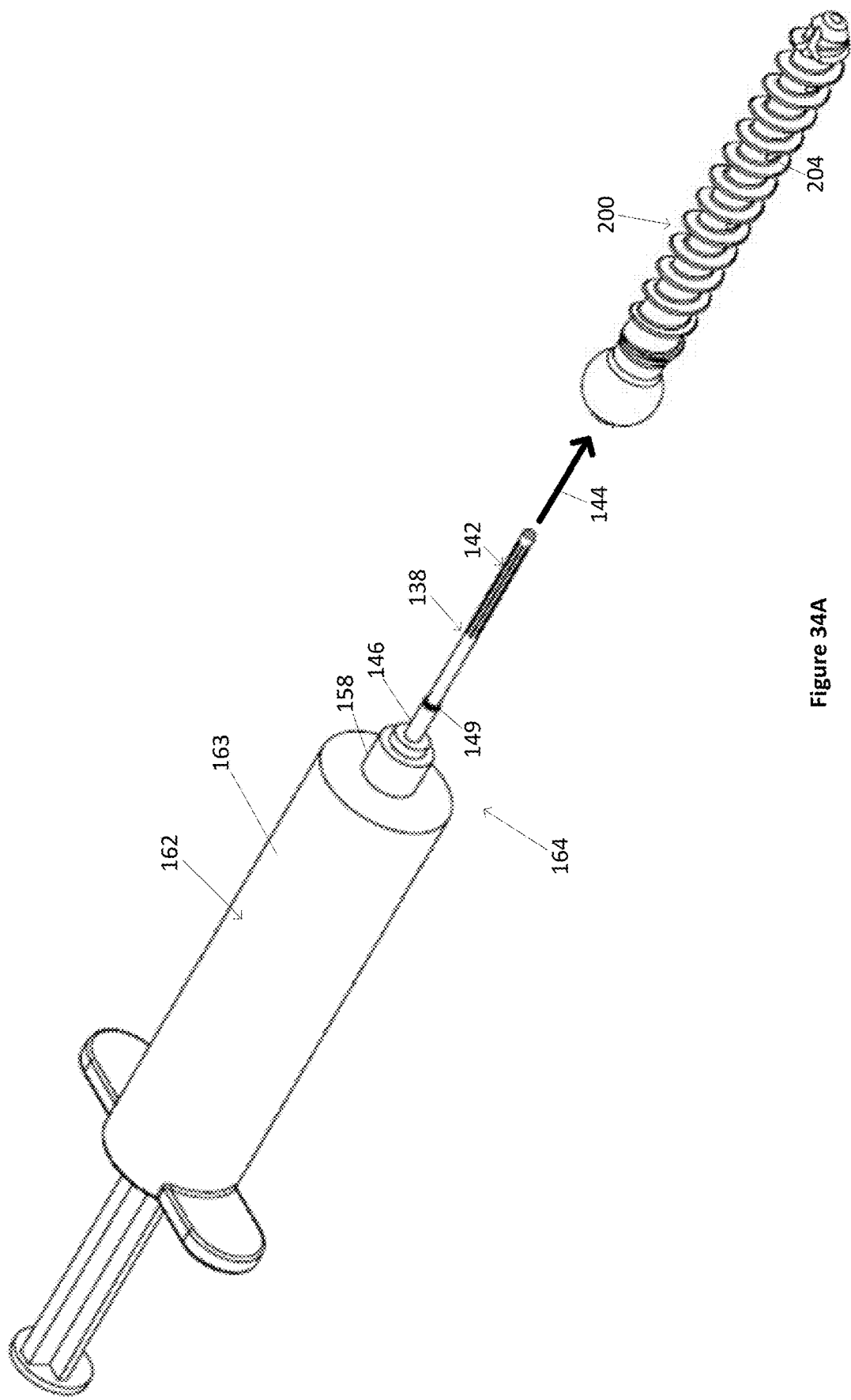
FIG. 34A illustrates a perspective of a variation of a fluid delivery system.

FIG. 34A illustrates that that the muffler 138 can be inserted into the device (e.g., device 10, device 200), as indicated by arrow 144. FIG. 34A further illustrates that the muffler 138 and the injector 162 can be a delivery system 164.

Figure 34B:
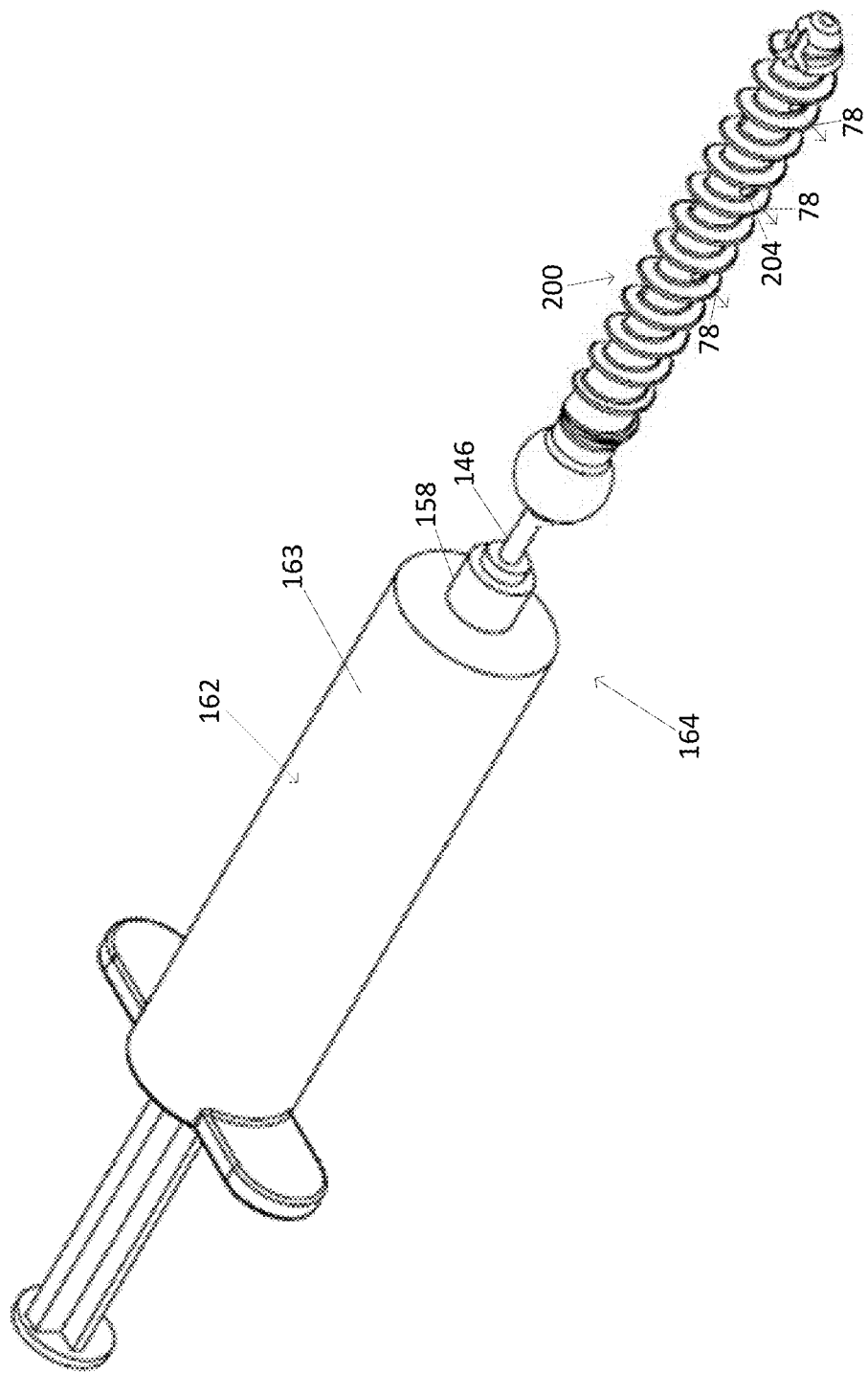
FIG. 34B illustrates a perspective of a variation of a fluid delivery system.

FIG. 34B illustrates that the injector 162 can be used to insert the muffler 138 into the device (e.g., device 10, device 200). When the muffler 138 is in the device, fluid can (e.g., fluid 96) be injected from the injector 162 into and through the muffler 138 and into and through the device fenestrations (e.g., fenestrations 74, fenestrations 204), for example, as shown by flow arrows 78 emanating from the device fenestrations 204.

Figure 34C:
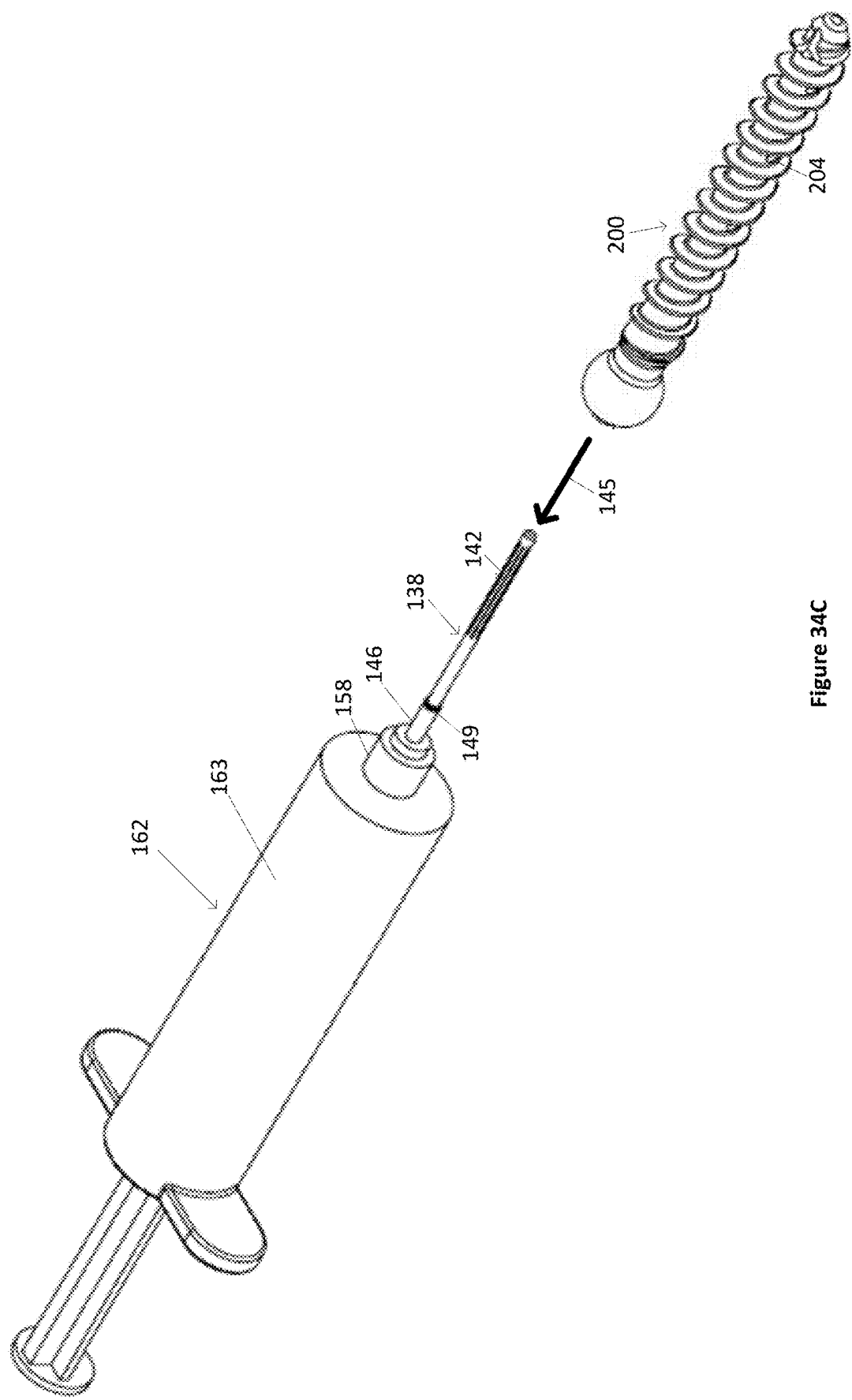
FIG. 34C illustrates a perspective of a variation of a fluid delivery system.

FIG. 34C illustrates that the muffler 138 can be removed from the device after fluid is injected through the device. For example, FIG. 34C illustrates that the injector 162 can withdraw the muffler 138 from the device. When the muffler 138 is removed after fluid injection, the inner cannulation of the device can be open/hollow, for example, because the muffler 138 can remove a core of fluid from inside the device cannulation after the fluid is injected.

Figure 34D:
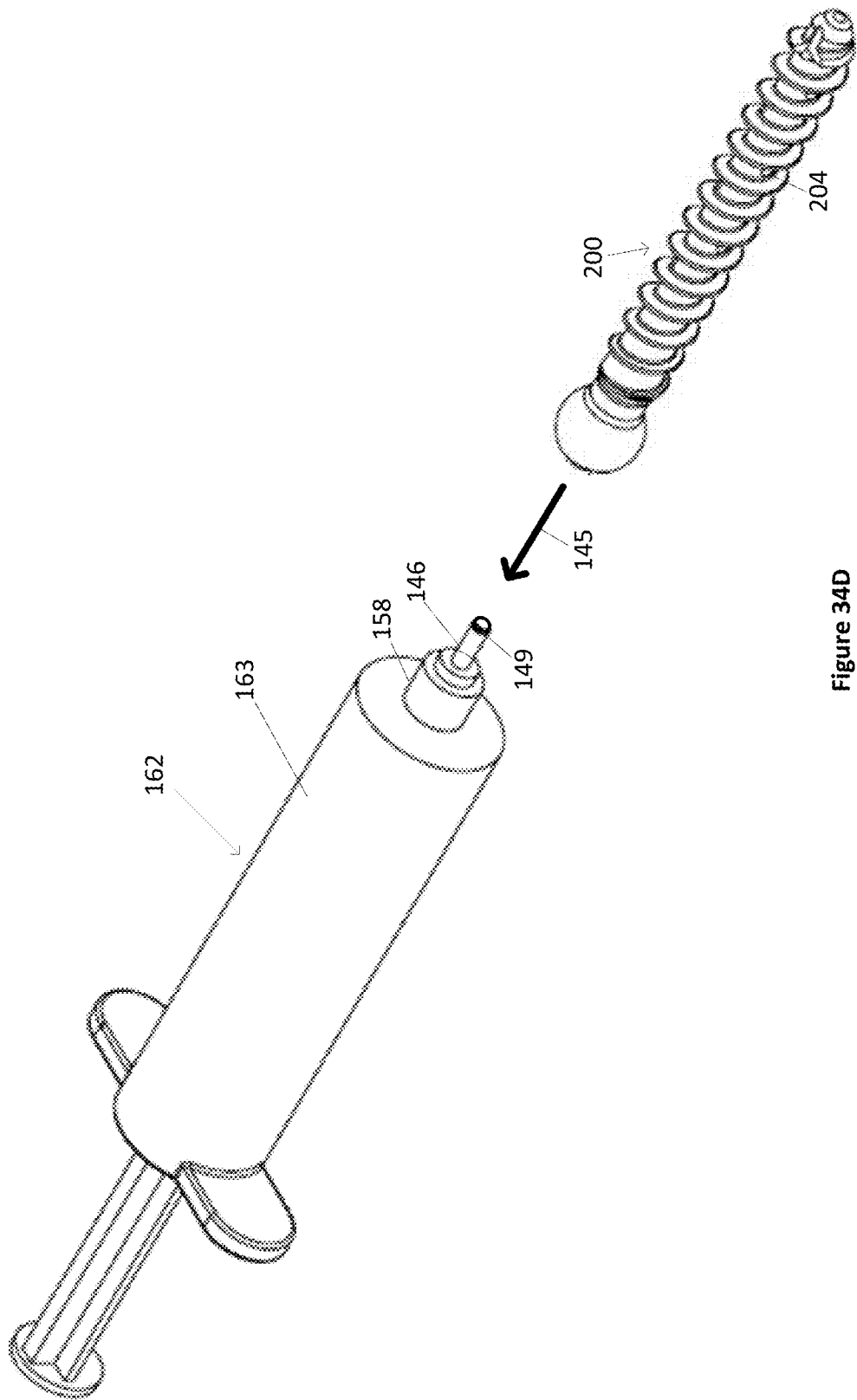
FIG. 34D illustrates a perspective of a variation of a fluid delivery system.
Figure 34E:
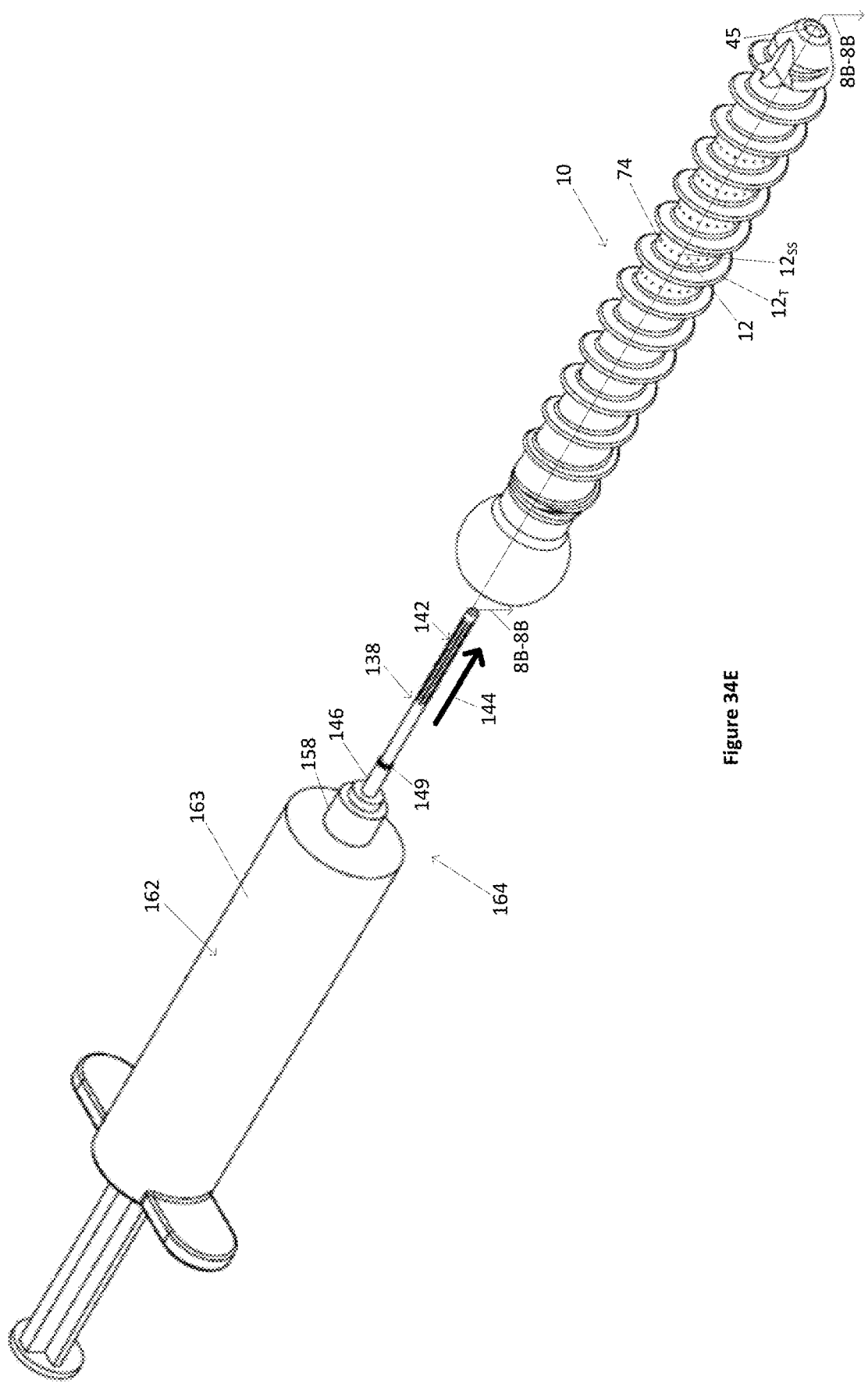
FIG. 34E illustrates a perspective of a variation of a fluid delivery system.
Figure 34F:
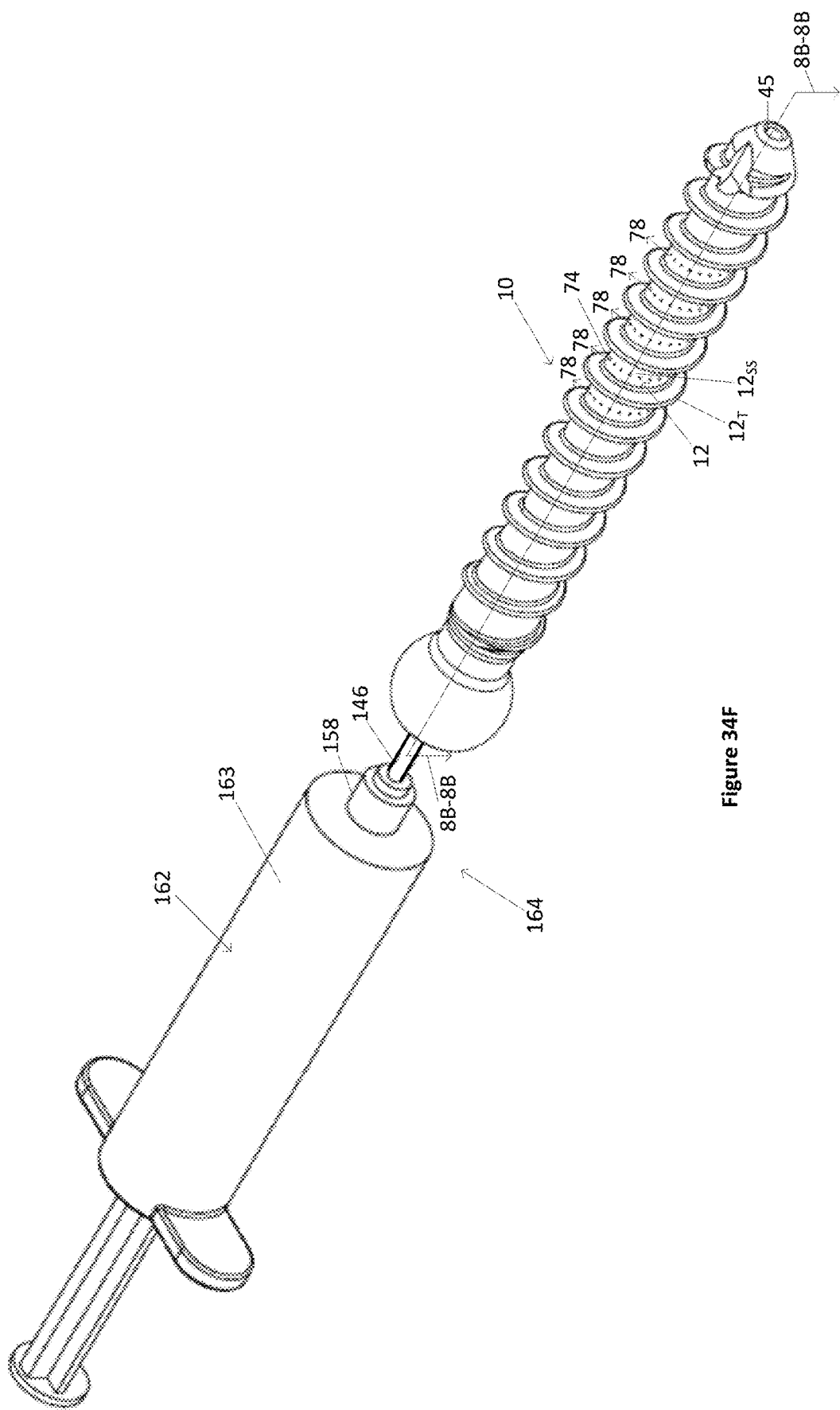
FIG. 34F illustrates a perspective of a variation of a fluid delivery system.
Figure 34G:
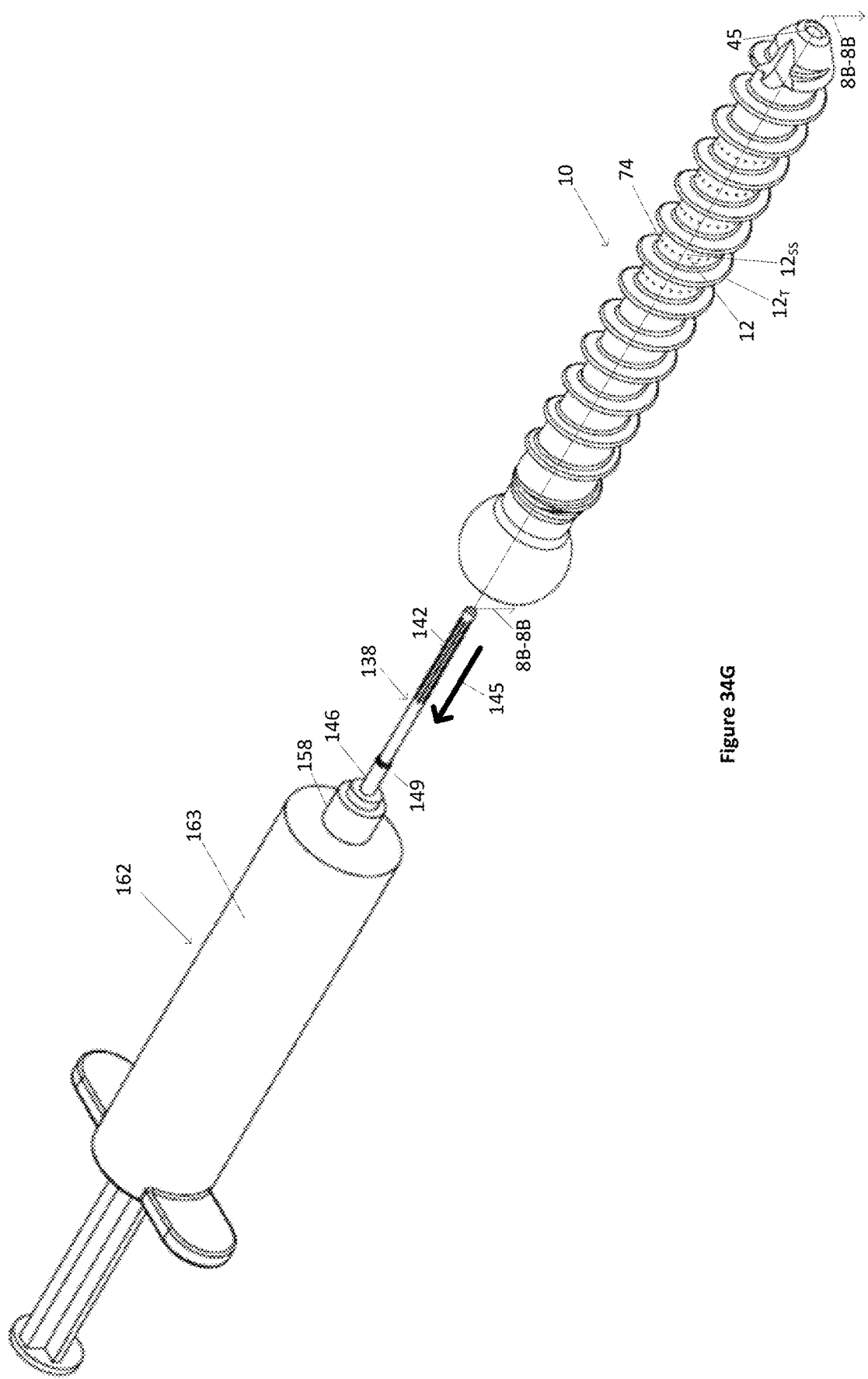
FIG. 34G illustrates a perspective of a variation of a fluid delivery system.
Figure 34H:
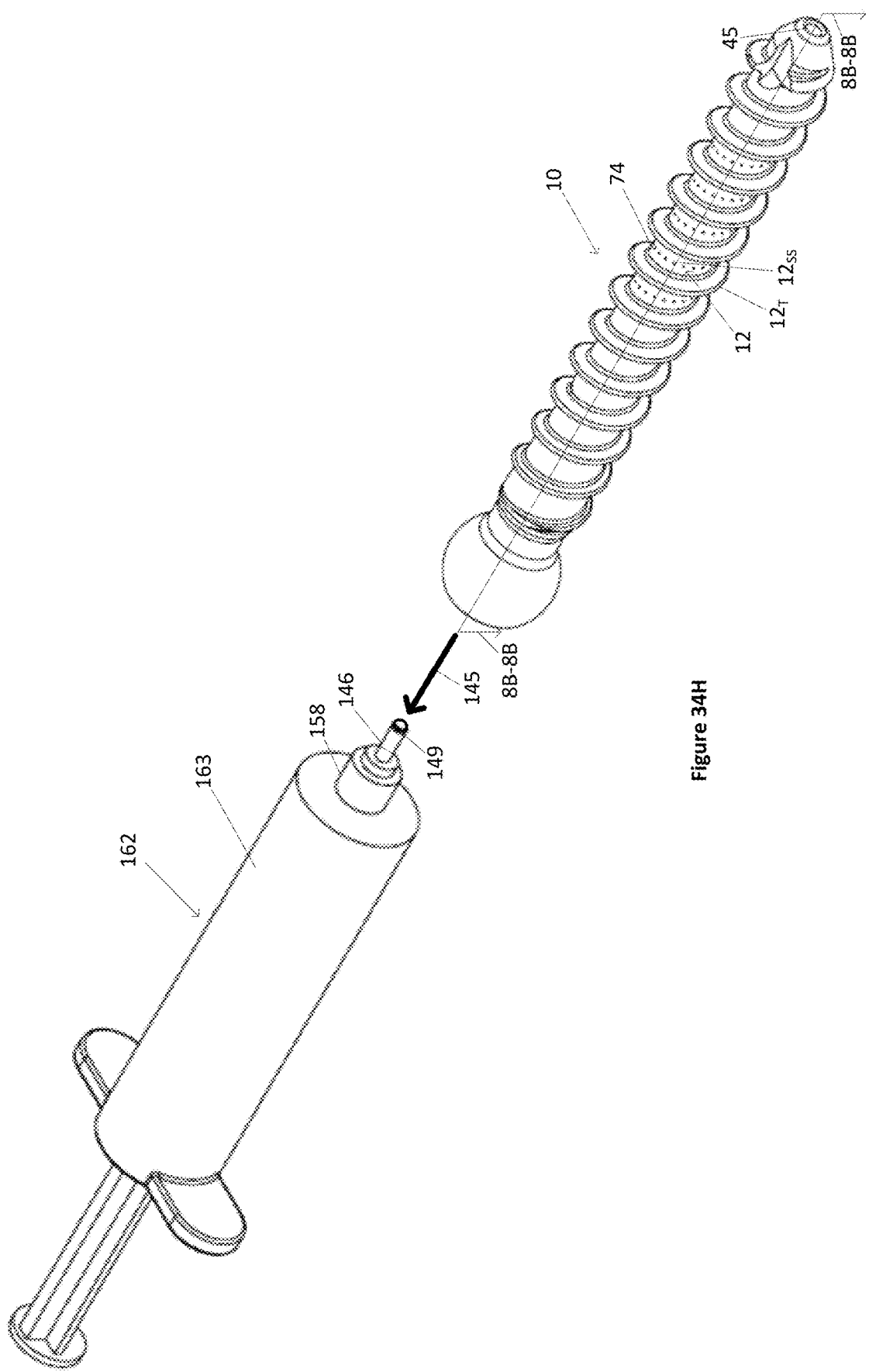
FIG. 34H illustrates a perspective of a variation of a fluid delivery system.

FIG. 34D illustrates that the muffler 138 can be implanted with the device (e.g., device 10, device 200). Once fluid is injected through the device, the injector 162 can be withdrawn, leaving the muffler 138 inside the device. When the reservoir is withdrawn away from the device, the connector 146 can detach from muffler 138, for example, from the shaft of the muffler 138.

FIGS. 34A-34D illustrate that the muffler 138 can be inserted into, fluid can be delivered through, and that the muffler 138 can be removed from any conventional device 200 with a tool (e.g., fluid injector 162). The muffler 138 can be inserted into the device 200 the full length of the channel 202 or any lesser amount. For example, the muffler 138 can have the same length as the channel 202 or can have a muffler length that is about 20% to about 80% the length of the channel 202, including every 10% increment within this range (e.g., 50%). The fluid delivered into the bone through the device 200 can have the fluid distribution 97.

FIGS. 34E-34H illustrate that the muffler 138 can be inserted into, fluid can be delivered through, and that the muffler 138 can be removed from any device 10 with a tool (e.g., fluid injector 162). The muffler 138 can be inserted into the device 10 the full length of the channel 20 or any lesser amount. For example, the muffler 138 can have the same length as the channel 20 or can have a muffler length that is about 20% to about 80% the length of the channel 20, including every 10% increment within this range (e.g., 50%). The fluid delivered into the bone through the device 200 can have the fluid distribution 97.

When fluid is injected through the device (e.g., device 10, device 200) or through the device and muffler 138, the fluid can simultaneously flow through some or all of the device fenestrations (e.g., fenestrations 74, fenestrations 204). As the muffler 138 and/or the device fills with fluid, the fluid can successively flow out of the device fenestrations where the pressure differential is greater enough for the fluid to pass through the device and/or muffler fenestrations. For example, fluid can flow through the muffler and/or device fenestrations as the fluid encounters the fenestrations, or after the fluid encounters the fenestrations and reaches a threshold pressure, such as the fluid pressures disclosed herein.

The fenestrations 74 can have a cross-sectional area 1% to 10%, 1% to 50%, or 1% to 100% or more the size of the cross-sectional area of the device channel (e.g., channel 28).

The flow rates and pressures in different shaft regions of the device (e.g., shaft regions $12i$, $12ii$, $12iii$) and/or of the muffler can be the same as or different from one another to create a uniform flow field through the device (e.g., device 10, device 200).

The fluid 96 can be injected and/or withdrawn through the device fenestrations. Some or all of the fluid 96 can be withdrawn from the bone (e.g., bone 98) or a space in the bone created by the device 10 after the fluid is injected through the device and before the fluid hardens. For example, the fluid can be withdrawn back into the device through the device fenestrations and into the device channel. As another example, the fluid can be withdrawn back into the device through the device and muffler fenestrations and into the device and muffler channels. This can be advantageous where too much fluid has been injected into the bone.

The muffler 138 can be, for example, a braided tube with a 1.5 mm outer diameter, 24 ends of 0.002" Ti and a 90 degree braid angle.

The muffler 138 can be, for example, a braided tube with a 1.5 mm outer diameter, 48 ends of 0.0015" Ti and 90 degrees braid angle.

The muffler 138 can be, for example, a braided tube with a 1.5 mm outer diameter, 24 ends of 0.003" PP and a 90 degree braid angle.

The muffler 138 can be, for example, a double wall tube, having a first braided tube with a 1.45 mm outer diameter, 24 ends of 0.002" Ti and a 90 degree braid angle and a second braided tube with a 1.5 mm outer diameter, 24 ends of 0.002" Ti and a 90 degree braid angle.

The muffler 138 can be, for example, a braided tube with 48 ends, a total 1.5 mm outer diameter, mix 24 ends of 0.0015" Ti having a 90 degree braid angle and 24 ends of 0.003" Ti.

The muffler 138 can be, for example, a laser slotted steel tube with a 1.5 mm outer diameter, a 0.002" wall with a low permeability wall pattern having 0.0015" radial holes.

The muffler 138 can be, for example, a laser slotted steel tube with a 1.5 mm outer diameter, a 0.002" wall with a medium permeability wall pattern having 0.002" radial holes.

The muffler 138 can be, for example, a laser slotted steel tube having a 1.5 mm outer diameter, a 0.002" wall with a high permeability wall pattern having 0.003" holes.

The muffler 138 can be, for example, a laser slotted steel tube having a 1.5 mm outer diameter, a 0.002" wall with laser cut slots The muffler 138 can be, for example, a laser slotted polymer tube (e.g., PP or PET or Nylon) having a 1.5 mm outer diameter, a 0.002" wall with a low permeability wall pattern having 0.0015" radial holes.

The muffler 138 can be, for example, a laser slotted polymer tube having a 1.5 mm outer diameter, a 0.002" wall with a medium permeability wall pattern having 0.002" radial holes.

The muffler 138 can be, for example, a laser slotted tube having a 1.5 mm outer diameter, a 0.002" wall with a high permeability wall pattern having 0.003" holes The muffler 138 can be, for example, a laser slotted polymer tube having a 1.5 mm outer diameter, a 0.002" wall with laser slots.

Figure 35:
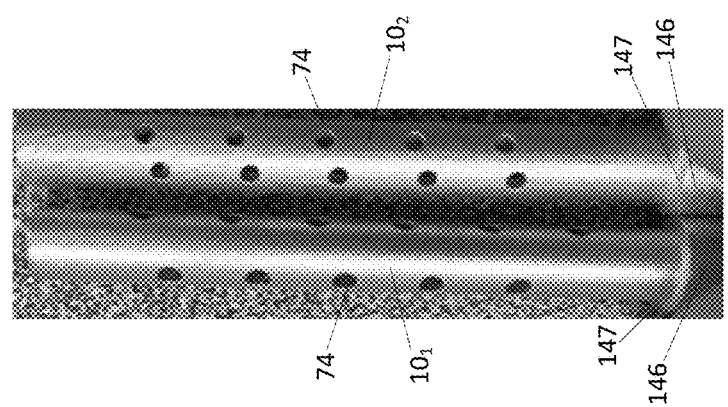
FIG. 35 illustrates a side view of two variations of an attachment device.

FIG. 35 illustrates a first device 101 and a second device 102. The second device 102 has smaller holes per unit length and per circumference than the first device 101. More holes per unit screw surface area (e.g., length×width (L*W)) can assure more uniform fluid around the device 10.

Figure 36A:
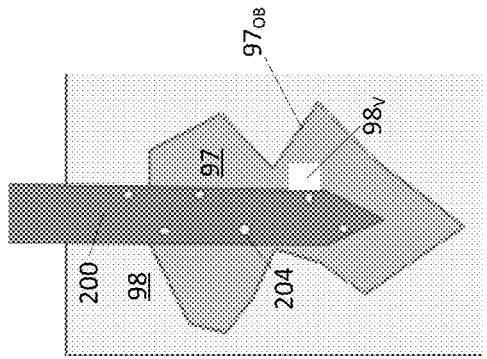
FIG. 36A illustrates a schematic variation an attachment device in bone.

FIG. 36A illustrates that the device 200 can be in bone 98 that has a void 98v. Resistance to bone cement flow in regions where the bone 98 touches/surrounds the device 200 can be R1. Resistance to bone cement flow in regions where the void 98v surrounds the device 200 can be R2. R1 can be greater than R2.

FIG. 36A further illustrates that when cement is injected with pressure P1, cement can flow into the bone 98 at a mass flow V1 and into the void at a mass flow V2. V2 can be greater than V1 because R2 is less than R1. V2 allows greater bone cement volume and greater bone cement distance from the screw then V1. The pressure differential R1 to R2 governs this result. R1 is greater than R2, and V2 greater than V1 shows that bone cement follows path of least resistance when injected into the bone 98.

Figure 36B:
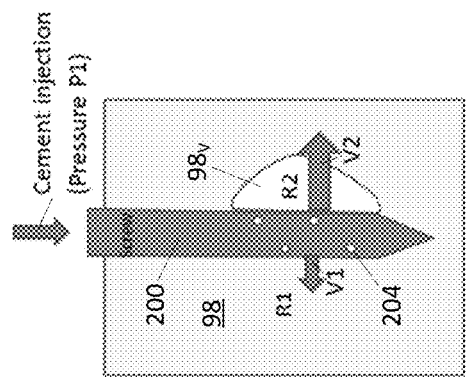
FIG. 36B illustrates the attachment device of FIG. 36A with a variation of a fluid distribution around the attachment device.

FIG. 36B illustrates a variation of a non-uniform flow distribution 47 that can result when the flow through the device 200 is not controlled with the device fenestrations 74 and/or with the muffler fenestrations 140. The delta or differential in resistance is the cause of cement leakage or traveling to the wrong location when using conventional devices such as the device 200.

Figure 37A:
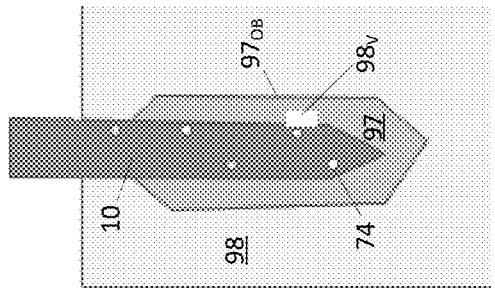
FIG. 37A illustrates a schematic variation an attachment device in bone.

FIG. 37A illustrates that the device 10 can be in bone 98 that has a void 98v. The fenestrations 74 can control the flow resistance such that R1 and R2 are the same or substantially the same. As a result, V2 can be the same or substantially the same as V1. The cement can flow into the void 98v with R2 resistance at the same rate as it flows into the bone 98 with R1 resistance, where R2 is less than R1. The bone cement can infiltrate the bone 98 and the void 98v the same or substantially the same. For example, the cement can penetrate the same distance (e.g., radial distance) away from the device 10 regardless of the resistance to flow from outside of the device 10, for example, regardless of whether the resistance is high (e.g., R1) or low (e.g., R2).

Figure 37B:
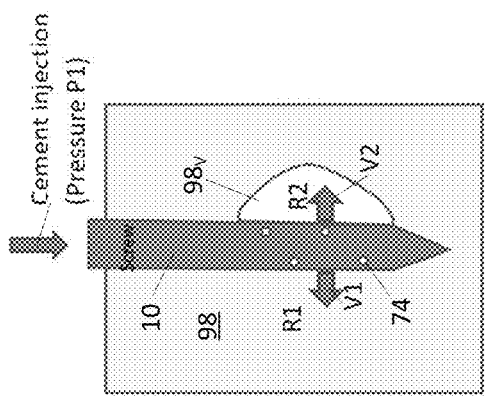
FIG. 37B illustrates the attachment device of FIG. 37A with a variation of a fluid distribution around the attachment device.

FIG. 37B illustrates a variation of a uniform flow distribution 47 that can result when fluid is injected through the device 10 and into the bone and void 98, 98v. FIG. 37B further illustrates a variation of a uniform flow distribution 47 that can result when the flow through the device 10 is controlled with the device fenestrations 74 and/or with the muffler fenestrations 140.

Figure 38A:
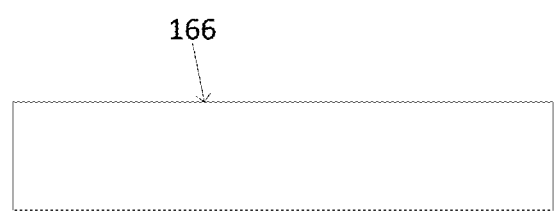
FIG. 38A illustrates a schematic of a variation of an external muffler.

FIG. 38A illustrates a variation of an external muffler 166. The external muffler 166 can control the flow of fluid through the device (e.g., device 10, device 200). The external muffler 166 can have the same properties as the internal muffler 138 except that the external muffler 166 is on the outside of the device and the internal muffler 138 is on the inside of the device. For example, the external muffler 166 can be bioabsorbable or non-bioabsorbable.

Figure 38B:
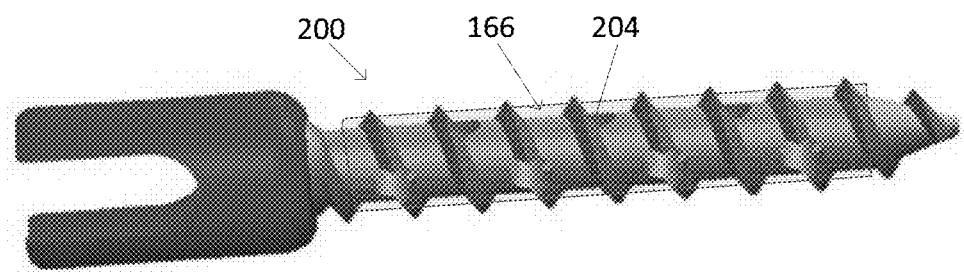
FIG. 38B illustrates a side view of a variation of an attachment device with the external muffler of FIG. 38A.
Figure 38C:
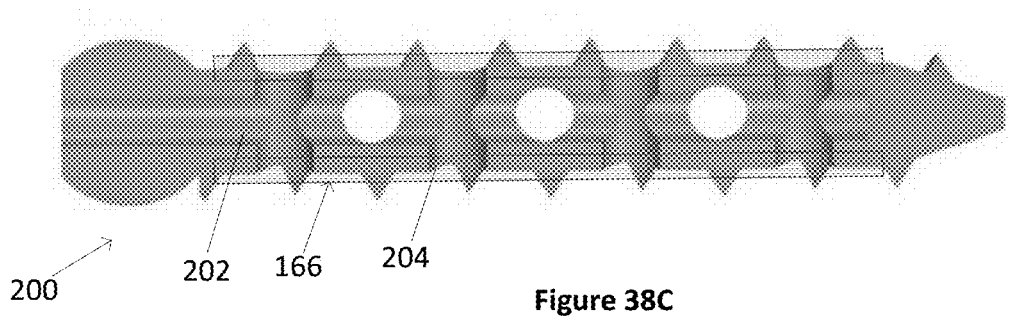
FIG. 38C illustrates a variation of a longitudinal cross-sectional view of the attachment device and external muffler of FIG. 38B.

FIGS. 38B and 38C illustrate that the external muffler 166 can be attached to or integrated with the device (e.g., device 10, device 200), for example, with an outer surface of the device. The external muffler 166 can be rigid or flexible. The external muffler 166 can conform to the shape of the device. The external muffler 166 can be a sleeve that fits of over the device.

FIGS. 39A and 39B illustrate multiple devices 10 inserted into vertebral bodies to buttress the spine and stop motion to allow fusion.

FIG. 40A a curved spine and FIG. 40B illustrates multiple devices 10 inserted into vertebral bodies to buttress the spine and stop motion to allow fusion.

Method of Use

The device 10 can have one or multiple configurations, one or more of which can correspond to various deployment stages or the transition from one stage to another. For example, the device 10 can have a deployment first stage (e.g., where the device 10 is inserted in bone), a deployment second stage (e.g., where a muffler 138 is inserted in the device 10), a deployment third stage (e.g., where bone cement is injected through muffler and device into surrounding bone), a deployment fourth stage (e.g., where the muffler 138 is removed from the device), or any combination thereof (e.g., where the muffler 138 is integrated with the device, the method can include the deployment first and third stages).

Additional deployment stages can include repositioning the device 10 (e.g., rotating the device 10 relative to the bone, advancing the device 10 further into the bone, partially withdrawing the device 10 from the bone, or any combination thereof) after an initial placement but prior to removal or a removal procedure. Additional deployment stages can include allowing bone to grow into the device 10 through one or more holes (e.g., in and/or through holes 74 and/or 140).

In the deployment first stage, the threads $12_T$ along the length of the device 10 can be progressively screwed into bone (e.g., progressively from the device distal end 10b to the device proximal end 10a). The deployment first stage can be completed when some (e.g., a majority) or all of the threads (e.g., threads $12_T$) are screwed into bone, or such that the shaft proximal end 12a is seated within the bore created by the device 10, is seated flush with at least a portion of an osteo surface (e.g., vertebra surface), or is seated above an osteo surface (e.g., by about 0.5 mm to about 2.0 mm).

In the deployment second stage, the muffler 138 can be inserted into the device 10, for example, into the shaft channel 28. The muffler 138 can be removably or irremovably attached to the shaft 12. The muffler 138 can be directly or indirectly attached to the shaft. The muffler 138 can be removably locked to the device 10 (e.g., to the shaft 12) with a locking mechanism.

In the deployment third stage, bone cement can be forced into and/or out of the device 10 and/or the muffler 138, for example, through the fenestrations 74 and/or 140 to achieve the desired amount of cement in the bone surrounding the device 10 and/or the muffler 138.

In the deployment fourth stage, the muffler 138 can be removed from the device 10.

The device 10 can be removed from the bone after being implanted into it, for example, 1 minute after implantation, 30 minutes after implantation, 1 day after implantation, or 1 or more years after implantation.

The muffler 138 can be removed from the bone after being implanted into it, for example, 1 minute after implantation, 30 minutes after implantation, 1 day after implantation, or 1 or more years after implantation.

The device and muffler 10, 138 can be removed from the bone after being implanted into it, for example, 1 minute after implantation, 30 minutes after implantation, 1 day after implantation, or 1 or more years after implantation.

FIGS. 41A and 41B illustrate the attachment devices 10 in various vertebrae 5 at the completion of the deployment first stage. As another example, FIGS. 41A and 41B illustrate the attachment devices 10 in various vertebrae 5 at the completion of the deployment second stage. As another example, FIGS. 41A and 41B illustrate the attachment devices 10 in various vertebrae 5 at the completion of the deployment third stage. As another example, FIGS. 41A and 41B illustrate the attachment devices 10 in various vertebrae 5 at the completion of the deployment fourth stage. As yet another example, FIGS. 41A and 41B illustrate the attachment devices 200 in various vertebrae 5 at the completion of the deployment first, second, third and fourth stages. The devices 10 and 200 can be screws such as polyaxial pedicle screws that can be used as part of a spinal fixation system (e.g., to attach a rod and/or a plate of a fixation system to a vertebra).

While 360 degree views of the devices (e.g., device 10, device 200) are not shown in the figures, the fenestrations (e.g., fenestrations 74, fenestrations 204) illustrated in FIGS. 1A-41B can be on the sides of the devices not visible in FIGS. 1A-41B such that the fenestrations can be distributed circumferentially around the device through the shaft and/or threads of the device, for example, 360 degrees around the shaft 12. Additionally or alternatively, the fenestrations (e.g., fenestrations 74, fenestrations 204) can be distributed in FIGS. 1A-41B without any fenestrations on the sides of the devices that are not visible in FIGS. 1A-41B.

U.S. Pat. Nos. 7,608,062, 7,608,097 and 8,574,273 are herein incorporated by reference in their entirety for all purposes. The disclosures in these patents can be combined in any combination with the present disclosure.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art.

The specific embodiments described herein are offered by way of example only. Moreover, such devices and methods may be applied to other sites within the body. Modification of the above-described assemblies and methods for carrying out the invention, combinations between different variations, and variations of aspects of the invention that are obvious to those of skill in the art are intended to be within the scope of the claims.

The specific variations described herein are offered by way of example only. The above-described variations, configurations, features, elements, methods and variations of these aspects can be combined and modified with each other in any combination. For example, all intermediate generalizations of the devices and methods disclosed herein are hereby explicitly disclosed. Any elements described herein as singular can be pluralized (i.e., anything described as "one" can be more than one). Any species element of a genus element can have the characteristics or elements of any other species element of that genus.

We claim:
1. A method for treating bone comprising:
inserting a pressure reduction device at least partially into a bone at a target site, wherein the pressure reduction device has a pressure reduction device lumen, a pressure reduction first fenestration, and a pressure reduction second fenestration, wherein during the inserting, a longitudinal center of the pressure reduction device lumen has a transverse width, wherein the pressure reduction first fenestration is proximal to the pressure reduction second fenestration, wherein the pressure reduction device comprises a mesh, wherein the pressure reduction first and second fenestrations are in the mesh, and wherein the mesh extends around a perimeter of the pressure reduction device lumen; and
flowing bone cement through the pressure reduction device lumen when the longitudinal center of the pressure reduction device lumen has the transverse width, then flowing the bone cement through the pressure reduction first fenestration, then flowing the bone cement into the target site,
wherein a pressure of the bone cement decreases when the bone cement flows through the pressure reduction first fenestration, wherein the pressure reduction first fenestration is on a lateral side of the pressure reduction device, and wherein the pressure reduction device is insertable in a bone screw having a bone screw fenestration having a bone screw fenestration length, wherein the mesh has a mesh length, and wherein the mesh length is greater than the bone screw fenestration length.

2. The method of claim 1, wherein the transverse width is a diameter and wherein the perimeter is a circumference.

3. The method of claim 1, wherein the mesh is insertable through a longitudinal end of a bone screw.

4. The method of claim 1, wherein the mesh is hollow and removably insertable in a bone screw.

5. The method of claim 1, wherein the pressure reduction device is insertable in a bone screw having a bone screw fenestration, wherein when the pressure reduction device is in the bone screw, the pressure reduction first and second fenestrations are simultaneously alignable with the bone screw fenestration.

6. The method of claim 1, wherein the pressure reduction device is insertable in a bone screw having a bone screw first fenestration and a bone screw second fenestration, wherein when the pressure reduction device is in the bone screw, the pressure reduction first fenestration is simultaneously alignable with the bone screw first and second fenestrations.

7. The method of claim 1, further comprising flowing bone cement through a bone screw, and wherein the mesh comprises a meshed metal and/or a strut.

8. The method of claim 1, wherein the pressure reduction first fenestration is smaller than the pressure reduction second fenestration, or wherein the pressure reduction second fenestration is on the lateral side of the pressure reduction device and at least 90° away from the pressure reduction first fenestration with respect to a longitudinal axis of the pressure reduction device, or wherein the pressure reduction device comprises a metal tube with a closed distal end.

9. A method for treating bone comprising:
inserting a pressure reduction device at least partially into a bone at a target site, wherein the pressure reduction device has a pressure reduction device lumen, a pressure reduction first fenestration, and a pressure reduction second fenestration, wherein during the inserting, a longitudinal center of the pressure reduction device lumen has a transverse width, wherein the pressure reduction first fenestration is proximal to the pressure reduction second fenestration, wherein the pressure reduction device comprises a mesh, wherein the pressure reduction first and second fenestrations are in the mesh, and wherein the mesh extends around a perimeter of the pressure reduction device lumen; and
flowing bone cement through the pressure reduction device lumen when the longitudinal center of the pressure reduction device lumen has the transverse width, then flowing the bone cement through the pressure reduction first fenestration, then flowing the bone cement into the target site,
wherein a pressure of the bone cement decreases when the bone cement flows through the pressure reduction first fenestration, wherein the pressure reduction first fenestration is on a lateral side of the pressure reduction device, and
wherein the pressure reduction first fenestration is smaller than the pressure reduction second fenestration, or wherein the pressure reduction second fenestration is on the lateral side of the pressure reduction device and at least 90° away from the pressure reduction first fenestration with respect to a longitudinal axis of the pressure reduction device, or wherein the pressure reduction device comprises a metal tube with a closed distal end.

10. The method of claim 9, wherein the transverse width is a diameter and wherein the perimeter is a circumference.

11. The method of claim 9, wherein the mesh is insertable through a longitudinal end of a bone screw.

12. The method of claim 9, wherein the mesh is hollow and removably insertable in a bone screw.

13. The method of claim 9, wherein the pressure reduction device is insertable in a bone screw having a bone screw fenestration, wherein when the pressure reduction device is in the bone screw, the pressure reduction first and second fenestrations are simultaneously alignable with the bone screw fenestration.

14. The method of claim 9, wherein the pressure reduction device is insertable in a bone screw having a bone screw first fenestration and a bone screw second fenestration, wherein when the pressure reduction device is in the bone screw, the pressure reduction first fenestration is simultaneously alignable with the bone screw first and second fenestrations.

15. The method of claim 9, further comprising flowing bone cement through a bone screw, and wherein the mesh comprises a meshed metal and/or a strut.

\* \* \* \* \*